(12) United States Patent
Gascoyne et al.

(10) Patent No.: US 7,105,081 B2
(45) Date of Patent: Sep. 12, 2006

(54) METHODS AND APPARATUS FOR ELECTROSMEAR ANALYSIS

(75) Inventors: Peter R. C. Gascoyne, Bellaire, TX (US); Jody V. Vykoukal, Houston, TX (US); Chandra Das, Sugar Land, TX (US); Frederick F. Becker, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 10/743,698

(22) Filed: Dec. 22, 2003

(65) Prior Publication Data

US 2004/0178068 A1    Sep. 16, 2004

Related U.S. Application Data

(60) Provisional application No. 60/435,938, filed on Dec. 20, 2002, provisional application No. 60/475,717, filed on Jun. 4, 2003.

(51) Int. Cl.
*G01N 27/26* (2006.01)
*G01N 27/447* (2006.01)
*G01N 33/48* (2006.01)

(52) U.S. Cl. .............. 204/547; 204/643; 435/40.51

(58) Field of Classification Search .............. 204/547, 204/643; 435/40.51
See application file for complete search history.

(56) References Cited

U.S. PATENT DOCUMENTS 4,250,026 A  *  2/1981  Giddings et al. ........... 209/155

| | | | |
|---|---|---|---|
| 5,191,899 A | 3/1993 | Strickland et al. ......... 128/756 |
| 5,302,898 A | 4/1994 | Pethig et al. .............. 324/316 |
| 5,589,047 A | * 12/1996 | Coster et al. ............. 204/450 |
| 5,626,734 A | 5/1997 | Docoslis et al. ........... 204/547 |
| 5,858,192 A | 1/1999 | Becker et al. ............. 204/547 |
| 5,888,370 A | 3/1999 | Becker et al. ............. 204/643 |
| 5,993,630 A | 11/1999 | Becker et al. ............. 204/547 |
| 5,993,632 A | 11/1999 | Becker et al. ............. 204/547 |
| 6,264,815 B1 | 7/2001 | Pethig et al. .............. 204/547 |
| 6,287,832 B1 | 9/2001 | Becker et al. ........... 435/173.9 |

(Continued)

FOREIGN PATENT DOCUMENTS

WO    WO 01/14870    *  3/2001    .............. 204/547

OTHER PUBLICATIONS

Website of Tripath Imaging, Inc. (www.tripathimaging.com/usproducts/index.htm), Mar. 5, 2002. □□Accessed via internet archive at www.archive.org.*

(Continued)

*Primary Examiner*—Alan Diamond
*Assistant Examiner*—Jeffrey Barton
(74) *Attorney, Agent, or Firm*—Fulbright & Jaworski LLP

(57) ABSTRACT

Methods and apparatus for preparing a smear for cytopathology or other analysis. In a representative embodiment, cells of a sample are subjected to a dielectrophoretic force to segregate the cells into two or more zones of a surface. The particles are attached to the surface, thereby defining a "segregated smear." The segregated smear is then fixed and stained for cytopathology analysis.

45 Claims, 40 Drawing Sheets

U.S. PATENT DOCUMENTS

| | | | |
|---|---|---|---|
| 6,294,063 B1 | 9/2001 | Becker et al. | 204/450 |
| 6,352,838 B1 | 3/2002 | Krulevitch et al. | 435/34 |
| 6,387,707 B1 * | 5/2002 | Seul et al. | 436/164 |
| 6,436,662 B1 | 8/2002 | Mielzynska et al. | 435/40.5 |
| 6,437,551 B1 | 8/2002 | Krulevitch et al. | 324/71.1 |
| 6,673,225 B1 * | 1/2004 | Arnold | 204/547 |
| 2002/0076825 A1 * | 6/2002 | Cheng et al. | 436/174 |

OTHER PUBLICATIONS

Lee et al., "Micromachined Cell Handling Devices," *Conference of IEEE Engineering in Medicine and Biology Society*, 1019-1020, 1994.

Masuda et al., *IEEE Transactions on Industry Applications*, 25(4):732-737, 1989.

Holmes and Morgan, "Micro total analysis systems 2002," Proceedings of the μTAS 2002 Symposium, Nara, Japan, Nov. 3-7, 2002.

TriPath Care Technologies, http://www.tripathimaging.com, printed Aug. 28, 2002.

American Society of Cytopathology, "Cervical cytology practice guidelines," http://www.cytopathology.org/guidelines/guide_cervical_cytology.php, printed Aug. 28, 2002.

* cited by examiner

METHODS AND APPARATUS FOR ELECTROSMEAR ANALYSIS

Priority is claimed to (a) U.S. provisional patent application Ser. No. 60/435,938 filed Dec. 20, 2002 and (b) U.S. provisional patent application Ser. No. 60/475,717 filed Jun. 4, 2003. Both of those applications are incorporated by reference in their entirety.

BACKGROUND OF THE INVENTION

1. Field of the Invention

The present invention relates generally to analysis such as cytopathology and more particularly to methods and apparatus for utilizing dielectrophoresis (DEP) to achieve improved analysis techniques such as cytopathology techniques. Even more particularly, the present invention provides for the generation of segregated analysis smears that can be used in cytopathology and other applications (which the inventors have coined "electrosmears" or "electrosmear cytopathology").

2. Background

Cytology slides are prepared to screen and diagnose cellular samples taken from, for example, tissue samples, samples from the uterine cervix, urine, sputum, blood, fine needle aspiration biopsy, urethral, bronchial brushings and washings, cerebral spinal fluid, and other body fluids. The reliability and efficacy of the screening methods of these slides are measured by their ability to diagnose infections, precancerous lesions or cancerous lesions while at the same time avoiding false positive or negative diagnosis. The reliability of these slides is a primary issue. Often, the results are not accurate or are unreadable. Thus, there is a constant effort to improve the reliability and efficacy in the preparation of cytology samples.

One of the most common uses of cytology slides is for screening and diagnosis of a cervical sample. Carcinoma of the cervix is one of the most common malignancies in women, causing thousands of deaths per year in the United States. A large proportion of these cases are associated with absent or deficient screening, and many screening failures are the result of errors in cervical sampling or smear interpretation.

Screening for precancerous or cancerous changes of the uterine cervix traditionally involves microscopic assessment of cervical Papanicolaou smears, called Pap smears. This traditional method for screening requires scraping a woman's cervix with a sampling device, such as a cotton applicator stick, spatula or brush, and smearing this sample onto a slide for review by a medical lab professional. The specimen is gently spread across a slide to evenly distribute the cell sample. On the slide itself, cells of interest do not necessarily follow any recognizable geometrical arrangement; rather, they are arranged randomly. In other words, (a) it just as likely that a precancerous cell may be found near the center of the slide versus near the left end of the slide versus near the right end of the slide and (b) cells of interest are not necessarily grouped together or separated from other groups of cells for easy identification. Following the formation of the smear, the slide is fixed, stained, and examined under a light microscope for cellular abnormalities.

In carrying out this operation, the portion of the sample that is smeared onto the slide may contain blood, mucus, inflammatory cells, and clumps of cells. Accurate interpretation of up to 40% of conventional Pap smears are compromised by the presence of blood, mucous, obscuring inflammatory cells, scant cellular material, and air-drying artifacts. The presence of these contaminants can obscure many of the cells, causing important precancerous lesions to be missed when the slide is reviewed at the lab or, alternatively, making the entire slide unreadable. Techniques that attempt to more effectively distribute matter within the sample onto a slide typically utilize spinning, which, although it improves screening somewhat, still yields a randomized, non-segregated distribution of cellular components.

Accordingly, one of the problems with conventional cytopathology techniques is the inability to create adequately segregated smears where cells of interest may be grouped apart from other cells. Because conventional smears are effectively random (i.e., the cells of interest do not necessarily follow any recognizable grouping or segregation pattern), important features of the sample may be obscured and/or completely overlooked. This overlooking of features may, in turn, lead to deficient screening. When a clinician is presented with a conventional, randomly-distributed smear, it may be difficult to effectively analyze that sample. In particular, analyzing a sample having a randomized distribution would be more difficult and time-consuming than analyzing a sample whose cells of interest were grouped together, apart from other less important cells.

Another problem with the conventional Pap smear is the frequent inaccuracy of the test result. Common inaccuracies include both false positive and false negative Pap test results. A false positive Pap test occurs when a patient is told she has abnormal cells when the cells are actually normal. A false positive result may require a woman to undergo unnecessary and costly medical procedures. A false negative Pap test result occurs when a specimen is called normal, but the woman has a lesion. A false negative Pap test may delay the diagnosis and treatment of a precancerous or even a cancerous condition.

The conventional Pap smear has false negative rates ranging from 10–50%, with up to 90% of those false negatives due to limitations of sampling or slide preparation. To decrease false negative rates associated with interpretation error, re-screening a portion of the negative smear or recalling the patient for another sample is often required.

Concern over the frequency of false-negative results of the traditional Pap smear has led to the development of a variety of other technologies or clinical strategies, such as liquid-based cytology systems, to improve Pap testing. For example, the Cytyc, Inc. (Marlborough, Mass.), ThinPrep® and the TriPath, Inc. (Burlington, N.C.), CytoRich® Pap test systems are two commercially available, FDA approved fluid-based methods used for the collection and preparation of cervicovaginal samples.

With the ThinPrep® system, a gynecologic sample is collected in the same manner as the conventional Pap test using a broom-type device or plastic spatula and endocervical brush combination, but rather than smearing the cytological sample directly onto a microscope slide, this method suspends the sample cells in a fixative solution (i.e. PreservCyt®). The ThinPrep® slide preparation system uses an automated apparatus called a Cytyc 2000® that involves filtration using vacuum pressure and positive pressure-transfer steps to prepare cytology slides.

With the CytoRich® slide preparation system, the gynecologic sample is also collected in the same manner as the conventional Pap test. Like the ThinPrep® system, the CytoRich® system also places the sample in a liquid medium for further purification prior to analysis. CytoRich® specimens are processed using two centrifugation steps through a gradient solution to separate the diagnostic cells from the interfering material. The cells are ultimately resuspended in a final preparation that is applied to the slide using a special pipetting apparatus (Autocyte Prep System®) provided by the manufacturers (Tripath, Inc.). This transfer step can also be performed manually. Thereafter, a sample is placed on a slide and analyzed by cytology.

These new methods have demonstrated increased quality in the preparation of the sample, improved detection rates, and a reduced need for patients who must return for repeat smears. However, in both the ThinPrep® and the CytoRich® slide preparation systems, a time consuming and expensive procedure is followed to prepare a mono-dispersed layer of cells on a cytology slide. Additionally, despite their improvements, these systems are still not able to provide segregated smear samples, the presence of which would lead to more effective screening techniques.

In other cytological analyses, it is important to identify small numbers of diagnostically indicative cells within an overwhelmingly large concentration of background cells. For example, tumor cells may occur as a highly rarified subpopulation dispersed amongst normal cells in peripheral blood at concentrations below 1 tumor cell per $10^6$ nucleated blood cells. Similarly, rarified tumor cells may occur amongst lymph and blood cells in biopsies taken from lymph nodes proximal to a tumor. Such cells are of importance to the detection, prognosis and treatment of cancers. Also, the peripheral blood of a pregnant woman contains a very small concentration of fetal cells. Isolation and analysis of these can facilitate the identification of fetal status without the need for potentially risky in utero biopsy procedures. In other cases, disease states may be associated with a very small concentration of yeast, viral or bacterial cells mixed with blood, sputum, urine, or other suspensions of cells and particulate debris. Banding and identification of such pathogens, which is not offered by conventional cytopathology techniques, is of profound importance to disease diagnosis.

As an additional example, biowarfare agents may be present against a background of other cells types such as blood, yeast, harmless bacteria or viruses as well as of debris and particulates including smoke, dust, pollen and other matter. The isolation and identification of such biowarfare agents is of importance to detecting acts of biological warfare and terrorism. The concentration, isolation, and analysis of rare subpopulations of such exemplary cell types and of others are of fundamental importance to both research, clinical practice, agriculture, and defense. However methods to capture rare cells in well-defined locations of a slide where they may be stained, readily identified, and analyzed by a pathologist or through scanning cytometry using, for example, staining, histochemical, and molecular methods, are lacking.

In some cases, the total number of cells in a sample may be very small and the use of conventional methods to prepare slides may result in significant sample loss as well as slides having such a widely dispersed distribution of indicative cells that the slides may be of poor diagnostic value. Methods that can capture very small numbers of cells from small samples within concentrated, well-defined, and precisely located bands are therefore desirable but lacking in conventional cytopathology techniques. Such methods would also be of important use as adjuncts to other cell sorting or fractionation methods in which defined cell subpopulations need to be captured and analyzed with minimal sample loss.

In sum, conventional cytopathology systems suffer from several shortcomings, one of the most prevalent being the inability to generate a segregated smear having distinct groupings of cells so that a clinician may better analyze the sample and provide quick, accurate, reliable screening and/or diagnosis.

The referenced shortcomings are not intended to be exhaustive, but rather are among many that tend to impair the effectiveness of previously known techniques concerning cytopathology; however, those mentioned here are sufficient to demonstrate that methodology appearing in the art have not been altogether satisfactory and that a significant need exists for the techniques described and claimed in this disclosure.

SUMMARY OF THE INVENTION

Particular shortcomings of the prior art are reduced or eliminated by the techniques discussed in this disclosure.

In one respect, the invention involves a method for preparing a smear for cytopathology. Particles of a sample are subjected to a dielectrophoretic force to segregate and attach the particles into two or more zones of a surface.

In another respect, the invention involves a method in which particles of a sample are subjected to a dielectrophoretic force to segregate the particles into two or more zones of a surface. Those particles are then attached to the surface, thereby defining a segregated smear. The segregated smear is then fixed and stained.

In another respect, the invention involves a method in which a dielectrophoretic force is applied to particles of a sample to displace the particles to different positions within a velocity profile, thereby segregating the particles. The segregated particles are then attached to a surface, thereby defining a segregated smear.

In another respect, the invention involves a method in which programmed voltage signals of different frequencies are simultaneously applied to electrodes to subject particles of a sample to a dielectrophoretic force. The particles are segregated into two or more zones of a surface and then attached to the surface, thereby defining a segregated smear.

In another respect, the invention involves an apparatus for preparing a smear for cytopathology. The apparatus includes a dielectrophoretic field flow fractionator and a dielectrophoretic collector. The dielectrophoretic field flow fractionator is configured to subject particles of a sample to a dielectrophoretic force to segregate the particles into two or more zones. The dielectrophoretic collector is coupled to the fractionator and is configured to subject the particles to a dielectrophoretic force to attach the particles to a surface.

In another respect, the invention involves a kit in a suitable container for preparing a smear for cytopathology. The kit includes a surface including an array of electrodes adapted to subject particles of a sample to a dielectrophoretic force to segregate the particles into two or more zones, one or more fixing agents, and one or more staining agents.

As used herein, "particles" means any discernible component of a sample. In a preferred embodiment, "particles" refers to cells within a sample.

As used herein, "attach" means to secure, at least temporarily. Attachment to a surface may arise, in one embodiment, simply through gravitational or sedimentation force while in other embodiments it may be assisted by an adhesive, additional forces, etc. As used herein, "fix" is to be given its ordinary meaning in the art—e.g., a process that preserves the structure of a sample and prepares it for future treatment.

Other features and associated advantages will become apparent with reference to the following detailed description of specific embodiments in connection with the accompanying drawings.

BRIEF DESCRIPTION OF THE DRAWINGS

The techniques of this disclosure may be better understood by reference to one or more of these drawings in combination with the detailed description of illustrative embodiments presented herein. Identical or similar elements use the same element number. The drawings are not necessarily drawn to scale.

DESCRIPTION OF ILLUSTRATIVE EMBODIMENTS

Cytopathology techniques of the present disclosure address several shortcomings existing in the prior art such as those discussed above. In particular, the techniques provide ways to prepare a smear for cytopathology that is segregated—i.e., cells are grouped in a way to aid analysis. The segregated smear is brought about by utilizing dielectrophoretic forces on the sample being analyzed.

Figure 1:
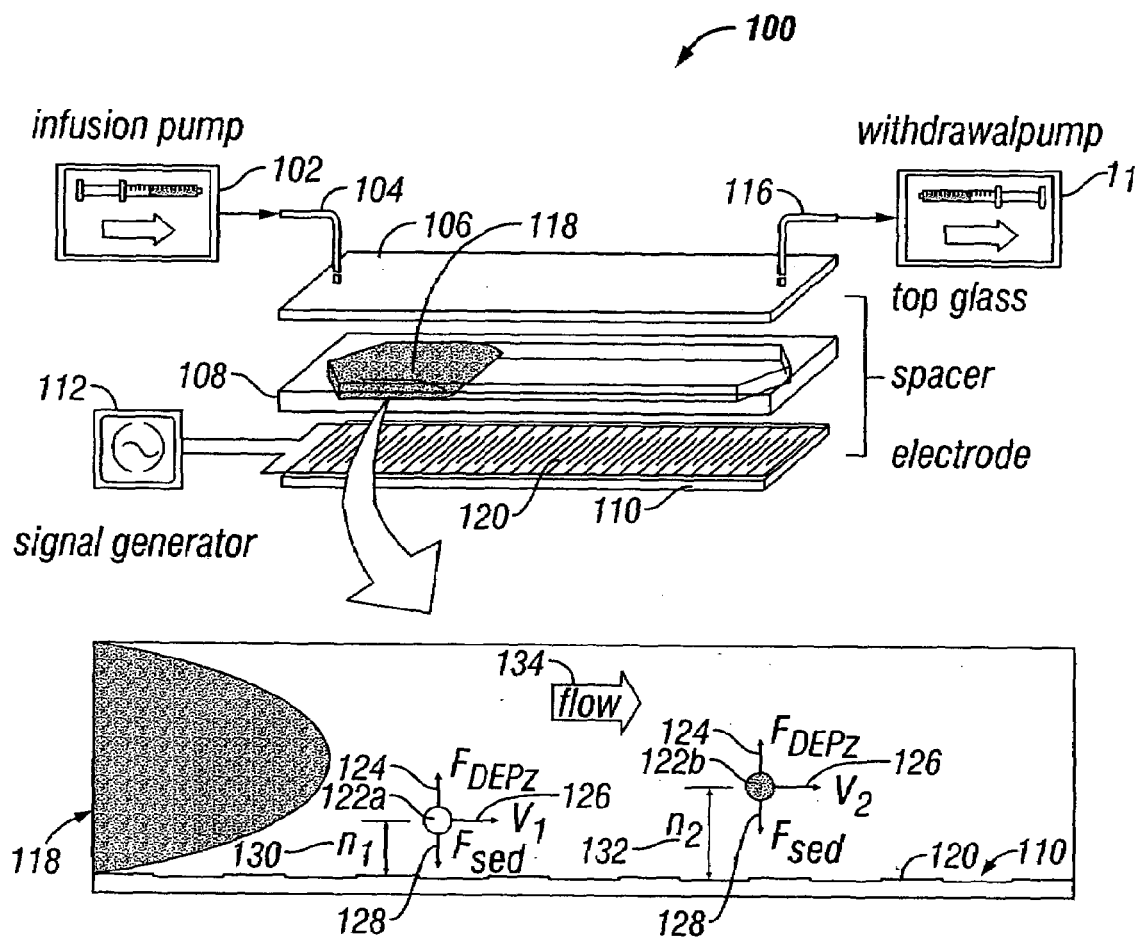
FIG. 1 includes a perspective and side-view schematic diagram of an apparatus for preparing a smear for cytopathology, according to embodiments of the present disclosure.

A representative embodiment of an apparatus for preparing a smear for cytopathology is illustrated in FIG. 1. Shown in the top half of FIG. 1 is an infusion pump 102, an infusion pump conduit 104, a top wall 106, a spacer 108, a surface 110, a signal generator 112, a withdrawal pump 114, a withdrawal pump conduit 116, a flow profile 118, and an electrode 120.

In one embodiment, operation of the apparatus 100 is as follows. Cells of a sample are placed upon surface 110. Those cells are subjected to a carrier medium that may be introduced via infusion pump 102 and infusion pump conduit 104. Spacer 108 provides the separation between top wall 106 and surface 110 required for the carrier medium to flow within the apparatus 100. The introduced carrier medium establishes a flow profile 118. In a preferred embodiment, the flow profile 118 exhibits higher velocities near its center as compared to its edges. Cells of the sample are subjected to a dielectrophoretic (DEP) force generated by signal generator 112 and electrode 120.

In one embodiment, a negative (upward from electrode 120 towards top wall 106) dielectrophoretic force may first be applied using electrode 120 so that cells are effectively levitated within the velocity profile to a height characteristic of dielectric properties of the cell. Specifically, an inhomogeneous field created by way of signal generator 112 may be controlled (i.e., through appropriate voltages, frequencies, pulse shapes, and the like) so that a negative dielectrophoretic force balances a gravitation (sedimentation) force or any other downward-directed force(s), to levitate cells to different heights.

Depending on their characteristic levitation height, cells travel faster or slower within flow profile 118. In particular, cells levitated near the center of the flow profile will travel faster than cells levitated near the top or bottom of the profile. Accordingly, cells are separated (in time and space) due to difference in dielectric properties. Hence, the cells are segregated.

Once the cells are segregated, a positive (downward towards electrode 120 away from top wall 106) dielectrophoretic force may then be applied using electrode 120 so that cells are effectively attached onto surface 110. Carrier medium 118, flowing in the flow profile 118, may be swept away and withdrawn via withdrawal pump conduit 116 and withdrawal pump 114.

Alternatively, cells may be effectively attached on surface 110 by removing (or reducing) dielectrophoretic forces and allowing cells to settle onto surface 110, which may include an adhesive or an attachment agent. In one embodiment, surface 110 may be coated with a material such as polylysine to aid in adhesion. In other embodiments, different materials, attachment agents, or adhesives known in the art may be used.

The bottom half of FIG. 1 illustrates many of these concepts. There, flow profile 118 is shown, and one can see that the center of the profile has a higher flow velocity, as exhibited by the different lengths of the arrows representing flow velocity. As shown by arrow 134, flow in this figure is from left to right. In the figure, two cells—122a and 122b—are shown, each being subjected to a negative dielectrophoretic force 124. As, illustrated, the negative dielectrophoretic force balances a downward sedimentary force 128 to effectively levitate the cells to characteristic heights 130 and 132. Heights 130 and 132 are different because the two cells differ in dielectric properties. Cell 122a levitated at height 130 will travel slower within flow profile 118 than will cell 122b levitated at height 132. This is true because height 132 is nearer the center of flow profile 118. Accordingly, at a given time, cell 122b will be farther to the right of cell 122a, as is illustrated. Hence, segregation occurs.

Following sufficient segregation, signal generator 112 may be appropriately adjusted (e.g., voltages and frequencies changed to effect a change in inhomogeneous fields) so that a positive dielectrophoretic force (not illustrated) is applied to cells 122a and 122b. In the presence of a strong positive dielectrophoretic force, the cells are attached to surface 110, effectively "frozen" in place. In the meantime, the carrier medium exhibiting flow profile 118 may be removed via withdrawal pump conduit 116 and withdrawal pump 114, leaving cells 122a and 122b behind to be analyzed.

In different embodiments, the application of a positive dielectrophoretic force may be performed at once or in stages as a function of time. Specifically, a positive dielectrophoretic force may be applied to entire surface 110 at once or, alternatively, a positive dielectrophoretic force may first be applied to one region of surface 110 and then to another according to an arbitrary or pre-programmed function of time. In one embodiment, positive dielectrophoretic force is first applied to a "far" end of surface 110 and then progressively inward until a positive dielectrophoretic force covers the entire surface 110. Specifically, with reference to FIG. 1, a positive dielectrophoretic force may first be applied to the far-right end of surface 110. Application of this force attaches the fastest-moving cells. As the force is applied inward, the slower-moving cells are also attached to the surface 110. Different functions of time may be applied to maximize or tailor the segregation properties of the cells as desired.

For instance, in one embodiment, multiple electrodes 120 may be coupled to a signal generator 112 that activates electrodes 120 at appropriate times to attach specific sample fractions in specific locations on the surface 110. In particular, in one embodiment, a frequency f1 may be applied initially to N electrode segments in order to create a negative dielectrophoretic force that prevents trapping of cells or particles. After some elapsed time, based on the sample conditions, the signal generator 112 may switch the signal applied to an electrode segment most distal from the infusion pump conduit 104 to f2, a frequency higher than f1, that trap cells that are above that segment. During a second subsequent interval, cells arriving at that segment are also trapped there. After the second interval, the electrode segment next-closest to infusion pump conduit 104 may also be switched to frequency f2, trapping cells above it. This sequence of activation of electrode segments with the frequency f2 may continue until all electrode segments are activated with frequency f2. One advantage of this mode of operation is that the timing of the switching sequence need not be constant. Instead, each time interval in the sequence may be different so as to allow bands of cells to be compressed or expanded as desired for a particular cell preparation.

Advantageously, one may alter the field strength and/or frequency with time so as to compress diffuse bands of cells or to stretch narrow bands of cells into resolved components as desired in order to facilitate the acquisition of diagnostic data. In different embodiments, the following frequency-time scenarios may be useful.

FIGS. 23A–23D show some exemplary frequency-time profiles that are useful for distributing cells advantageously on a single-segment electrosmear.

Figure 23A:
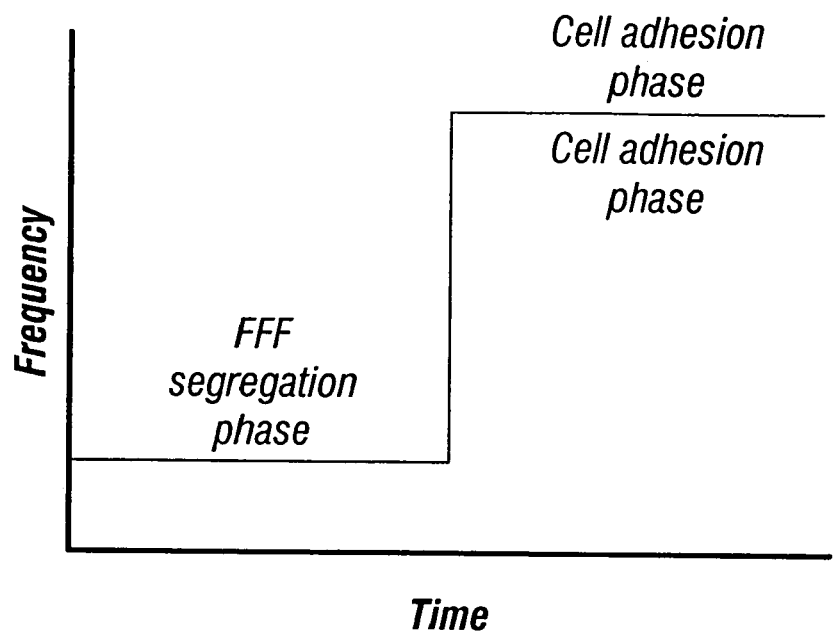
FIGS. 23A–23D show some exemplary frequency-time profiles that are useful for distributing cells advantageously on a single-segment electrosmear, in accordance with embodiments of the present disclosure.

FIG. 23A provides a frequency for dielectrophoretic/field flow fractionation (DEP-FFF) during which cells having different properties fractionate as they move over the electrodes, followed by a step to high frequency during which cells are settled onto the surface.

Figure 23B:
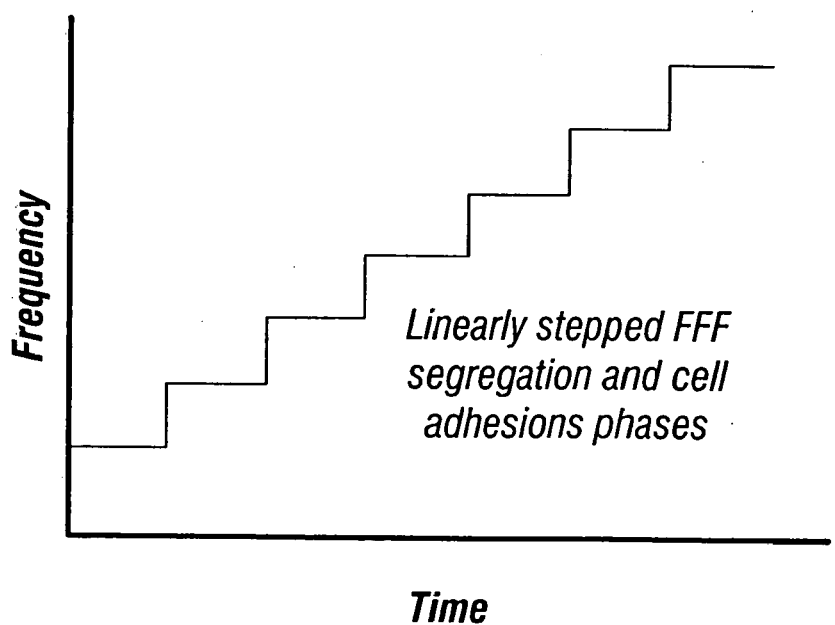

FIG. 23B provides several DEP-FFF and trapping phases. As each frequency step occurs, those cells having dielectric properties that no longer cause levitation settle and are attached on the electrosmear surface. Meanwhile, other cell types that are still levitated will continue to move over the electrode. As each frequency step occurs one or more cell subpopulations may be trapped.

Figure 23C:
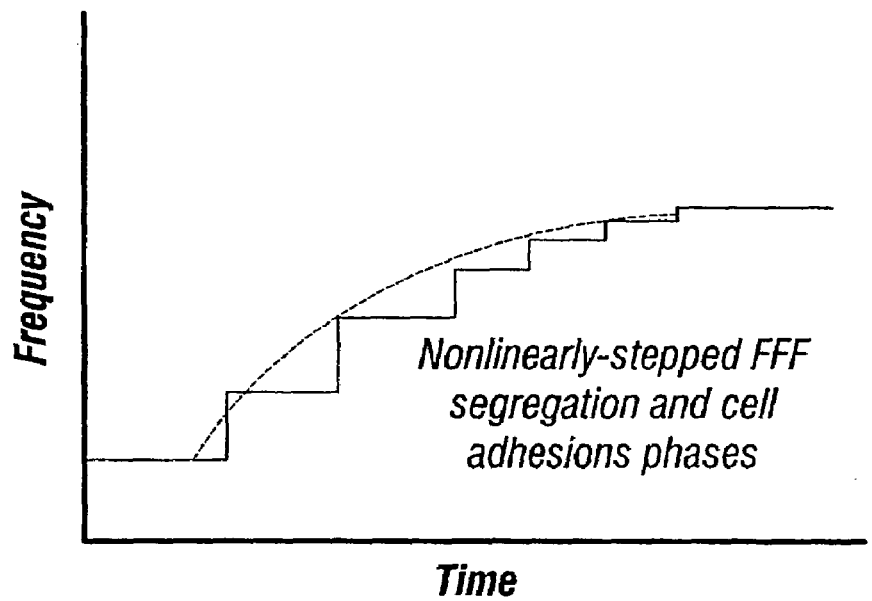

FIG. 23C also provides a stepped series of DEP-FFF and trapping phases; however, in this case, the frequency is stepped in smaller and smaller increments, increasing the discrimination between subsequent cell subpopulations that are trapped.

Figure 23D:
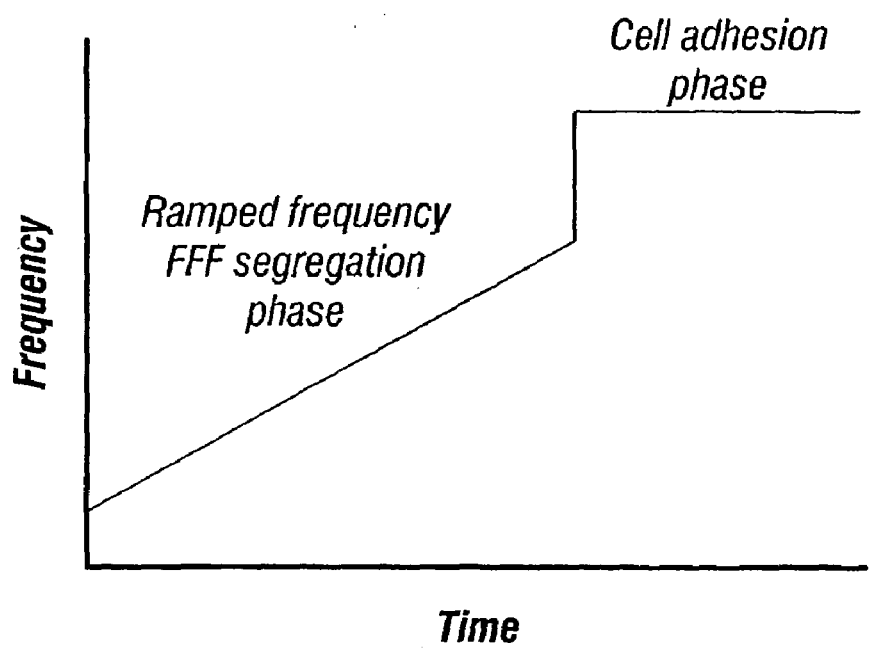
Figure 24A:
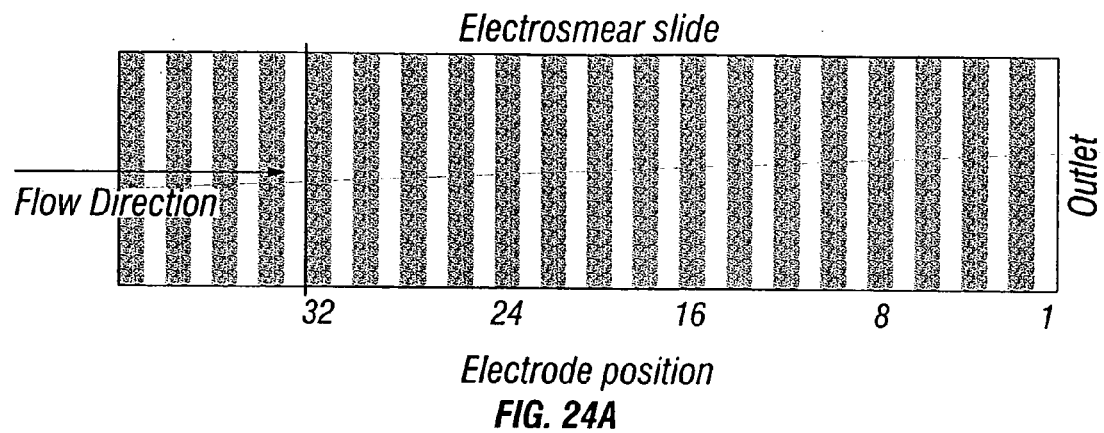
FIGS. 24A–E show segment-time profiles for an electrosmear for trapping cells eluting in a fractionator such as a DEP-FFF separator, in accordance with embodiments of the present disclosure.
Figure 24B:
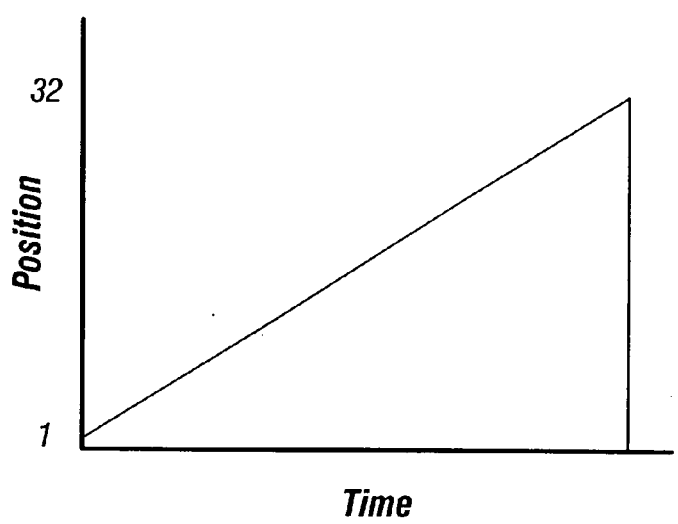
Figure 24C:
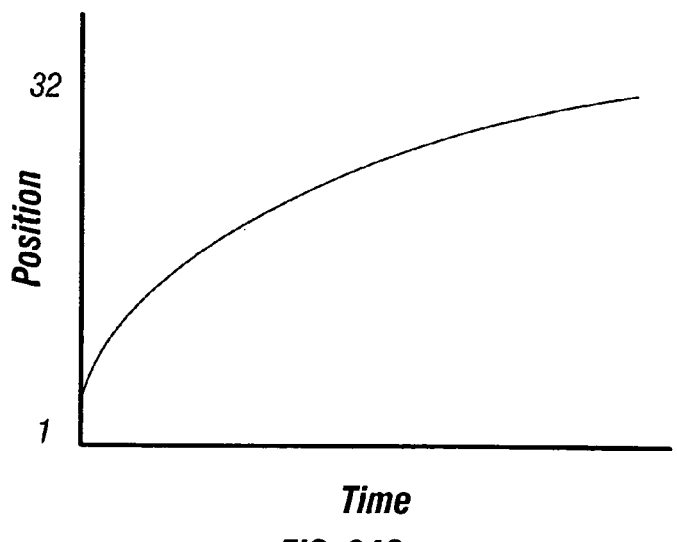
Figure 24D:
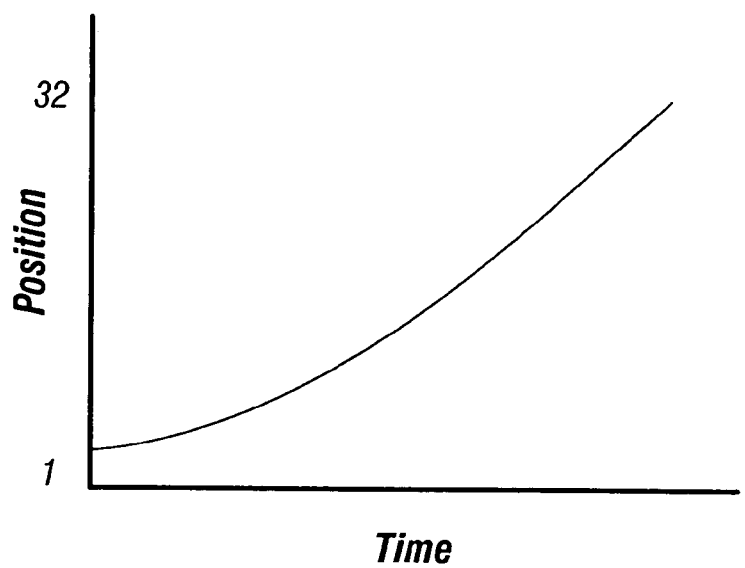
Figure 24E:
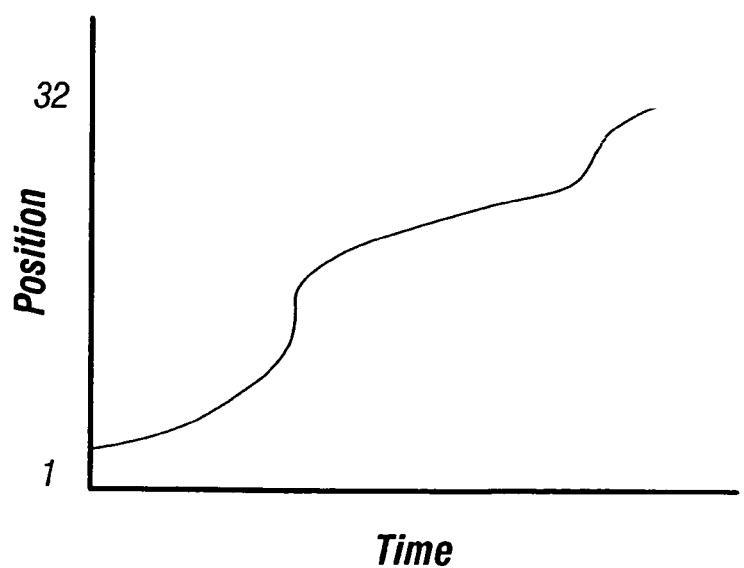

FIG. 23D shows a ramped frequency, whereby each cell type in the sample undergoes continuos DEP-FFF until the frequency rises to the point at which that type is no longer levitated.

The frequency-time profiles of FIGS. 23A–D are representative examples only and additional frequency-time profiles that are advantageous may be used, as will understood by one of ordinary skill in the art having the benefit of this disclosure.

FIGS. 24A–E show segment-time profiles for an electrosmear for trapping cells eluting in a fractionator such as a DEP-FFF separator. The top diagram (FIG. 24A) defines positions from the outlet end of the electrosmear. At any given time, the part of the electrode from position 0 up to and including the position shown in each profile is excited with a high frequency signal that will trap all cells. The illustrated profiles alter the relative positions at which different cell subpopulations are trapped. Convex regions of a profile tend to spread out cell subpopulations, offering higher discrimination between slightly different cells while concave regions tend to compress the smearing of slightly different cell types.

Rather than using positive dielectrophoretic forces to attach cells, one may alternatively attach cells onto surface 110 by removing (or reducing) dielectrophoretic forces and allowing cells to settle onto surface 110, which may include an adhesive or an attachment agent. For example, surface 110 may be coated with a material such as polylysine to aid in adhesion. In other embodiments, different materials, attachment agents, or adhesives known in the art may be used. In yet another embodiment, no adhesive may be used, and cells may simply be allowed to settle onto surface 110, later to be fixed and/or stained and analyzed as known in the art.

Figure 2:
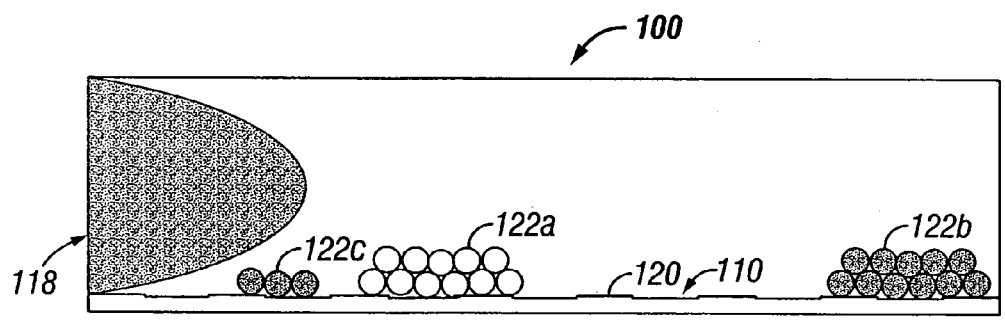
FIG. 2 is side-view schematic diagram showing cells segregated into zones of a surface, according to embodiments of the present disclosure.

FIG. 2 is side-view schematic diagram showing different cells segregated into zones of surface 110 to define a segregated smear. As illustrated, cells 122a, 122b, and 122c may be attached to surface 110 preferably by way of a positive dielectrophoretic force or alternatively by an appropriate adhesive (or simply through gravity). Because different cells are levitated at different characteristic heights, based on dielectric differences, the cells are separated (segregated) on the surface 110. In particular, cells 122b are furthest right, cells 122a are center, and cells 122c are left. Noting that flow profile 118 is from left to right, this means that cells 122b moved the fastest and hence had a levitation height nearest the center. Once affixed, flow profile 118 and its constituent carrier medium may be swept away.

Figure 3:
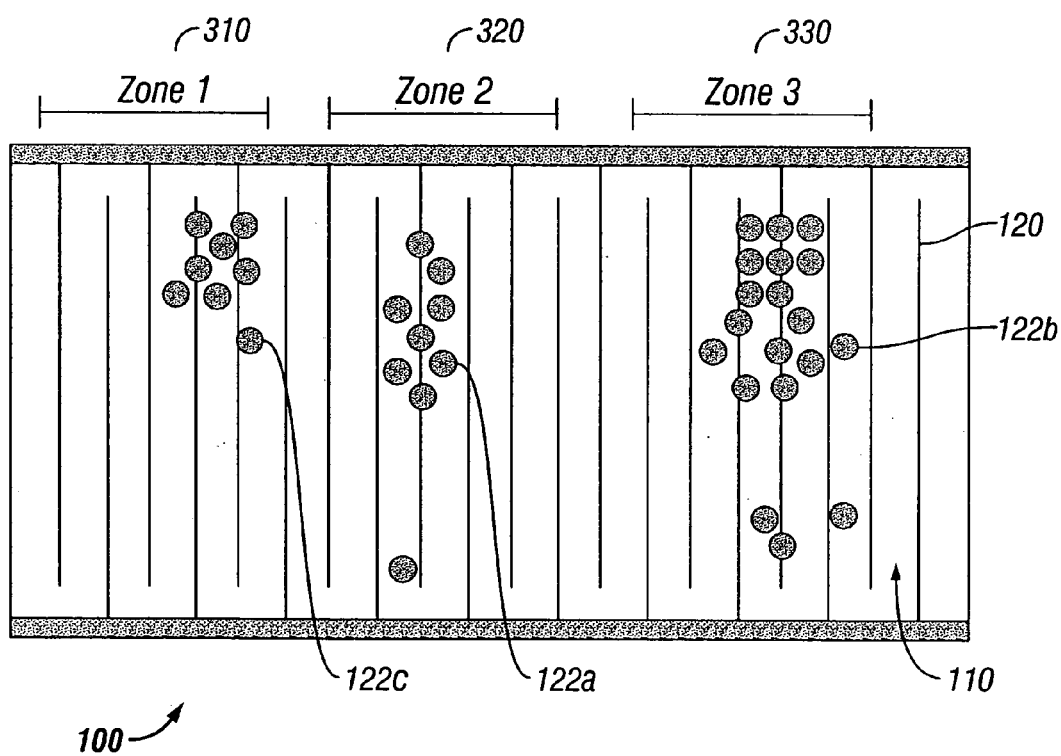
FIG. 3 is top-view schematic diagram showing cells segregated into zones of a surface, according to embodiments of the present disclosure. Three distinct zones are shown.

FIG. 3 is top-view schematic diagram showing a segregated smear. Cells 122c occupy a first zone 310. Cells 122a occupy a second zone 320. Cells 122b occupy a third zone 330. These zones are, of course, zones on surface 110.

The techniques described above to created a segregated smear may take place in a suitable chamber, as illustrated generally in FIG. 1. In particular, steps utilizing dielectrophoretic forces to segregate cells may occur in a chamber suited to accommodate carrier fluid, electrical connections to a signal generator, and the like. Once a segregated smear is formed within the chamber, the surface (which, in a preferred embodiment, may be akin to a microscope slide with attached electrodes) may be removed from the chamber. Once removed, the surface may be fixed and stained, as with conventional cytopathology samples.

In alternative embodiments, segregated smears may be formed in several other similar ways by using dielectrophoretic forces, as those having ordinary skill in the art will recognize with the benefit of this disclosure. For instance, in one embodiment, levitation may not be required, or levitation may be achieved using a force other than a negative dielectrophoretic force. In such an embodiment, dielectrophoretic force may be applied to sample cells such that cells of one type migrate, even slightly, from cells of another type. In this way, a segregated smear may be achieved. Further, in another embodiment, introduction of a carrier medium may aid this migration. Although it may not be necessary for the carrier medium to follow any particular flow profile, the carrier medium may, instead, simply lower the dielectrophoretic force required to migrate cells from one another by effectively providing a lubricating layer upon surface 110. In this regard, the reader is directed to U.S. Pat. No. 6,294,063, already incorporated by reference, that discusses techniques whereby packets of materials may be precisely moved using dielectrophoretic forces. In general, the present application contemplates any use of dielectrophoretic force to effect a segregation of cells upon a surface for preparing a cytopathology smear.

In yet another alternative embodiment, one may utilize electrode 120 of apparatus 100 of FIG. 1 to simultaneously (or nearly simultaneously) apply different dielectric fields of different frequencies to segregate cells into different zones onto surface 110. In this regard, the reader is directed U.S. Pat. No. 6,264,815 ("the '815 patent"), which is already incorporated by reference. The '815 patent discloses techniques in which different frequencies are used to test particles in a fluid. Although the '815 patent does not disclose or suggest the subject matter of the present claims, it is useful in explaining how different dielectrophoretic fields may be generated of differing frequencies. Following segregation, the cells may be attached to a surface by suitable techniques (such as through the application of positive dielectrophoretic force, adhesion, or simply sedimentation), fixed, and stained.

That a segregated smear is defined offers tremendous advantages over the prior art. In particular, with segregated smears, it is less likely that cells of one type will obscure cells of another type, since cells may be grouped together distinctly from one another. More importantly, perhaps, is the advantage afforded to the clinician by the fact that dielectrophoretic forces can be used to effectively segregate different cells based on, for instance, their propensity towards cancerous states or other disease or pre-disease states. For instance, the reader is directed to U.S. Pat. No. 6,287,832, already incorporated by reference, which discusses work in which cancerous cells are separated from normal cells using dielectrophoretic segregation techniques. Because dielectrophoresis can segregate such differences, the clinician may simply scan for characteristic groupings of cells (within certain zones) upon a smear rather than meticulously searching the entire smear hoping to come across one or more cells of interest that may reside anywhere on the surface.

Once a segregated smear is formed upon surface 110, one may fix the smear using any fixation agent known in the art. As known, the use of fixation agents prevents deleterious effects caused by the drying of samples. Fixation may be mediated through the use of molecules linked to the surface that chemically or physically interact with the cells. For example, the surface may include a coating of polylysine, integrins, antibodies, probes, ligands, hydrophobic or hydrophilic agents, or any other agents that interact with the cells and cause them to be captured. Fixation in such a manner stabilizes the distribution of the cells in the smear so that it may be processed by additional analytical methods, removed, and stored. Chemical fixation of the cells to stabilize their internal structure may also be accomplished following segregation by, for example, air drying, and/or treatment with an aldehyde, alcohol, or other agent.

One may treat a segregated smear with one or more stains or contrast agents known in the art in order to allow the enhanced visualization of cellular characteristics and structure. For example, Wright, Wright-Gimsa, Papadopoulous, other dyes, histochemical, enzyme-linked staining, antibody, or molecular-specific staining, may be used to enable the cell identification and the analysis of cellular structures and functions.

If desired, cells may be held in position by dielectrophoretic forces during the fixation and/or staining steps. In embodiments using a chamber, this allows all aspects of slide preparation to be accomplished without disassembly of the electrosmear chamber and any associated risks of losing cells.

Figure 4:
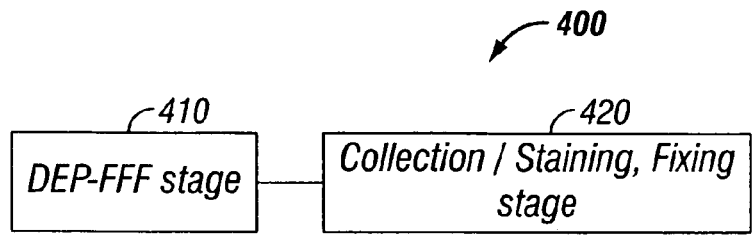
FIG. 4 is schematic block diagram of an apparatus for preparing a smear for cytopathology, according to embodiments of the present disclosure. Shown is a dielectrophoretic field flow fractionator coupled to a dielectrophoretic collector.

FIG. 4 is schematic block diagram of an apparatus 400 for preparing a smear for cytopathology. Shown is a dielectrophoretic field flow fractionator 410 coupled to a dielectrophoretic collector 420.

Field flow fractionator 410 is configured to subject cells of a sample to dielectrophoretic force to achieve segregation, as described in any of the embodiments above. In one embodiment, the segregation may be achieved by controlling an inhomogeneous field to create a negative dielectrophoretic force suitable to balance with a gravitational force to levitate cells to characteristic levitation heights, as described above. Dielectrophoretic collector 420 is configured to attach the segregated cells onto a surface to create different zones of the segregated smear. In one embodiment, this attachment may be brought about by application of a positive dielectrophoretic force to effectively freeze cells in place, although other techniques suitable for attachment may be used.

In one embodiment, dielectrophoretic field flow fractionator 410 may be integral with dielectrophoretic collector 420, as is the case with apparatus 100 of FIG. 1. In another embodiment, the two modules may be separate and may be coupled through any means suitable to transfer cells from one module to another. In yet another embodiment, dielectrophoretic collector 420 may also serve as the site for fixation and/or staining of a segregated smear. In particular, once cells are attached onto a surface (in different zones), a technician may apply a fixing agent and/or a stain directly to the surface. In other embodiments, however, fixing stages and staining stages may be separate.

Figure 5:
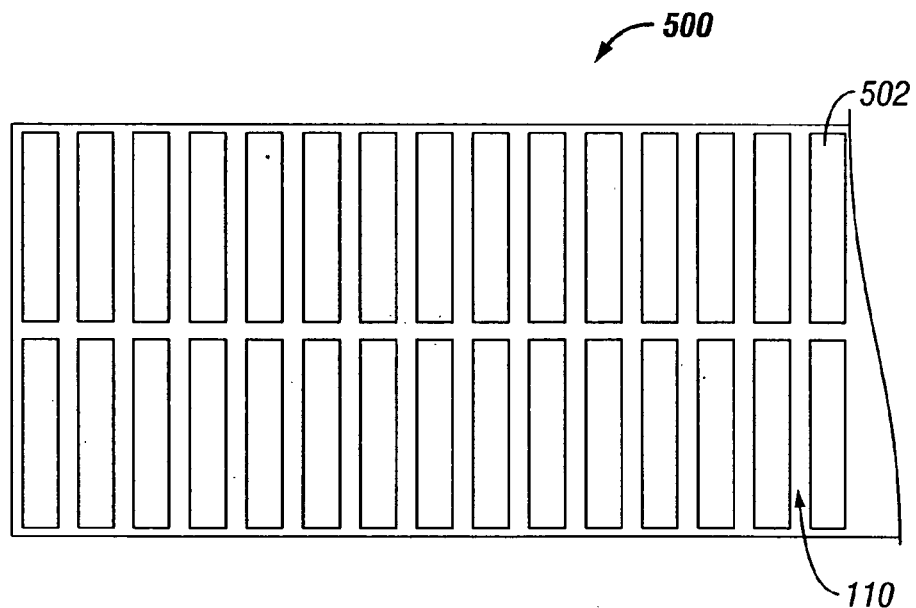
FIG. 5 is schematic block diagram of an integral dielectrophoretic collector, fixing stage, and staining stage, according to embodiments of the present disclosure.

FIG. 5 is schematic block diagram of an apparatus 500, which is an integral dielectrophoretic collector, fixing stage, and staining stage. Apparatus 500 includes electrodes 502 coupled to surface 110. What FIG. 5 illustrates is that electrodes 502 may be similar to, or different from, electrodes used within dielectrophoretic field flow fractionator 410 of FIG. 4. For instance, electrodes 502 may be sized differently or made from different material so that they are specifically designed only for the generation of quick, large, positive dielectrophoretic forces to freeze sample cells into place. Because the apparatus 500 may also serve as a fixing and/or staining stage, surface 100 may be coated appropriately. In one embodiment, apparatus 500 may even be disposable to allow technicians to easily dispose of samples following use. In such an embodiment, surface 110 and electrodes 502 may be part of a flexible sheet of electrodes that could be pre-sized or cut to size according to need. In this regard, even apparatus 100 of FIG. 1 may be made disposable as well through the use of inexpensive electrode materials.

Figure 6:
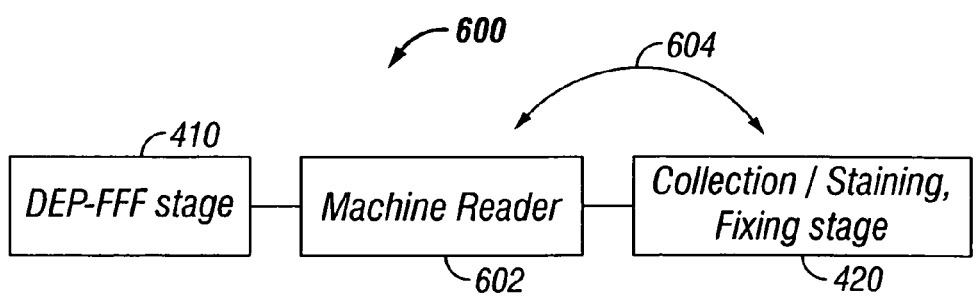
FIG. 6 is schematic block diagram of an apparatus for preparing a smear for cytopathology, according to embodiments of the present disclosure. Shown is a dielectrophoretic field flow fractionator coupled to a machine reader coupled to a dielectrophoretic collector.

FIG. 6 is schematic block diagram of an apparatus 600 for preparing a smear for cytopathology. Shown is a dielectrophoretic field flow fractionator 410 coupled to a machine reader 602 coupled to a dielectrophoretic collector 420. FIG. 6 is identical to FIG. 5 except for the addition of machine reader 602. Machine reader 602 is a device that is configured to image and/or analyze segregated smears according to the embodiments described herein. As denoted by arrow 604, machine reader 602 may be coupled in-between dielectrophoretic field flow fractionator 410 and dielectrophoretic collector 420 or to dielectrophoretic collector 420. In other words, machine reader 604 may analyze the output from dielectrophoretic field flow fractionator 410 or from dielectrophoretic collector 420. In the case of an integrated apparatus such as apparatus 100 of FIG. 1, machine reader 620 analyzes the integrated output of the device. In one embodiment, machine reader 620 may be made integral with dielectrophoretic field flow fractionator 410 or dielectrophoretic collector 420 (or with an integrated device such as apparatus 100 of FIG. 1).

In operation, machine reader 602 may employ any imaging and/or analysis techniques known in the art to image, recognize, or characterize distinct samples. In one embodiment, machine reader 602 may simply provide the technician with an electronic display of a segregated smear. In another embodiment, machine reader 602 may recognize distinctive groupings of cells (via appropriate optical or pattern recognition techniques) to aid the technician in making an evaluation of the sample. In such an embodiment, one may utilize one or more impedance sensors to determine where upon the surface different groupings of cells lie. The reader is directed to U.S. Pat. No. 6,294,063, already incorporated by reference, for a discussion of the use of impedance sensors to track the locations of particles upon a surface. In yet another embodiment, machine reader 602 may employ fluorescence, reflectance, or any other type of spectroscopy to analyze a segregated smear to characterize cells appearing in different zones on the surface. In yet another embodiment, machine reader may electronically simulate different dyes (i.e., create "virtual" dyes through appropriate electronic imaging techniques) to allow technicians to analyze samples without resort to physical dyes. In yet another embodiment, machine reader 602 may obviate the need for any fixing of a sample. Rather, a sample may be quickly analyzed before any drying effects take hold.

Figure 7:
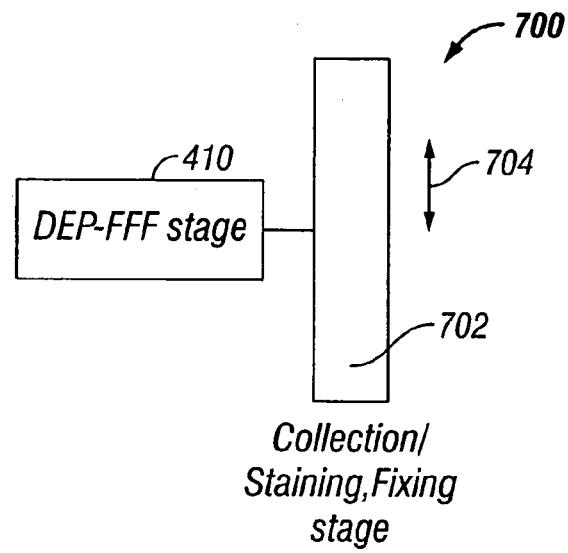
FIG. 7 is schematic block diagram of an apparatus for preparing a smear for cytopathology, according to embodiments of the present disclosure. Shown is a dielectrophoretic field flow fractionator coupled to a dielectrophoretic collector, which moves relative to the fractionator to create a segregated smear.

FIG. 7 is schematic block diagram of an apparatus 700 for preparing a smear for cytopathology. It includes dielectrophoretic field flow fractionator 410 coupled to collector 702. In this embodiment, collector 702 moves relative to dielectrophoretic field flow fractionator 410 as illustrated by arrow 704. In this embodiment, different cell groupings emerge from dielectrophoretic field flow fractionator 410 at different times. Because collector 702 is moving, different cell groupings are therefore "deposited" at different locations upon the collector. Dielectrophoretic collector 702 may utilize dielectrophoretic force to attach the emerging cells to its surface. Alternatively, any other form of force (including adhesion or the like) may be used to ensure that, once deposited, the cell groupings stay in place. In one embodiment, the apparatus 700 may be arranged such that collector 702 simply uses gravity to ensure that cell samples stay in place.

Figure 8:
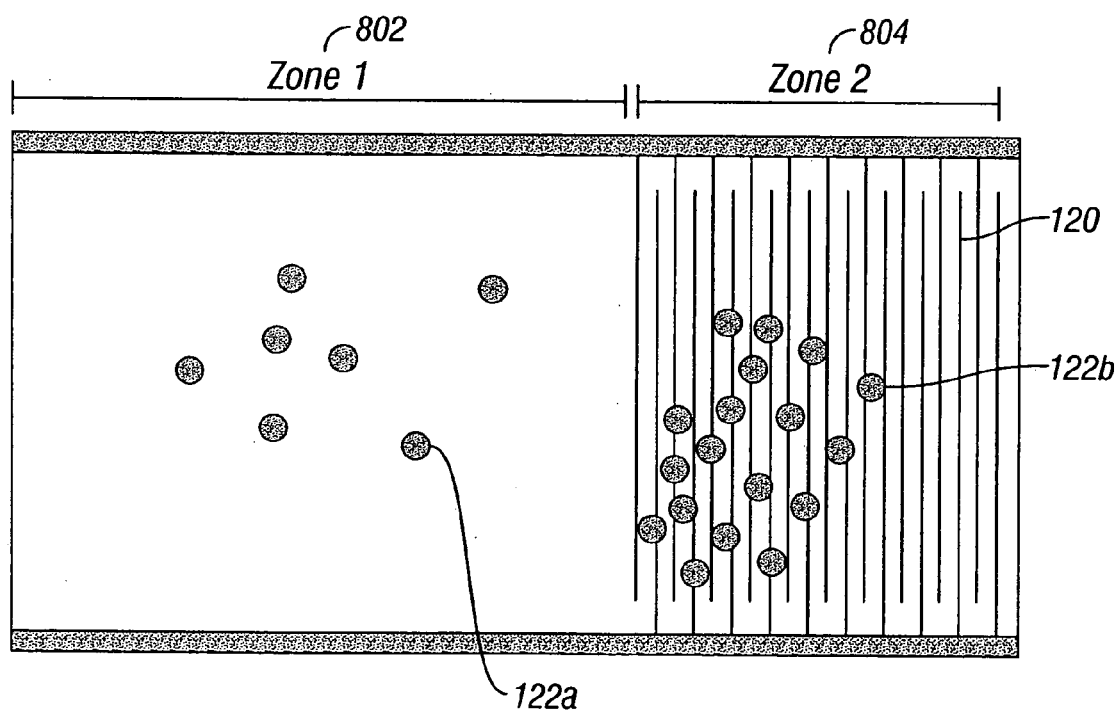
FIG. 8 is top-view schematic diagram showing cells segregated into zones (two zones are shown) of a surface, according to embodiments of the present disclosure. Electrodes cover only a portion of the surface.
Figure 9:
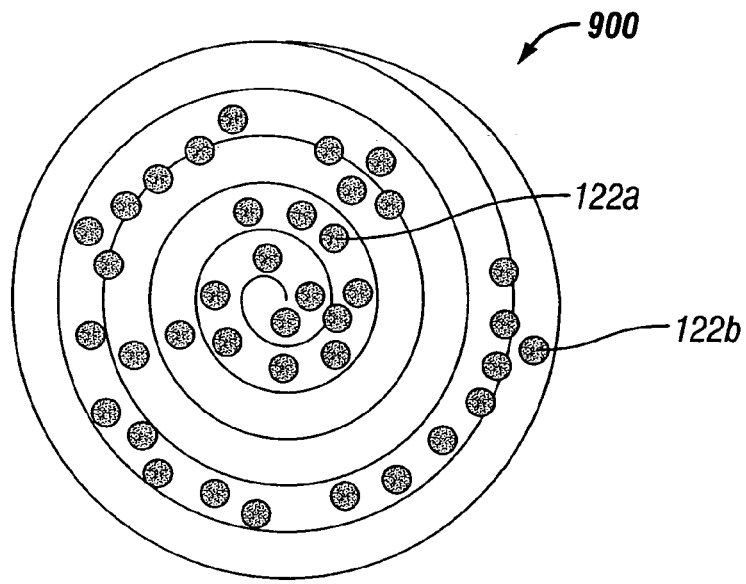
FIG. 9 is top-view schematic diagram showing cells segregated into concentric zones (two zones are shown) of a surface, according to embodiments of the present disclosure. A spiral electrode is used.

FIGS. 8 and 9 are schematic diagram showing cells segregated into zones (two zones are shown) of a surface. FIG. 8 illustrates that electrodes need not cover an entirety of a surface to generate a segregated smear. In the illustrated embodiment, electrodes 120 cover only a portion of the surface. However, segregation still takes place—cells 122a are segregated into zone 1 (element 802) while cells 122b are segregated into zone 2 (element 804).

FIG. 9 illustrates that different types of electrodes may be used in conjunction with the techniques of this disclosure. In FIG. 9, spiral electrode 900 is used to segregate a smear into two different concentric zones. Cells 122a occupy an inner zone while cells 122b occupy an outer zone.

Figure 10:
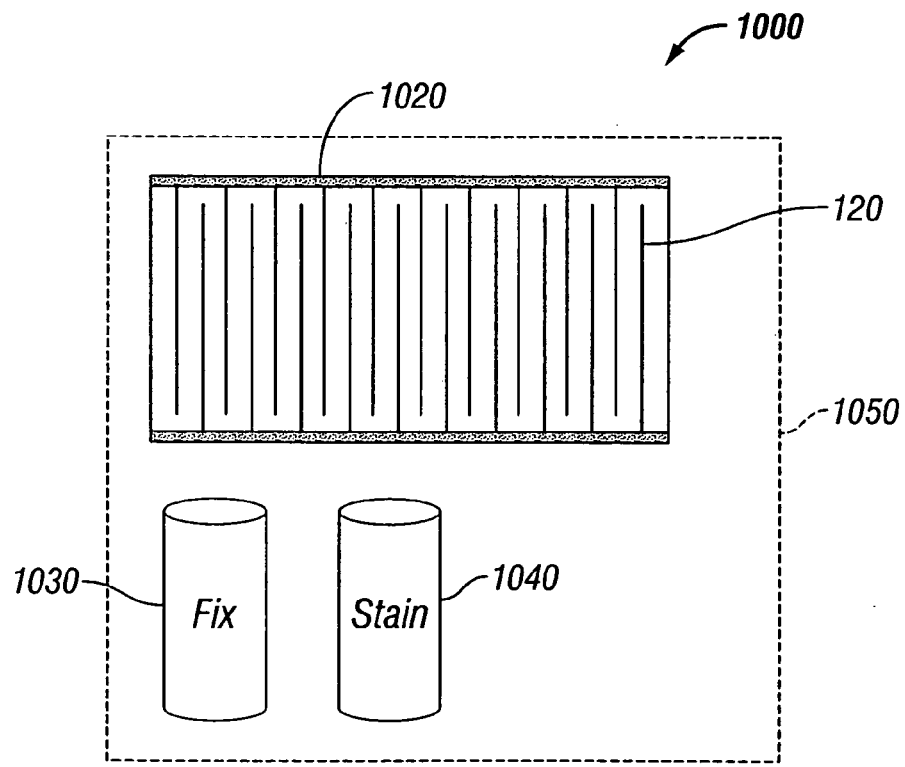
FIG. 10 is a schematic diagram showing a kit for preparing a smear for cytopathology including a surface having electrodes, fixing agent(s), and staining agent(s), according to embodiments of the present disclosure.

FIG. 10 is a schematic diagram showing a kit for preparing a smear for cytopathology. Shown is an integral apparatus 1020 including electrode 120 useful for both creating a segregated smear, fixing it, and staining it all within one unit. Fixing agents 1030 and staining agents 1040 are also shown. These materials may all be placed in container 1050. In one embodiment, apparatus 1020 may be disposable. In other embodiments, different distinct units for segregation, fixing, and/or staining may replace apparatus 1020, as described herein. Further, appropriate electronic hardware such as a signal generator and/or attaching wires may be supplied within container 1050.

As used herein, "a" and "an" shall not be strictly interpreted as meaning "one" unless the context of the invention necessarily and absolutely requires such interpretation. For instance, in this application, mention is made of electrode 120. This is not to say, however, that the invention is limited to the use of a single electrode 120. To the contrary, electrode 120 may refer to an entire array of electrodes, as is the case in preferred embodiments and as shown in the figures. Such is the case for dielectrophoretic force 124. As will be understood by those of ordinary skill in the art, the force labeled as 124 may, depending on the dielectric properties of cells, be of different magnitude for each type of cell in a sample. Hence, although it may be termed "a" dielectrophoretic force 124, those of ordinary skill in the art will understand that the element number 124 may refer to more than one force, having different magnitudes (and/or direction). The same is true of the other forces shown in the figures. As used herein, "on" or "upon" shall not be strictly interpreted to require direct contact. For instance, a cell "on" a surface 110 contemplates that the cell and surface may be separated by an intermediate material.

The following examples are included to demonstrate specific, non-limiting embodiments of this disclosure. It should be appreciated by those of skill in the art that the techniques disclosed in the examples that follow represent techniques discovered by the inventors to function well in the practice of the invention, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the invention. For instance, it will be understood that this disclosure covers embodiments dealing with not only cells but also bacteria and particles in general. Additionally, techniques of this disclosure may be used in stand-alone configuration, with DEP-FFF, magnetic (MAG)-DEP-FFF, with FFF, generalized (gDEP)-FFF, and any other dielectrophoretic fractionation methods that can produce a segregated smear.

EXAMPLE 1

Polylysine Coating of Electrosmear Slides

Electrosmear slides were cleaned by dipping in Piranha solution (70:30 $H_2SO_4$: $H_2O_2$) for 2 minutes followed by washing in 3× distilled water until all residual Piranha solution was removed. Slides were then dried under $N_2$ stream and were processed immediately for coating. Polyl-ysine solution was prepared fresh by adding 35 ml. Poly-l-lysine (Sigma) and 35 ml. of PBS (TC grade) to 280 ml. of 3× distilled water. To each dish, 350 ml. of lysine solution was added and 4 slides were submerged and shaken gently for two hours in a shaker. Lysine solution was discarded and the slides were rinsed for 10–15 seconds in 3× distilled water. Slides were then either quickly spun dry in a centrifuge for 5 minutes or dried under $N_2$ stream. Coated slides were transferred immediately to a clean Petri dish and placed in 42° C. oven for 2–3 hrs or overnight at room temperature in the clean room for thorough drying until use.

Sample Preparation

Cultured HL-60, a breast cancer line (MDA435), and fresh blood cells were used in this experiment. Cultured cells were grown in RPMI and MEM medium supplemented with 10% fetal bovine serum, 1 mM glutamine, 20 mM HEPES, and 0.5% penicillin, and streptomycin solution, respectively. Leukocytes were prepared by one of the two methods. In one method, red blood cells from whole blood were preferentially lysed by 85 mOs sucrose/dextrose solution. We determined that the osmolality of 85 mOs lyse RBCs to 90–95% whereas white blood cells were unaffected. In another method, leukocytes were prepared simply by buffy coat procedure. No attempts were made to lyse the red blood cells. Both cultured cancer cells and blood cells were washed in a running buffer at appropriate conductivity and counted by Coulter counter before being used in the experiment. One hundred thousand to five hundred thousand cells were used for each experiment.

Electrosmear Experiment

Polylysine coated slide containing an array of parallel gold electrodes of 50 micron width and spacing was placed in an electrosmear chamber with dimension of 45 mm in length and 10 mm in width. The chamber was connected to a sequencer through two cables which activate the electrodes at appropriate times with the appropriate voltage and multi frequency to capture specific type of cell at specific locations on the electrosmear slide. The chamber was closed tightly using two clamps when the electrodes and the cables were aligned properly as indicated by two LEDs . This ensures that the electrode has connected properly to a multichannel frequency generator which could deliver up to 4 volts of power with a frequency range from 6 KHZ to 340 KHZ at 36 different segments along the length of the slide. Each segment has 10 electrodes and, in one embodiment, corresponds to a single frequency. In different embodiments, segments may share one or more frequencies. A digital syringe pump was used to provide a flow of carrier medium through the chamber at a rate of 100 µl/min. A sample injection valve allowed measured sample introduction from a 20 µl loop.

The electrosmear chamber was first filled with a buffer consisting of 8.5% (w/w) sucrose and 0.3% (w/w) dextrose at a conductivity between 10 ms/m to 56 ms/m. To ensure that no air bubbles were present at the chamber, the buffer was first degassed under vacuum for several minutes. A mixture of different cell types was introduced into the chamber. To accomplish this, the injection valve was first set in the "load" mode and 20 µl loop was filled with sample using a 1 ml. syringe. Twenty µl. of sucrose/dextrose buffer was pumped through the chamber by the syringe pump operating at 50 µl/min. The valve was next switched to the "injection" mode and 20 µl of buffer was pumped through the loop at the same rate to flush the sample into the chamber. The valve was next switched back to "load" position and the remaining 10 µl of buffer was pumped through the syringe.

After the sample had been loaded into the chamber, cells were allowed to relax for 5 minutes. Following relaxation, a flow of carrier medium was commenced using the syringe pump at a rate of 100 µl./min. As the mixture of cells started to flow through the chamber, they would be exposed to different frequency along their way. Based on their crossover frequency, each cell type would be trapped at different location on the slide as they traveled and thus separated from each other. Following, a total 2 ml. of buffer flowed through the chamber, and the slide was removed and dried immediately under $N_2$ stream or in air.

Staining of Slides

For identification of the cell type that has been captured on the slide, cells were first fixed and stained using Wright stain and then observed under microscope. In short, slides containing the trapped cells were first dipped into methanol for 10 seconds for quick fixing followed by dipping into solution II (containing eosin) and III (containing Methylene blue) for 20 and 30 seconds respectively. In order to have a deeper stain for the cells, slides could be dipped into solution II for longer time. Slide was then washed in 3× distilled water before taking a photograph under microscope.

Results

Human Blood Cells From Buffy Coat

Conductivity 10 ms/m; cell concentration $43 \times 10^6$ cells/ml.

Figure 11:
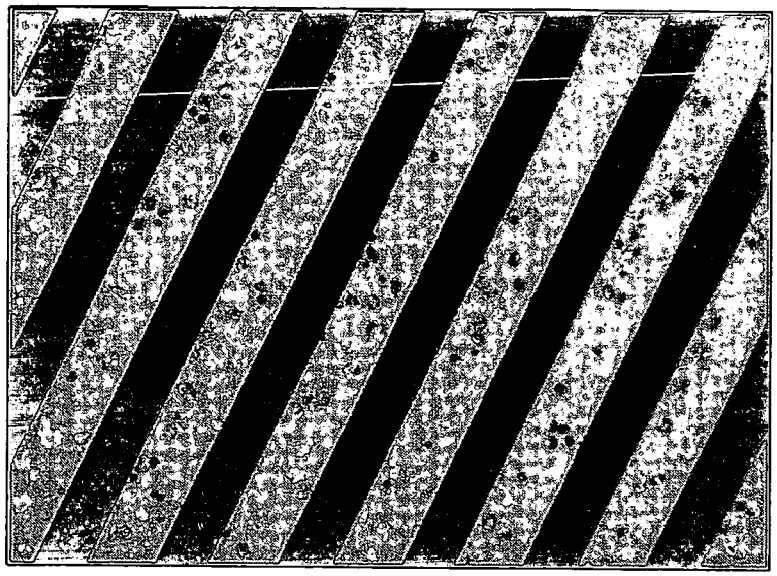
FIG. 11 is a photograph showing a band of an electrosmear created in accordance with embodiments of the present disclosure, the band including neutrophils, lymphocytes and few red blood cells.
Figure 12:
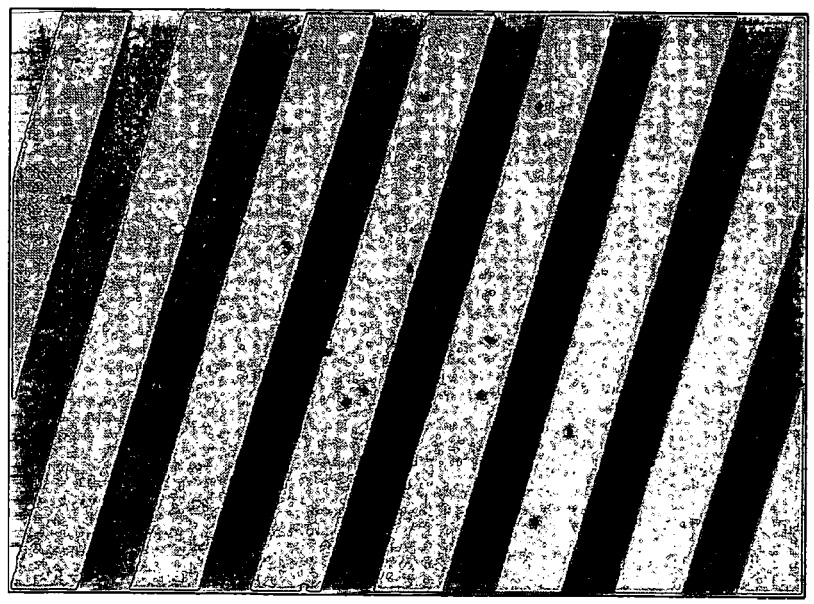
FIG. 12 is a photograph showing a band of an electrosmear created in accordance with embodiments of the present disclosure, the band including predominantly lymphocytes.
Figure 13:
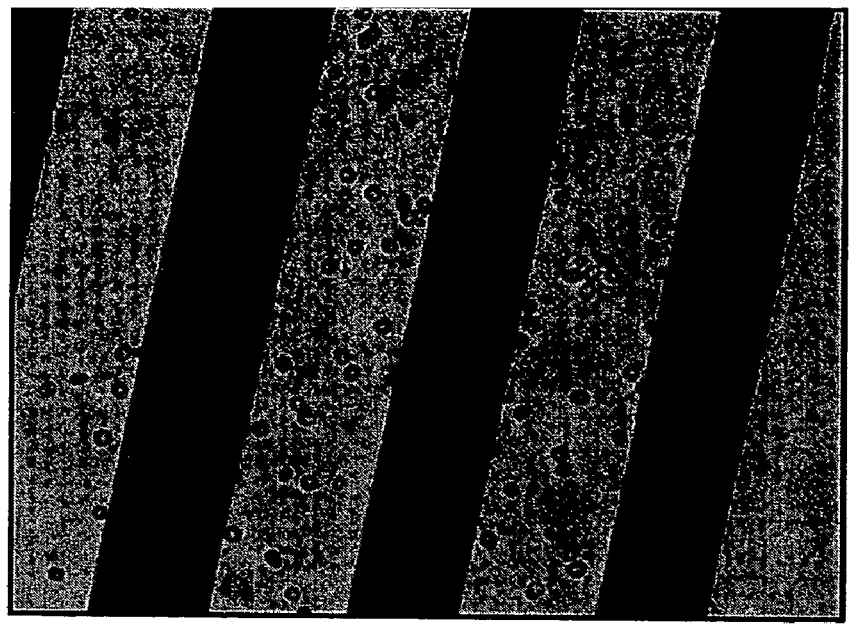
FIG. 13 is a photograph showing a band of an electrosmear created in accordance with embodiments of the present disclosure, the band including exclusively red blood cells and no contamination of white blood cells.

Since we did not see too many lymphocytes in our blood cell preparation, we next prepared white blood cell population by buffy coat method from 5 ml. of fresh blood without any attempt to lyse red blood cells. We found mainly three bands at 17 KHZ, 27 KHZ, and 76 KHZ locations. Band 1 at 17 KHZ contains mainly white blood cells including neutrophils, lymphocytes and very few red blood cells distributed diffusely (see FIG. 11). Band 2 at 27 KHZ contains white blood cells comprising predominantly of lymphocytes with rare neutrophils and red blood cells (see FIG. 12). Band 3 at 76 KHZ is a narrow band comprised exclusively of red blood cells with no contamination of white blood cells (see FIG. 13). Both band 1 and 2 contain few dead or blown out cells among other live cells.

Human Leukemia (cell line Hl-60) Mixed With Blood

Conductivity 10 ms/m; cell concentration of $10 \times 10^6$ cell/ml for HL-60 and $20 \times 10^6$ cells/ml for blood cells.

Figure 14:
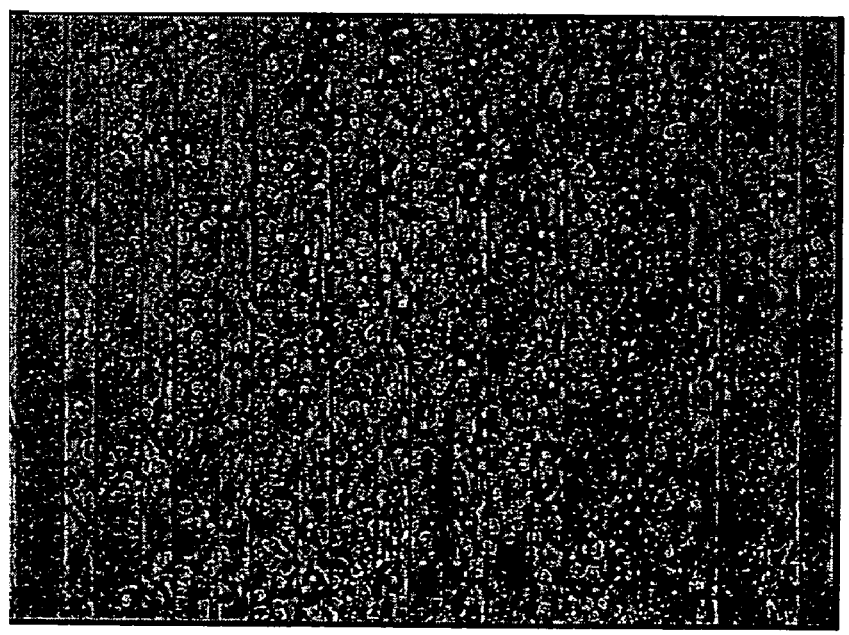
FIG. 14 is a photograph showing a band of an electrosmear created in accordance with embodiments of the present disclosure, the band including HL60 trapped at 10 KHZ
Figure 15:
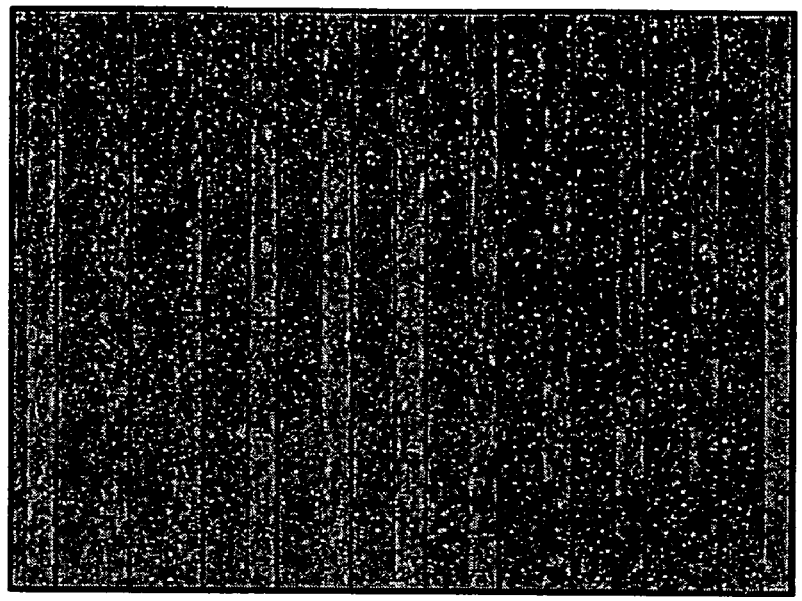
FIG. 15 is a photograph showing a band of an electrosmear created in accordance with embodiments of the present disclosure, the band including blood cells trapped around 17 KHz.
Figure 16:
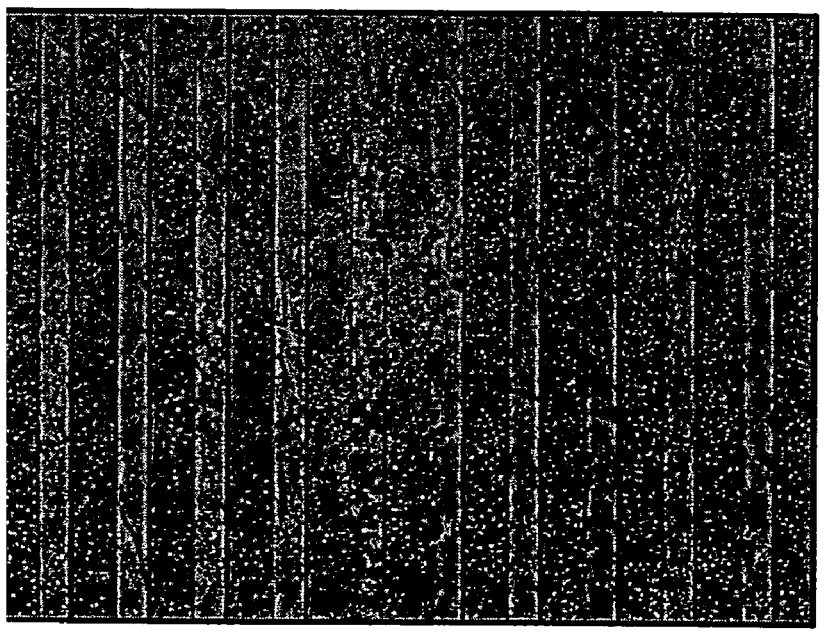
FIG. 16 is a photograph showing a band of an electrosmear created in accordance with embodiments of the present disclosure, the band including RBCs trapped around 76 KHz.

Blood cells were obtained by lysis method with 85 mOs sucrose/dextrose solution. Slides were observed before and after staining. Before staining, we saw four bands, one main band at 10 KHz region comprised mainly of HL60 cells (see FIG. 14) with very few neutrophills, lymphocytes, and no red blood cell at all, followed by a small band of blood cells at 17 KHz (see FIG. 15) containing mostly lymphocytes mixed with very few RBCs, neutrophills, and cancer cells. A $3^{rd}$ band of a few scattered cancer cells was seen at 43 KHz. Cancer cells in this region are diffuse and smaller, and many are degenerating. A $4^{th}$ tight narrow band of red blood cells was seen at 76 KHz region (see FIG. 16).

Figure 17:
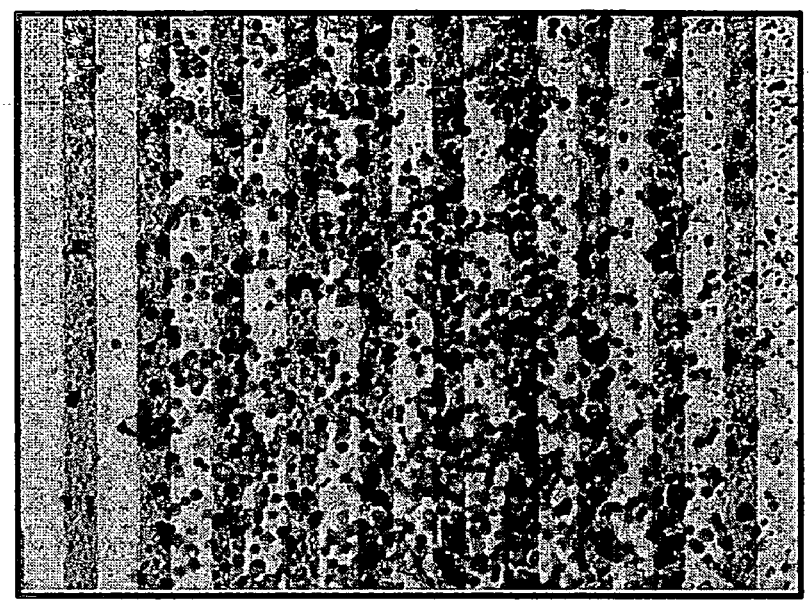
FIG. 17 is a photograph showing a band of an electrosmear created in accordance with embodiments of the present disclosure, the band including stained HL60 trapped around 10 KHz.
Figure 18:
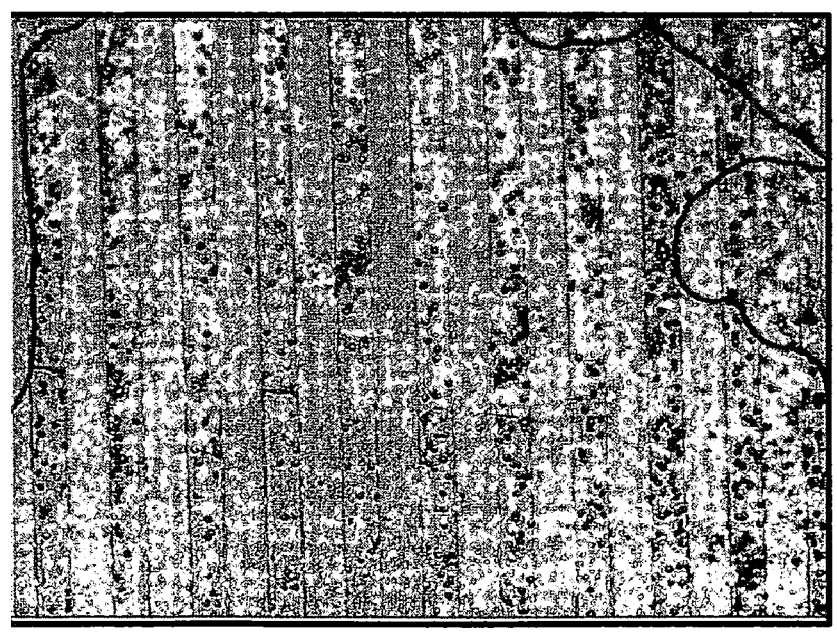
FIG. 18 is a photograph showing a band of an electrosmear created in accordance with embodiments of the present disclosure, the band including RBCs trapped around 76 KHz.

After staining, mostly two bands were prominent in the slide, one at 10 KHz composed of mainly cancer cells (see FIG. 17), and one at 76 KHz which includes mostly RBCs (see FIG. 18). However, the band at 17 KHz comprised of mainly lukocytes was not very prominent by this staining procedure; accordingly, other staining procedures may be used. The electrosmear experiment showed that particular cell types, such as cancer cells, can be separated from blood cells.

Human Breast Cancer Cells (cell line MDA-MB-435) Mixed With Blood Cells

Conductivity 10 ms/m; cell concentration $7 \times 10^6$ MDA cells and $50 \times 10^6$ blood cells per ml.

Figure 19:
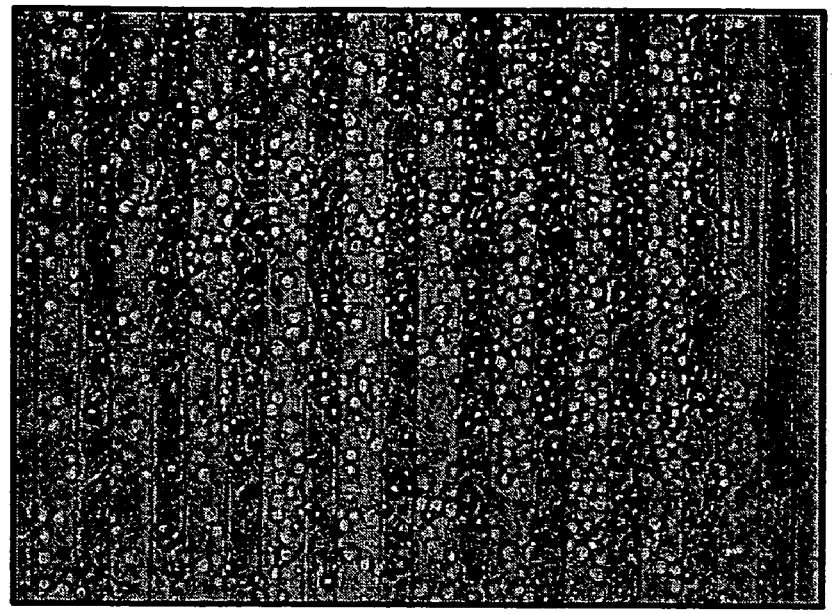
FIG. 19 is a photograph showing a band of an electrosmear created in accordance with embodiments of the present disclosure, the band including only MDA 435 cells at a 9 KHz region.
Figure 20:
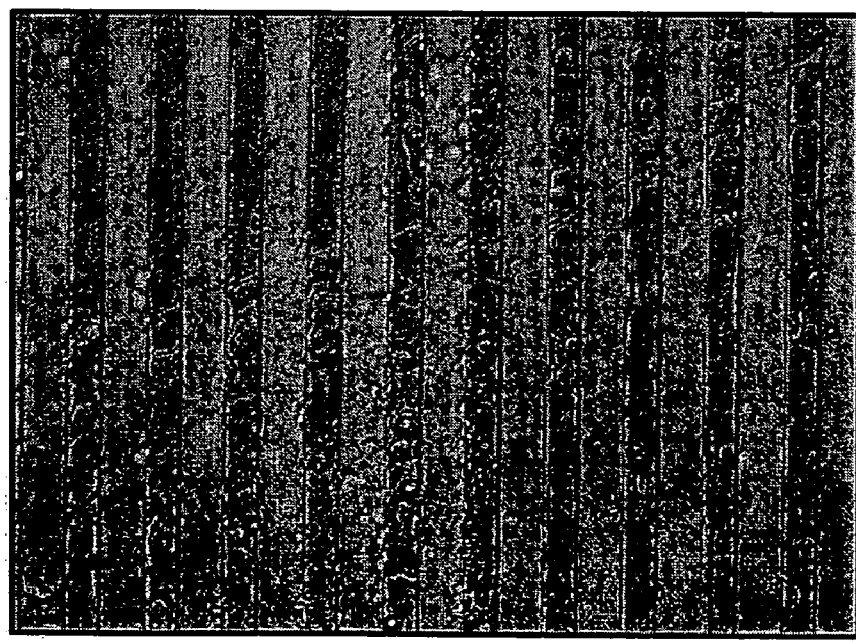
FIG. 20 is a photograph showing a band of an electrosmear created in accordance with embodiments of the present disclosure, the band including predominantly blood cells and few cancer cells at 17 KHz.
Figure 21:
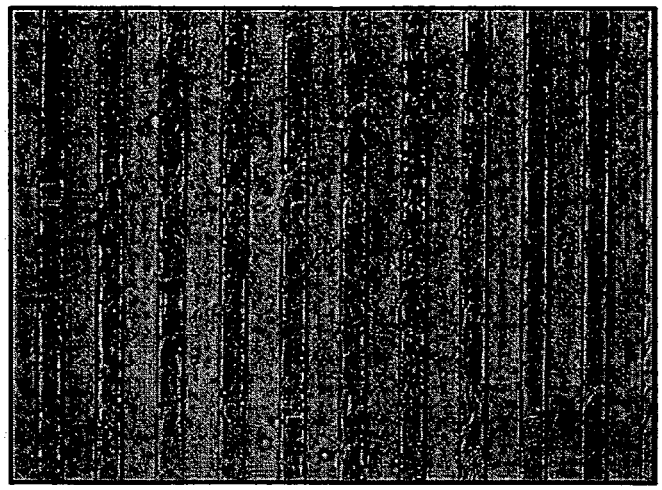
FIG. 21 is a photograph showing a band of an electrosmear created in accordance with embodiments of the present disclosure, the band including exclusively smaller blood cells at 76 KHz.

Four bands were seen: 2 bands in the beginning comprised mainly of MDA435 cells and 2 bands at the end composed mainly of blood cells. The first band appeared in the region of 6 KHz, and the second band at the 9 KHz region (see FIG. 19). The second band contained most of the MDA 435 cells and is followed by two bands of blood cells at 17 KHz (see FIG. 20) and 76 KHZ (see FIG. 21). Again, the experiment shows that particular cell types, such as cultured breast cancer cells, can be readily separated from blood cells by electrosmearing.

Summary of Results

Figure 22:
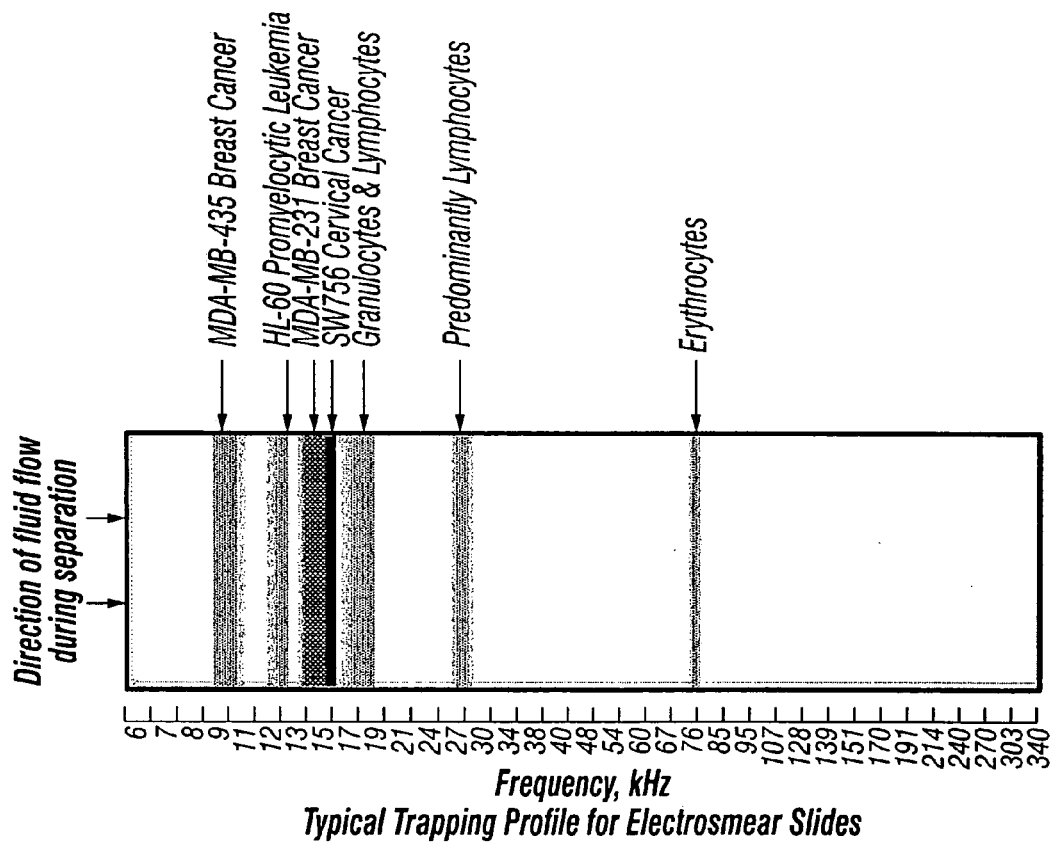
FIG. 22 is a schematic diagram summarizing different exemplary trapping profiles, in accordance with embodiments of the present disclosure.

Cell subpopulations within various mixtures of cells were separated and banded into characteristic regions of the electrosmear. The positions of different cell types can be summarized for an electrosmear separation run at 10 mS/m as summarized in FIG. 22.

EXAMPLE 2

Illustrative Swept Frequency Electrosmear Embodiments

For the electrosmear applications mentioned here, it is advantageous to have the ability to improve particle collection from a dilute suspension. This example is directed to embodiments that achieve that goal. Further, this example describes embodiments that provide for an unlimited range of cell discrimination settings on a slide having, in one embodiment, only 4 large connection pads that are easy to align.

Figure 25A:
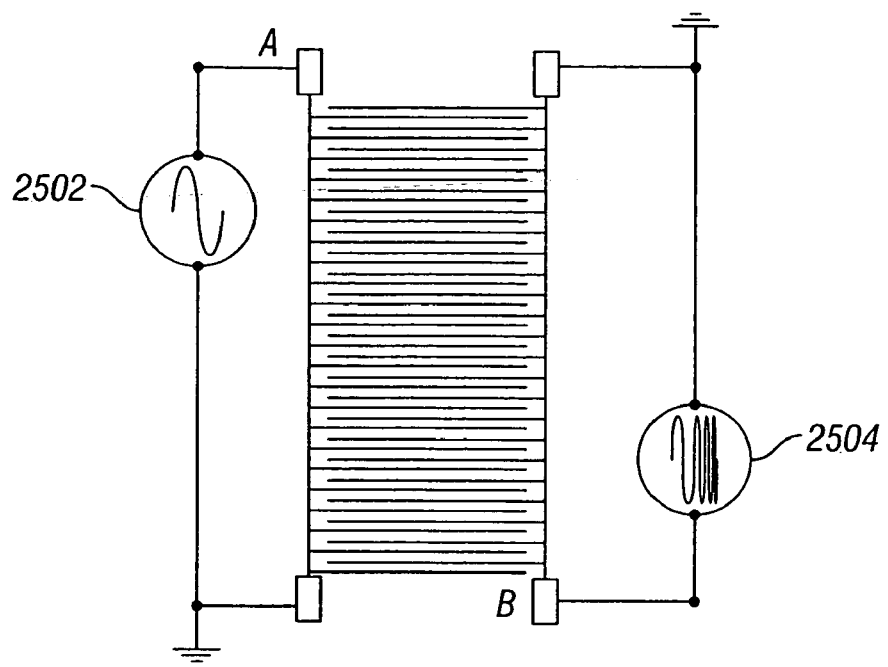
FIGS. 25A–B are schematic diagrams of apparatuses for preparing a smear for cytopathology, according to embodiments of the present disclosure.
Figure 25B:
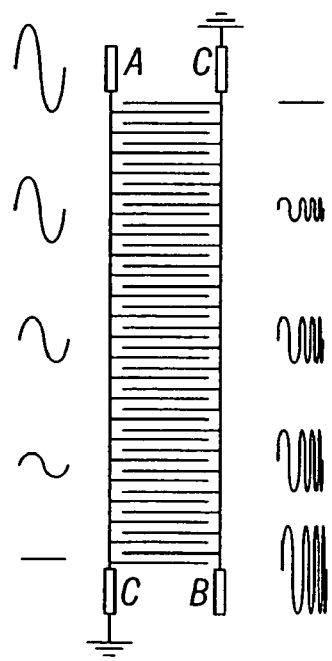

FIGS. 25A and 25B illustrate an electrically resistive electrode system to which two signals are connected. One signal may be a fixed frequency, and the other may be a swept frequency. The electrode system may be a parallel interdigitated electrode or any other design suitable to provide an inhomogeneous electrical field useful for dielectrophoretic collection of particles. In FIG. 25A, element 2502 can correspond, in one embodiment to a 20 kHz signal generator or other generator suitable for forming a fixed frequency. Element 2504 can correspond to a 20 kHz–2 MHz FM signal generator or other generator for forming a swept frequency. It will be apparent to those having ordinary skill in the art that the frequencies given here are not limiting and other frequencies and ranges can be used.

As can be seen with reference to FIG. 25B, electrodes can be connected such that the signal from one signal source falls from a maximum intensity to a minimum intensity along the length of a surface (e.g., a fluid pathway through which the sample is to be passed). The change in intensity with distance may be realized through resistive drop in the field intensity due to resistance of an electrode array. The second signal source can be connected in the opposite sense so that it changes in intensity from a minimum to a maximum intensity. In this manner, a sum of electric fields from the two signal sources is provided along the length of the surface such that one signal falls from maximum to minimum intensity along the length as the other signal rises from minimum to maximum intensity.

To consider the DEP forces experienced by particles as they are carried by fluid flow, it is helpful to consider their dielectric properties as a function of applied dielectrophoretic field frequency. As an example one can consider mammalian cells. The relative DEP force on mammalian cells suspended in a low conductivity medium is negative (repulsive) at low frequencies but crosses over to positive (attractive) above a characteristic crossover frequency. A negative DEP force causes cells to be repelled from high field regions on an electrode; a positive DEP force causes cells to be attracted, and possibly trapped, at these high field regions.

With respect to embodiments of this example, it is also helpful to consider what happens when a DEP field frequency is swept between a low frequency and a high frequency periodically in time. In general, the DEP force experienced by the particles will change in accordance with the swept field frequency, alternating between repulsive and an attractive force. If the sweep frequency is so high that a particle is unable to move through a suspending medium in response to the time varying DEP force, the particle will behave as though it were being exposed to a DEP force equal to the time average of the periodic DEP force. This time averaged DEP force will reflect, particularly, the relative positive and negative DEP forces experienced by the particle. Because different particle types (e.g., different cell types) have different crossover frequencies, the relative time each particle type experiences positive versus negative DEP forces from the swept frequency signal will be different. Therefore, different particle types will experience different net DEP forces in accordance with their dielectric properties. However, a constant, low frequency DEP field can be used to provide a constant negative (repulsive) DEP force on each particle type.

The example electrode configuration illustrated in FIGS. 25A and 25B provides a sum of signals from two signal sources. For illustration, consider the case where a signal of constant frequency providing a repulsive DEP force is the signal having highest intensity where particles enter, though this example is not limited to this case. The field falls with distance along the length of the surface (see line 2602 of FIG. 26A). The swept field, which one can assume for illustration purposes provides a net positive DEP force, rises in intensity along the length of the chamber (see line 2604 of FIG. 26A).

Figure 26A:
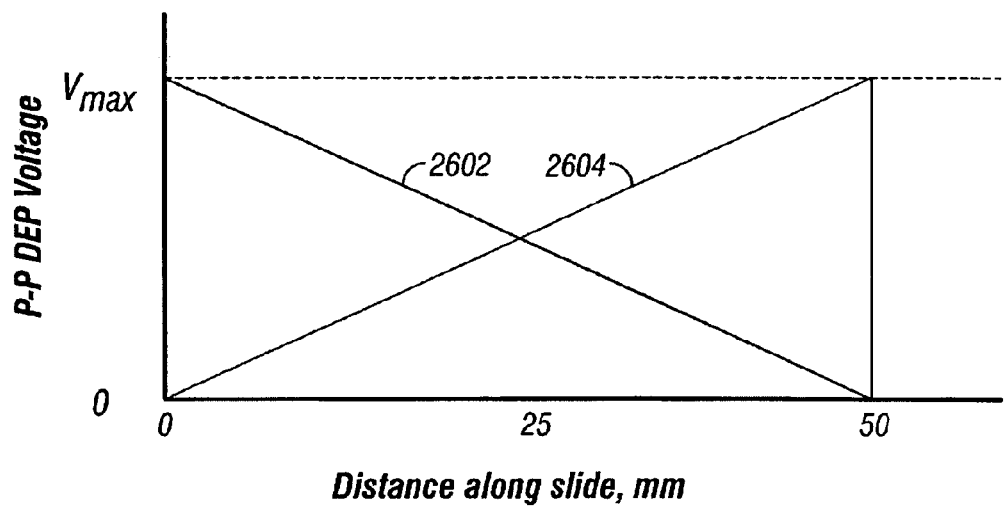
FIGS. 26A–B are graphs illustrating trapping characteristics, according to embodiments of the present disclosure.
Figure 26B:
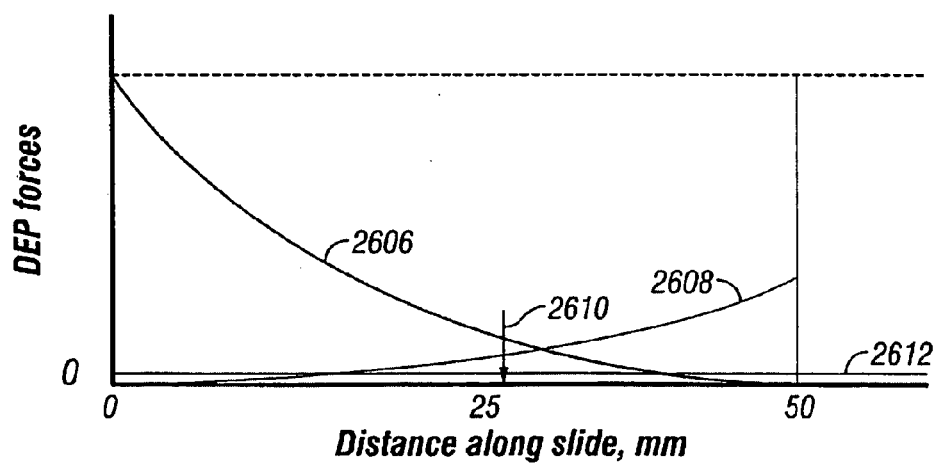

The DEP force experienced by a particle depends on the square of the electric field intensity, and the DEP forces from the two signals impinging on the particle simultaneously (or they could be alternated rapidly) add to provide a net DEP force. The total vertical force on each particle is then the sum of the net DEP force and that due to gravity (sedimentation force). At some position along the surface, the sum of levitating negative and positive DEP force and sedimentation force are zero at the surface, and the particle will settle and become attached. This is illustrated generally in FIG. 26B, where line 2606 represents a repulsive (levitating) DEP force, line 2608 represents an attractive (trapping) DEP force, line 2612 represents a gravitational force, and arrow 2610 represents a trapping position. In FIGS. 26A and 26B, it is assumed that the surface is associated with a slide, but it will be understood that such an association is not required. Further, the distances along the x-axis serve as examples only.

Figure 27:
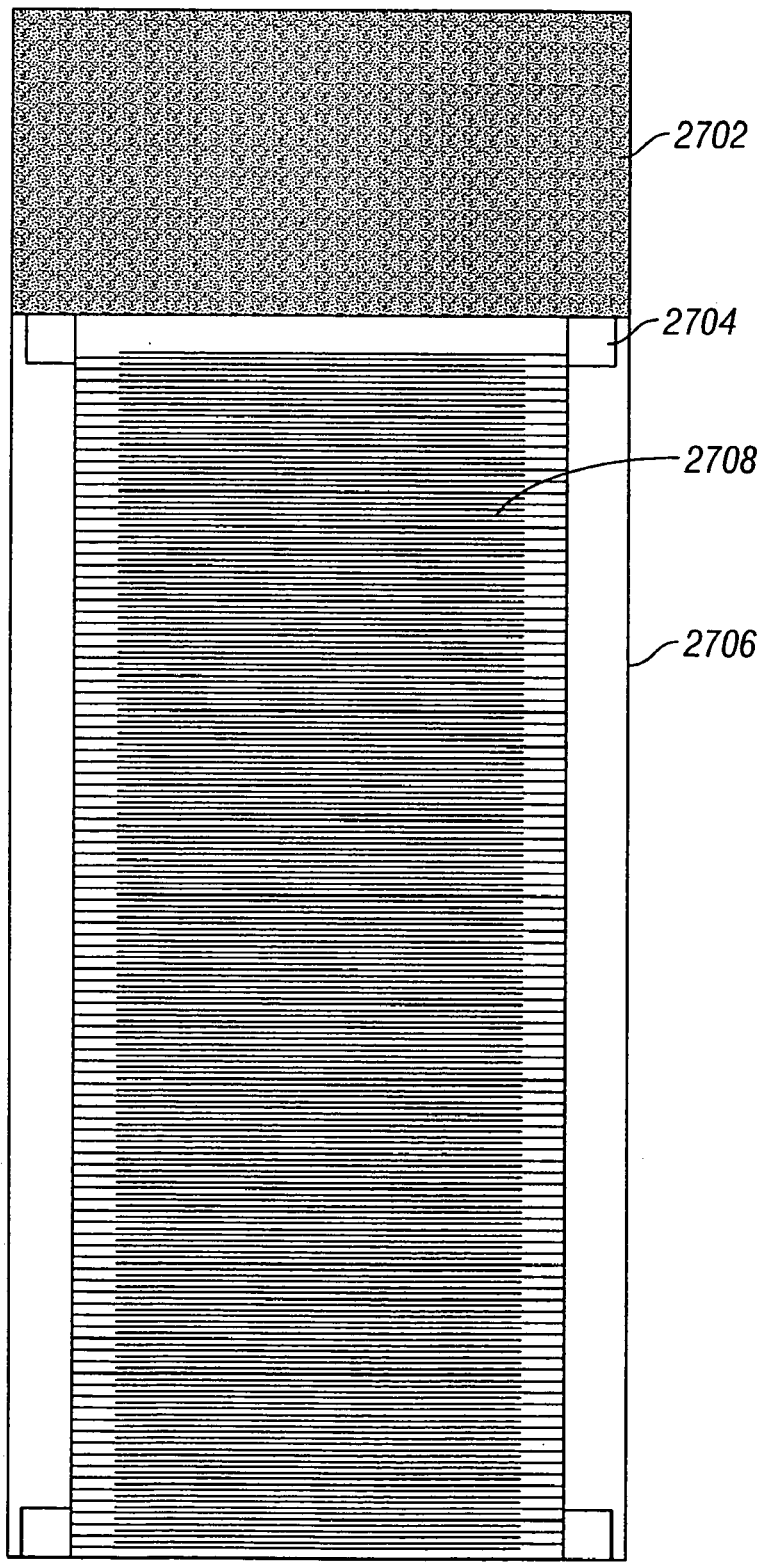
FIGS. 27–29 are schematic diagrams of apparatuses for preparing a smear for cytopathology, according to embodiments of the present disclosure.

FIG. 27 illustrates an example electrosmear configuration. End 2702 can be ground glass or any other surface suitable for labeling. Element 2704 is a connection pad. Element 2706 is a dielectric substrate. Typical substrate materials can include but are not limited to: glass, plastic, polymer, or kaptan. In a preferred embodiment, dielectric substrate 2706 is a glass substrate, and more particularly, a microscope slide: sized 1"×4" to fit standard microscope slide processing for staining, automatic manipulation, storage, and the like. Element 2708 is an electrically resistive electrode pattern. Typical electrode materials can include but are not limited to: thin gold on titanium or chromium, gold-plated copper, or other metal, indium tin oxide or other transparent conductive material.

EXAMPLE 3

Further Illustrative Swept Frequency Electrosmear Embodiments

Again, two electrodes can be used to provide a spatial distribution of field intensities from two signal sources. The response of the particles results from the superposition of fields and also the tendency of the particles to effectively time average the superposed fields. Specifically, a frequency modulated signal can be repeatedly swept through a range of frequencies for which a given particle type may experience negative DEP, no DEP, and positive DEP. The frequency may be swept with time in any suitable manner, including, but not limited to, sine, triangle and sawtooth (sometimes called "chirp") frequency vs. time characteristics. If the sweep is too slow, the particles will respond to the swept frequency and at any given position of an electrosmear slide exhibit negative, zero, and positive DEP that cause the particle to fall and rise in levitation height above the electrode plane in step with the frequency at a given point in time. In general this, although it may be useful for some applications, is undesirable. On the other hand, if the frequency sweep is sufficiently fast that the particles do not have sufficient time to significantly change height in response to the changing frequency, they will move instead to an "average" height about which they may show miniscule height variations due to the ongoing frequency modulation. This is a preferred manner of operation for the device in one embodiment. The frequency sweep repetition rate typically needs to be 100 or more times per second to achieve this "averaging" effect.

Figure 28:
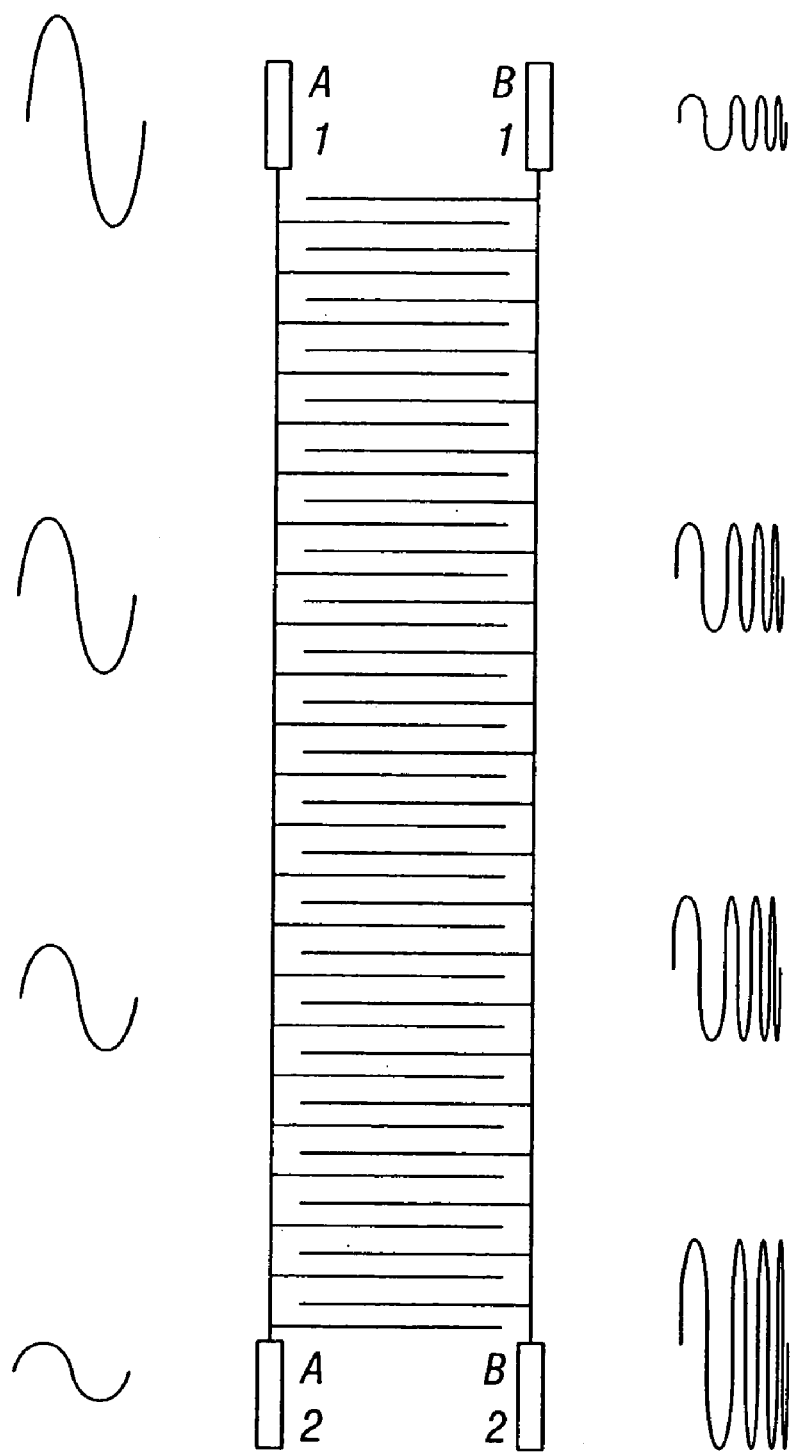

FIG. 28 shows a variant embodiment in which signals from the signal generators vary in intensity from a high to a low voltage rather than from a high voltage to zero, which can improve the flexibility of the method for setting selectivity towards cells. On the left, a low frequency pure tone is shown, and on the right a FM swept tone. In FIG. 28, the electrode is connected such that the signal from one signal source falls from a maximum intensity to a minimum intensity along the length of a fluid pathway through which the sample is to be passed. The change in intensity with distance can be realized through resistive drop in the field intensity due to resistance of the electrode array. The second signal source can be connected in the opposite sense so that it changes in intensity from a minimum to a maximum intensity along the surface. In this manner, a sum of electric fields from the two signal sources is provided along the length such that one signal falls from maximum to minimum intensity along the length as the other signal rises from minimum to maximum intensity.

Figure 29:
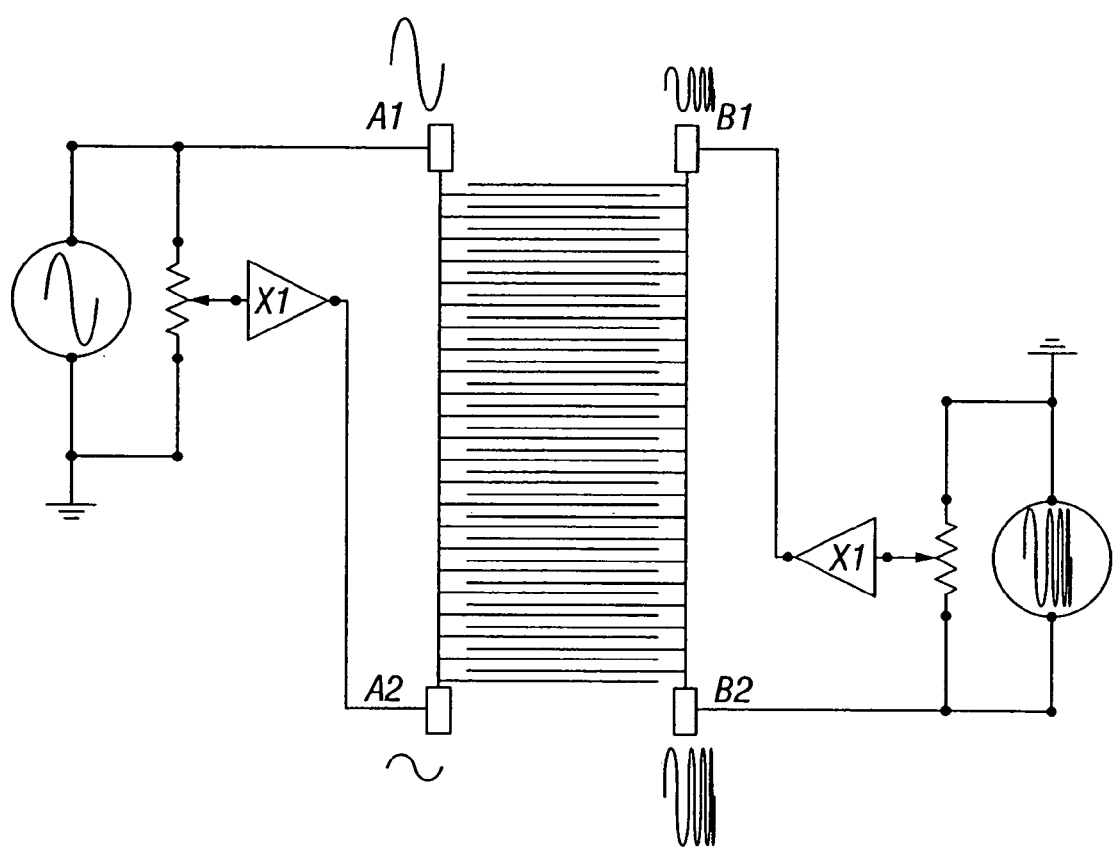

FIG. 29 shows a suitable circuit that may be used to energize an electrosmear slide according to embodiments of at least Examples 2 and 3 (e.g., between a high and low voltage for each signal). The signal generator at left can be a single frequency generator, and the generator at right can be an FM signal generator. In practice, the signal generators and the attenuation of the amplifier stages can be digitally controlled to allow easy computer or digital controller operation of the signals. As with other embodiments, one may use an electrically resistive electrode system to which two signal sources are connected. One signal may be a fixed frequency, and the other may be a swept frequency. The electrode system can be a parallel interdigitated electrode or any other design as may provide an inhomogeneous electrical field useful for dielectrophoretic collection of particles. The electrode can be designed to have internal resistance so that the intensity of signal A on the left hand electrode (see FIG. 29) falls in the direction A1 to A2 while that of signal B falls in the direction B2 to B1 on the right electrode (see FIG. 29).

FIGS. 30A–30F illustrate simulations of the typical trapping behavior for cells having different trapping frequencies on a typical electrosmear slide. The simulations show examples of how the discrimination of the method for different cell types can be adjusted.

The ability to adjust electrosmear particle trapping characteristics can be extremely advantageous and can improve embodiments in which a spectrum of discrete frequencies are applied to individual electrodes. FIGS. 30A–30F illustrate how the distances along an electrosmear slide at which particles having different dielectric crossover frequencies can be altered by adjusting, for example, the signal intensity variation along a slide and the frequency modulation range of an FM signal. In FIGS. 30A–30F, $F_{min}$ is the frequency of the fixed-frequency DEP field. The frequency range of the swept field is shown as FM.

The top charts of FIG. 30 (FIGS. 30A, 30C, and 30E) show the time averaged Claussius-Mossotti factor calculated for particles having crossover frequencies given in the abscissa for a low frequency constant signal of 10 kHz (bottom plot) and for the FM signal (top plot). The range of frequencies between which the modulated signal is swept and the voltages applied at the electrodes are shown at the top of each set of figures.

The bottom charts of FIG. 30 (FIGS. 30B, 30D, and 30F) show on the ordinate the distance in mm from one end of the electrode on an electrosmear slide at which cell types having crossover frequencies shown on the abscissa will be trapped. Note that as the voltages applied to the electrodes are changed and the range of frequencies of the FM signal is changed, so the trapping distribution of cells having different crossover frequencies can be altered.

Figure 30A:
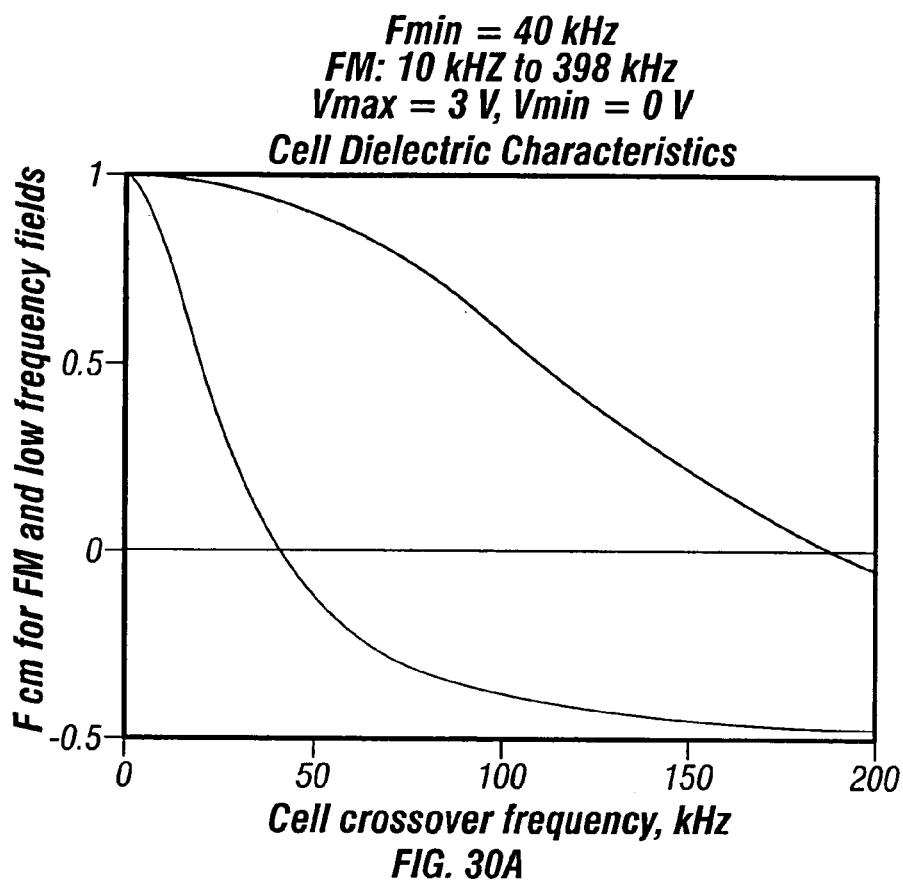
FIGS. 30A–F are graphs illustrating adjustment of particle trapping characteristics, according to embodiments of the present disclosure.
Figure 30B:
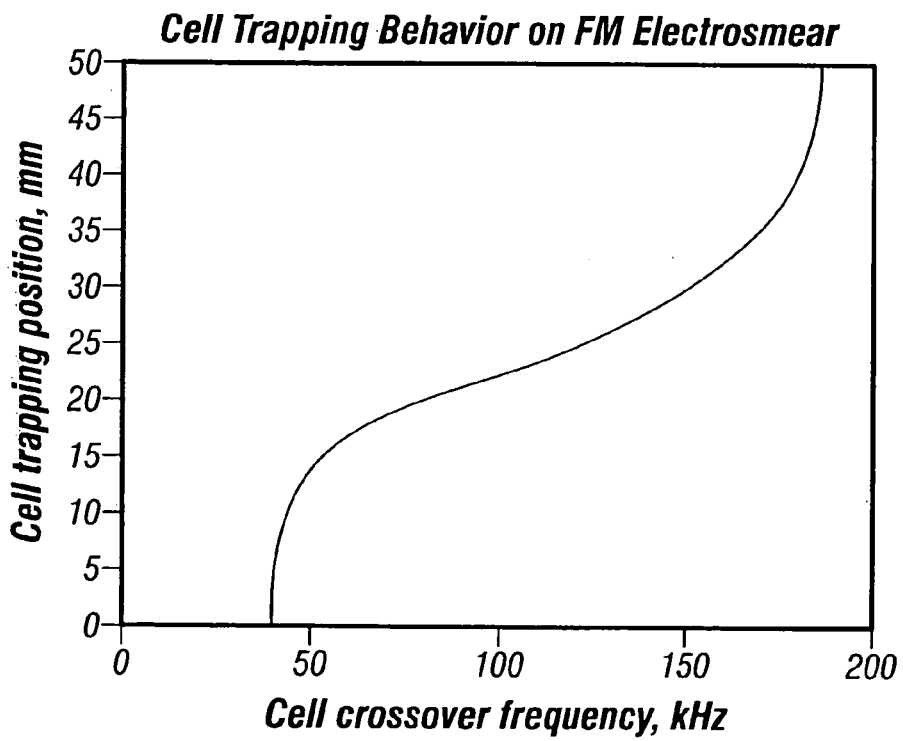
Figure 30C:
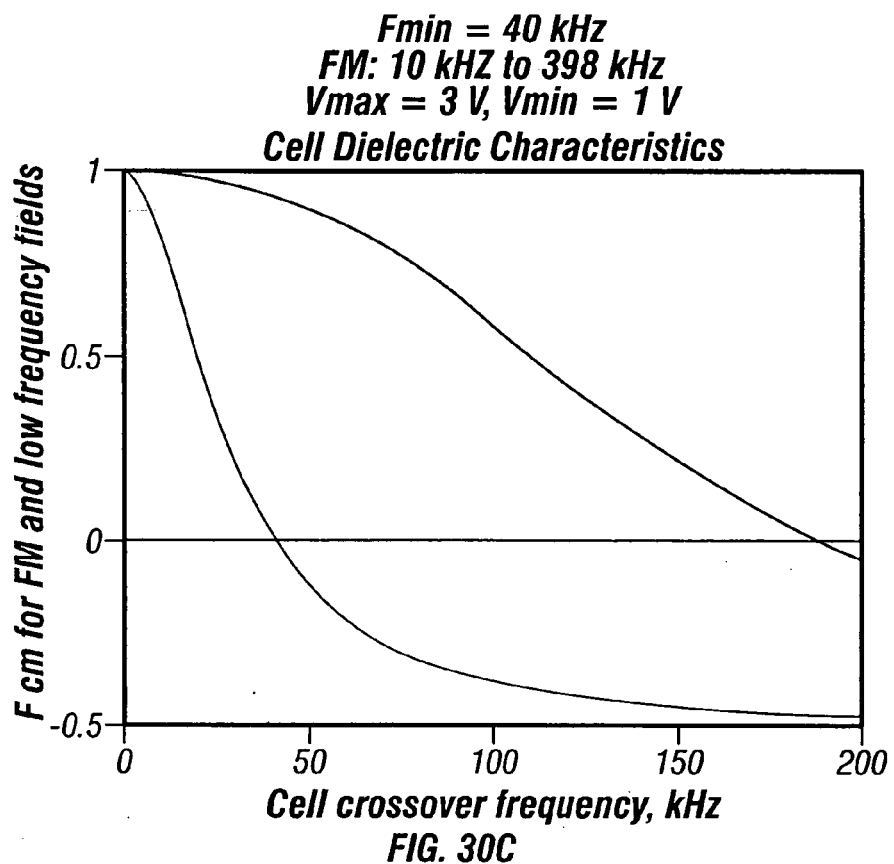
Figure 30D:
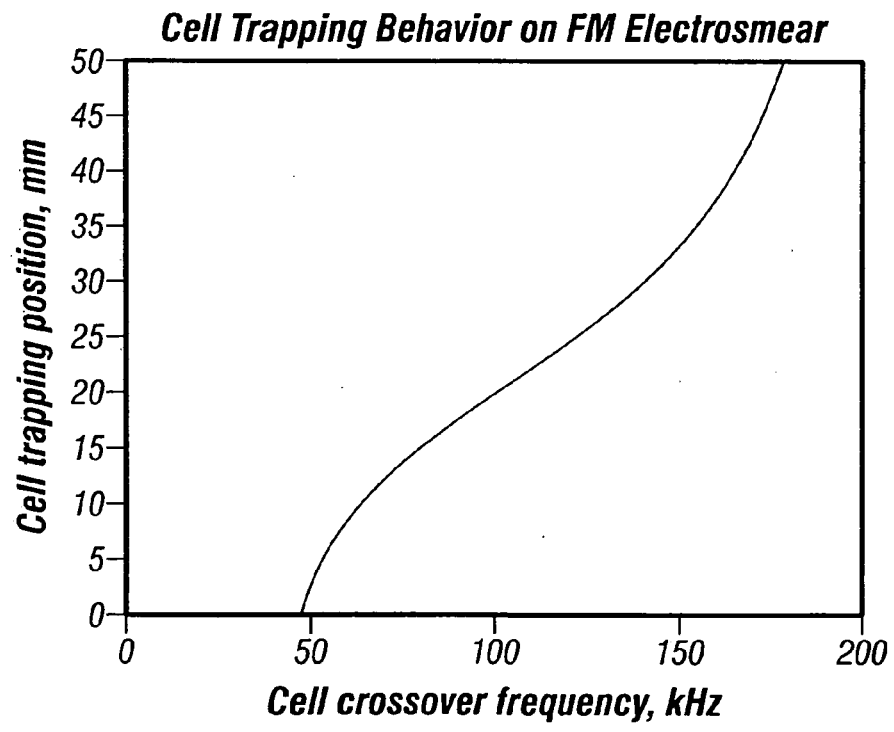
Figure 30E:
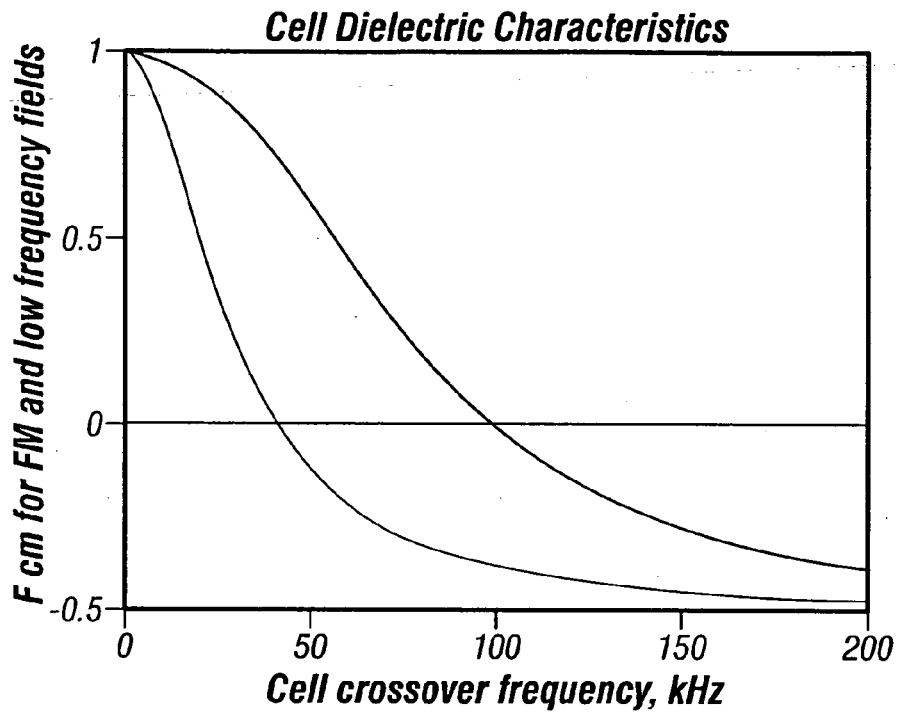
Figure 30F:
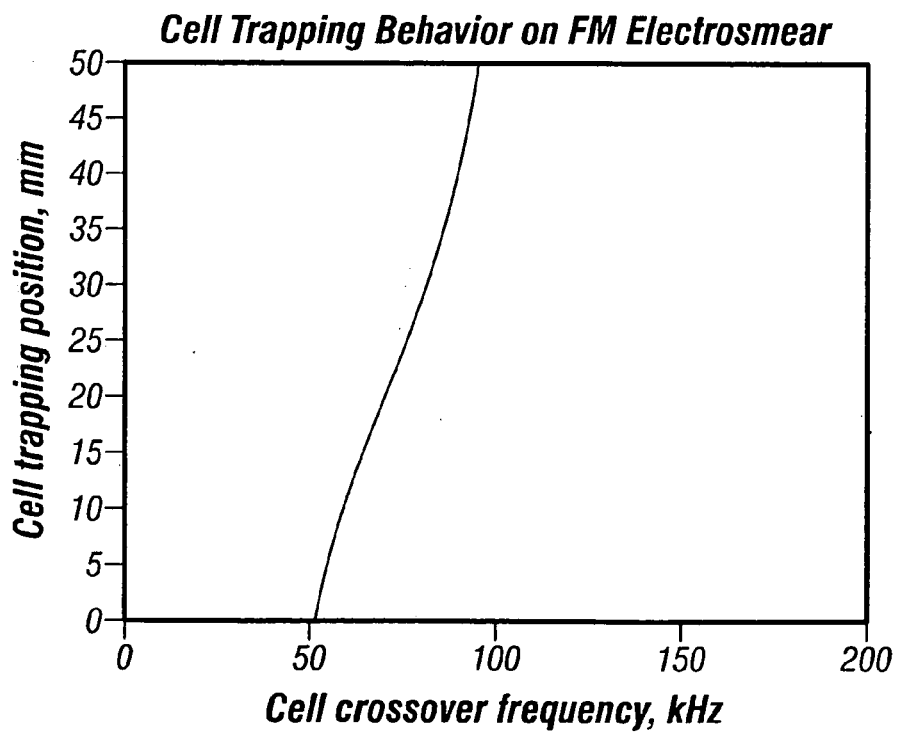

Explaining further, the upper curves in FIGS. 30A, 30C, and 30E show the effective DEP force acting on particles as a result of a swept frequency of constant amplitude as a function of particle crossover frequency. The lower curves in FIGS. 30A, 30C and 30E show the DEP force on the same particles from a DEP field of fixed frequency. FIG. 26 show that the DEP voltage for the swept and fixed frequency field alter with distance along the electrosmear slide in, e.g., FIG. 31. As a consequence, the net DEP force acting on particles, the sum of DEP forces resulting from the swept and fixed frequency fields, also varies with distance along the electrosmear slide in FIG. 31. The position at which particles having different crossover frequencies are trapped because of this variation in intensities of the fields along the electrosmear slide is shown in FIGS. 30B, 30D and 30F.

FIGS. 30A and 30C are for identical fixed field and field sweep settings but for different field intensity gradients along the electrosmear slide. The corresponding trapping positions shown in FIGS. 30B and 30D reflect these field gradient differences. FIGS. 30C and 30E are for identical field intensity gradient settings but for different field frequency sweep ranges. The corresponding trapping positions shown in FIGS. 30D and 30F reflect the trapping characteristics. None of these figures are restrictive; rather, they are examples of a very wide range of possible settings that can be chosen to best suit each specific application, as will be understood by those having ordinary skill in the art.

In certain embodiments described here, the field strength is considered to vary linearly with distance along the electrosmear slide (e.g. FIG. 25B illustrates this). The techniques of this disclosure can readily be applied to other cases as well. For example, by varying the width of electrode buses with distance along the sides of the electrosmear slides, the field intensity may be made to have a non-linear relationship to distance along the slide. For example, the DEP force varies with the square of the field intensity. Therefore, if the thickness of the supply bus along the electrosmear is contoured so as to produce a field that falls with the square-root of distance along the slide then the DEP force will alter linearly with distance. Of course, any desirable contour could be utilized to provide desired separation results of particles along the electrosmear.

Note that embodiments here and throughout the specification can provide a method of cell preparation that is quite distinct from typical blood smear or cytospin methods: electrosmear signals can be set so that specific cell types of interest may be spread in characteristic bands on a slide while other cell types may be captured at ann entrance or may flow off the far end of a slide. In this way, the electrosmear can select from a sample containing very high numbers of cells only those of interest for diagnostic applications.

For example, in the detection of residual disease in cancer or malaria, diseased cells may be very rare. The chance of missing diseased cells in a conventional slide preparation technique is limited by the maximum practical number of cells that can be loaded onto a slide. Furthermore, every cell on the slide must be examined to detect the diseased cells. For a conventional slide this number includes many normal cells. In an electrosmear application, only cells fitting the dielectric profile of suspected diseased cells need be trapped while cells having the profile of healthy cells can be allowed to flow off the electrosmear surface. In this way, a sample containing a large concentration of cells may effectively be filtered by the electrosmear and only suspect cells trapped for examination. As a result, larger cell samples may be examined and the probability of detecting disease is scaled accordingly.

EXAMPLE 4

Illustrative Electrosmear Control

Figure 31:
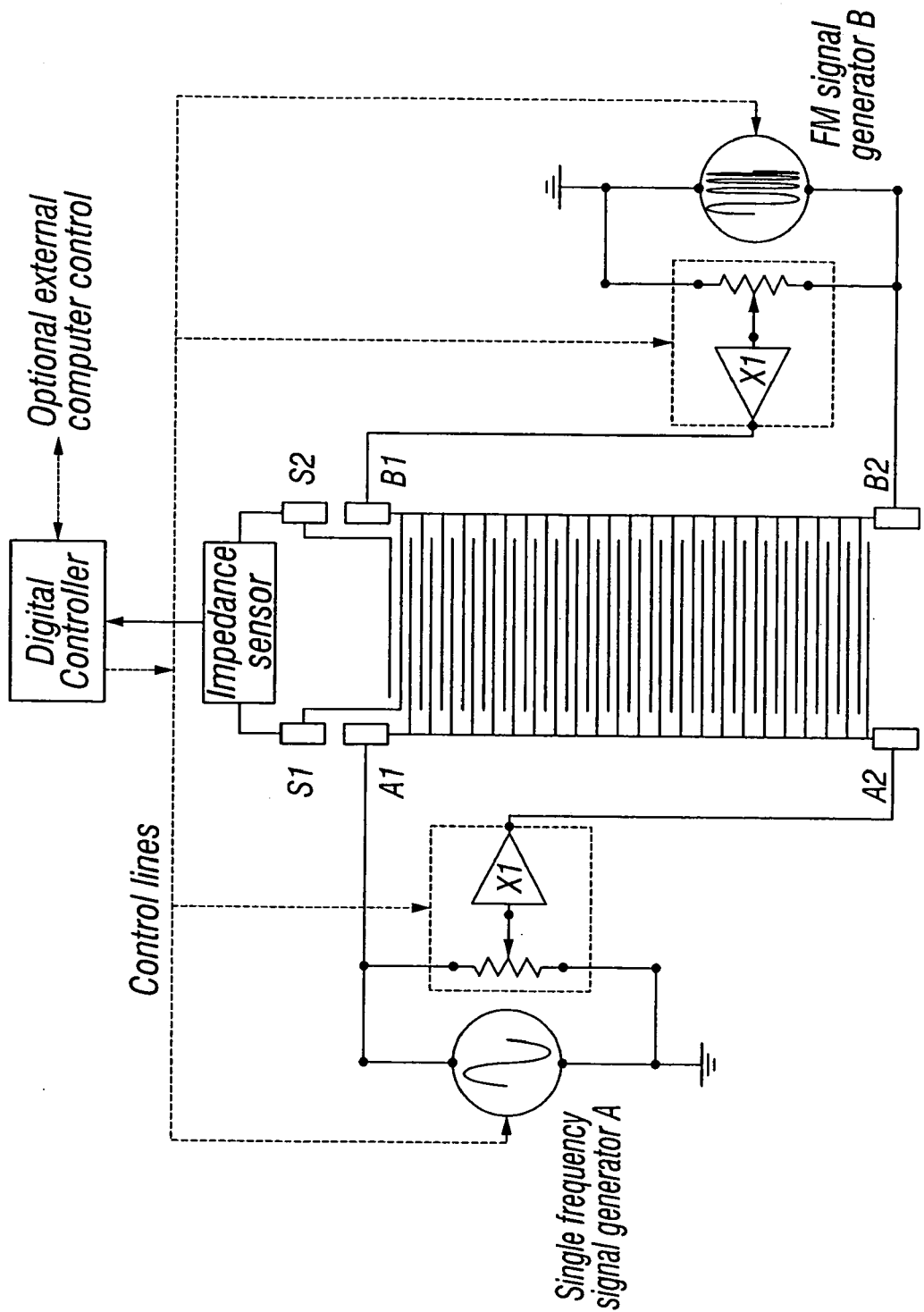
FIG. 31 is a schematic diagram of a system for preparing a smear for cytopathology, according to embodiments of the present disclosure.

FIG. 31 illustrates a system useful for control of electrosmear applications.

The dielectrophoretic crossover frequencies of cells and other particles depends upon the conductivity of a suspending medium used for the electrosmear analysis. It is possible to compensate for variations in suspending medium conductivity by adjusting the frequency of the two signal generators. In one embodiment, this can be accomplished by incorporating an impedance sensor on the electrosmear and using it to provide feedback to a controller that can adjust the signal generators. Since it is often desirable to use a controller to adjust the settings of signal generators and attenuating amplifiers, the same controller can be used to provide feedback compensation for the suspending medium conductivity. If the suspending medium conductivity is so inappropriate for an experiment that compensation is ineffective, the controller can be used to provide a warning or abort the electrosmear procedure according to programmable criteria.

Note the signal generators may be sine wave, triangle, sawtooth, or square wave. Square waves are usually the easiest to generate and are suitable for this application. However, embodiments of this disclosure are not limited to a specific type of signal, as it will be apparent that many different signal types can be used.

The illustrated embodiment of FIG. 31 shows an example of a separate impedance sensor using separate electrodes. In practice, the impedance of the sample can also be inferred from the current in signal generator A and/or B that is used by the larger array to reach the programmed voltage. Such an embodiment eliminates the need for a separate electrode set and an independent impedance sensor. The DEP frequencies needed for a given separation application depend on the conductivity of the suspending medium. FIG. 31 shows that a controller circuit can be used to automatically adjust the frequencies of the signal generators to accommodate differences, or variations, in the particle suspending medium.

EXAMPLE 5

Filtering Apparatus and Methods for Sample Preparation

In many applications, including DEP-FFF, electrosmear, microTAS devices, and PCR, the need arises to prepare a sample that may be suspended in a fluid that would cause undesirable effects if added to an assay. For example, cells may be suspended in sputum, yeast cells in urine, or bacteria in sewage sludge. Additionally, samples containing or suspected of containing target agents including cells, bacteria, viruses, molecules, or prions, may be suspended in a volume of medium at a sub- or super-optimal concentration. For example, target agents may be present at very low concentration in drinking water or mixed with huge numbers of cells in blood.

While filters have been employed for processing such samples, serious problems arise when sample recovery is attempted. These problems include inconvenience, the need for manual involvement, and loss of sample bound to the filter. Embodiments of this disclosure provide a filtering method that allows these problems to be overcome. In representative embodiments, repulsive dielectrophoresis is used to allow the filter to be easily cleared and provides for the direct transfer of target agents to additional sample processing and/or analysis stages without the need for removal or manual intervention.

The devices and methods are widely applicable to sample preparation needs but are especially useful for use with microfluidic instruments including electrosmear, DEP-FFF, spiral electrode, programmable fluidic processor, PCR, or the like.

In embodiments of this disclosure, one may use a filtering stage that can be integrated with an electrosmear slide or apparatus. In a preferred embodiment, a front end filtering stage is used. A filter can allow samples to be collected from a wide range of sources ranging from highly dilute fluid samples to dense suspensions. Once particles have been collected in the filter, they may be rinsed or otherwise processed and perfused with a suitable medium for high-discrimination analysis. The filter can incorporate a dielectrophoretic method for releasing a sample and interfacing it to other analytical or processing methods.

Figure 32A:
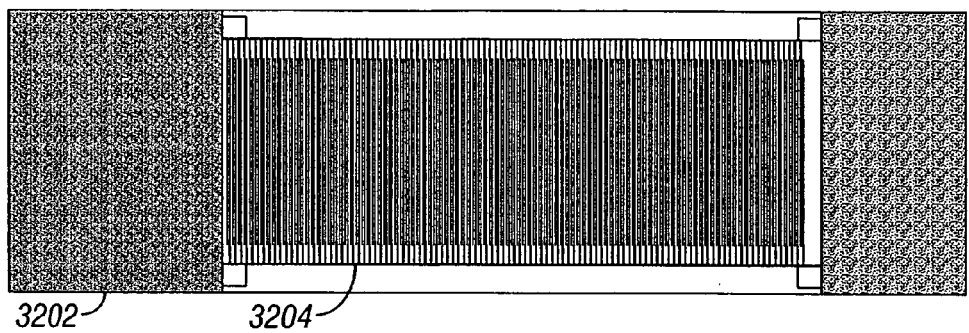
FIGS. 32A–B are schematic diagrams of filters, according to embodiments of the present disclosure.
Figure 32B:
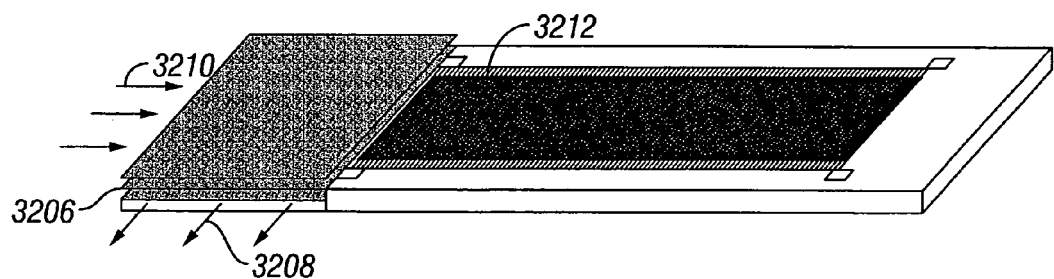

FIGS. 32A (top view) and 32B (isometric view) show general embodiments of suitable front-end filters with an electrosmear apparatus. In those figures, 3202 is a filter and DEP sample release stage, and 3204 is an electrosmear slide with electrodes. Element 3206 is a dielectric such as a polycarbonate track-etch filter (associated embodiments described below), which in one embodiment can be spaced about 50 microns from the top of the filter. Arrows 3210 show the flow-in direction. Arrows 3208 show the direction of flow-out during filtering. Arrows 3212 show the direction of flow-out after filtering. It will be understood that the filter illustrated at FIGS. 32A and 32B need not be used exclusively for electrosmear applications. Rather, it can be used for any application in which filtering is desired. In representative embodiments, it can be used for DEP-FFF, spiral electrode, programmable fluidic processor, PCR, or the like.

In use, a filter assembly can be inserted into a holder that provides electrode and fluid connections. A sample can be injected through the filter to collect sample particles. The collected sample can be optionally rinsed with reagents, lysing buffer (e.g. for eliminating red blood cells), or suitable buffer. An AC field can be applied to help release the sample from the filter and transport it to the slide section. Particles can then settle on the slide in accordance with, for example, the sum of gravitational and DEP forces acting on them in accordance to their dielectric properties. Optionally, an attachment agent can be present on the slide to ensure adhesion of particles when they settled (e.g. cells can be assisted in adhering to slides with polylysine or APES).

In other embodiments, a filter stage can be made to snap off from a slide or detach from it in another fashion so that the slide section alone can be subjected to normal processing (e.g,. staining) and examination (e.g., by a pathologist under a microscope or on an automated slide reader).

Setting up a Filter

Figure 33A:
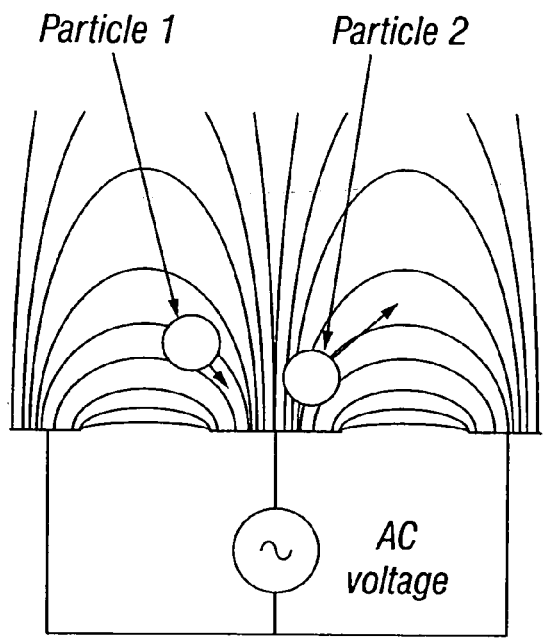
FIGS. 33A–B are schematic diagrams illustrating principles of filtering, according to embodiments of the present disclosure.
Figure 33B:
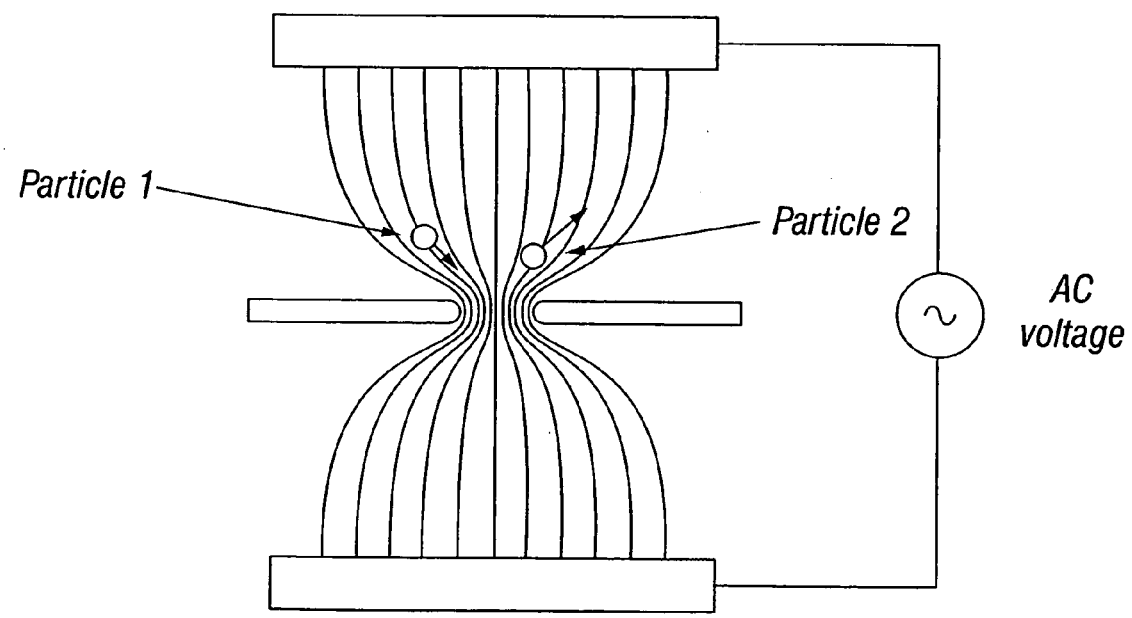

The inhomogeneous electric field distribution produced by excitation of electrodes on a dielectric substrate (see FIG. 33A) or by current passing through a hole in a dielectric barrier (see FIG. 33B) can generate dielectrophoretic forces on particles nearby. A particle having a higher dielectric polarizability than the medium in the channel will experience an attractive (or positive) dielectrophoretic force that pulls it towards high field regions where the field lines are closer together (shown by the arrow on particles 1 in FIGS. 33A and 33B). A particle having less polarizability than the medium in the channel will experience an opposite (negative) dielectrophoretic force (shown by the arrow on particles 2 in FIGS. 33A and 33B).

Electroless DEP, in which the electrical field is "pinched" by dielectric structures to provide electric field inhomogeneities (see FIG. 33B) were reported by Masuda et al. in 1989 (IEEE Transactions on Industry Applications 25(4): 732–737(1989)) and by Lee et al. who recapitulate that method (Engineering in Medicine and Biology Society: Proc. 16th Annual International Conf. IEEE 2:1019–1020 (1994) ISBN:0-7803-2050-6); each of those references is incorporated herein by reference.

First Set of Embodiments

Figure 34:
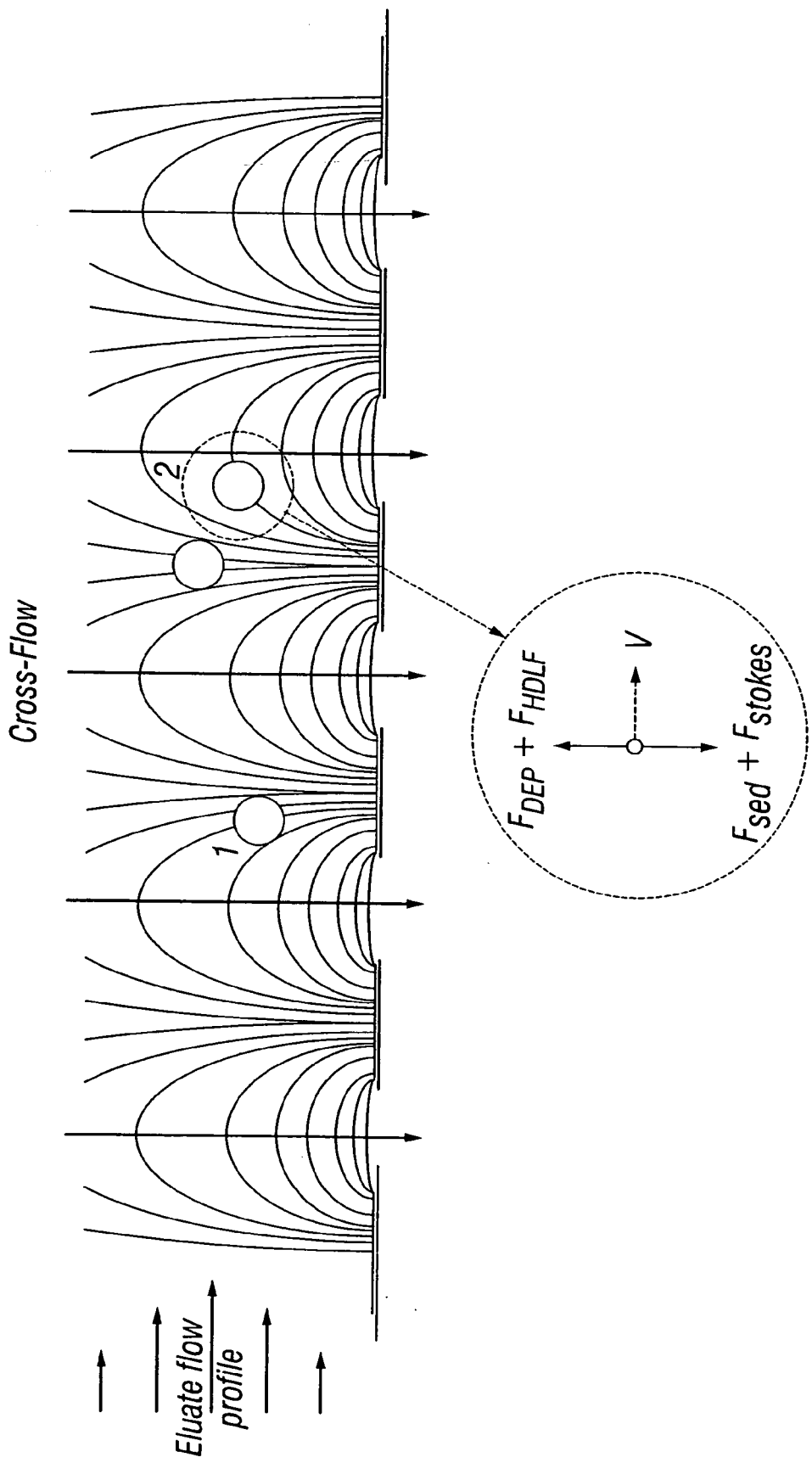
FIG. 34 is a schematic diagram illustrating principles of filtering, according to embodiments of the present disclosure.

FIG. 34 shows competing stokes and dielectrophoretic forces in flow-FFF using electrodes arrayed on a dielectric channel wall having holes to allow fluid flow. Particles 1, 2 and 3 are shown being influenced by stokes drag from fluid cross-flow and dielectrophoretic forces arising from the electric field distribution above an electrode array. In all the figures here, the "cross" flow, in a preferred embodiment, is a substantially perpendicular flow. In other embodiments, at least a component of the cross flow is substantially perpendicular (i.e., the cross flow can be resolved into at least one component substantially perpendicular another flow). The inset in the dotted circle shows the forces on particle 3. The velocity of the particle V arises from the eluate flow velocity. $F_{sed}$ represents a sedimentary force, and $F_{HDLF}$ represents a hydrodynamic lift force. The hydrodynamic lift force tends to push curved objects away from walls, as is known in the art. Usually, it is very small in applications such as those described here. Note that many different types of electrode array geometries can be used to generate suitable dielectrophoretic fields, and embodiments of this invention can encompass numerous configurations.

U.S. Pat. No. 5,626,734, incorporated by reference, addresses the use of a DEP force to prevent particles from being swept through holes in a filter. Representative embodiments of this disclosure are not intended to have holes larger than the particles and if the DEP force is insufficient to counterbalance the Stokes force, particles are pressed towards the holes and trapped as in a conventional filter.

Figure 35A:
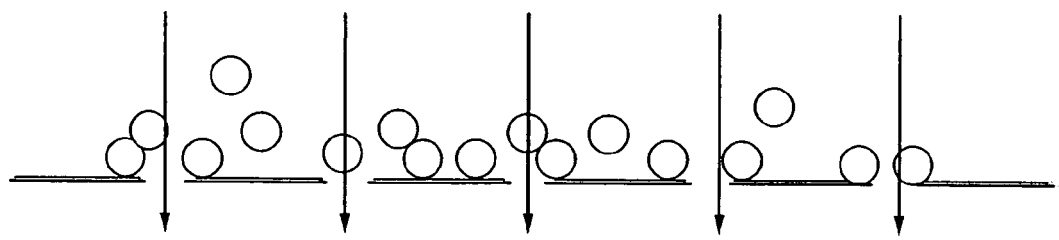
FIGS. 35A–B are schematic diagrams of filters, according to embodiments of the present disclosure.
Figure 35B:
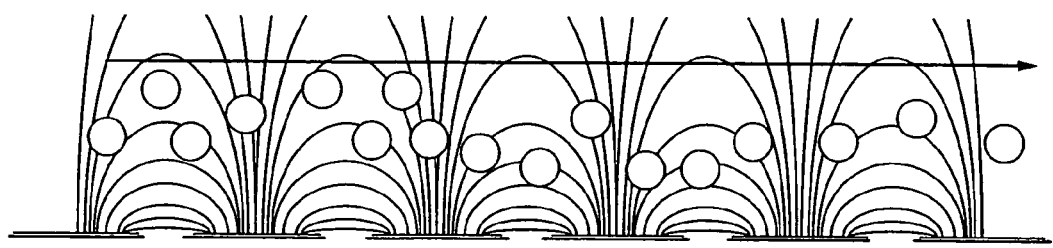

FIGS. 35A and 35B show use of repulsive DEP forces from electrodes on or near a dielectric filter to provide sample release to a second device. FIG. 35A is a filter mode showing conventional filtering of particulates from a transmembrane flow. The downward arrows show fluid flow through the filter membrane. FIG. 35B is a sample release mode showing electric field lines causing a levitating DEP force that allows filtered particles to be carried away from the filter with lateral flow (see arrow pointing to the right in FIG. 35B) to a sample processing or analysis stage.

Figure 36A:
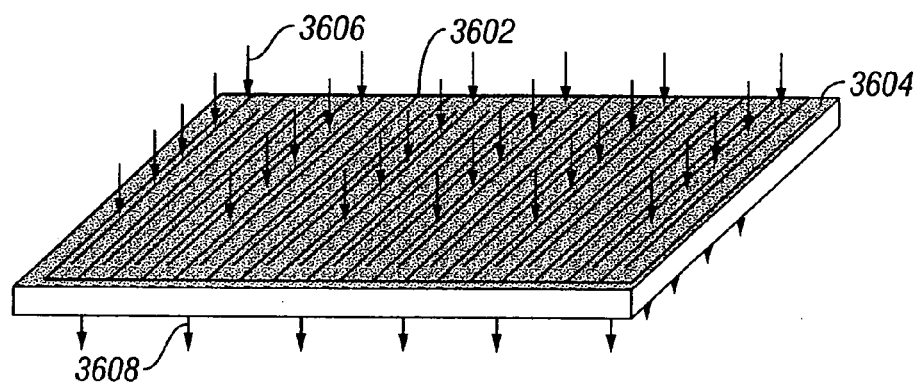
FIGS. 36A–B are schematic diagrams of filters, according to embodiments of the present disclosure.
Figure 36B:
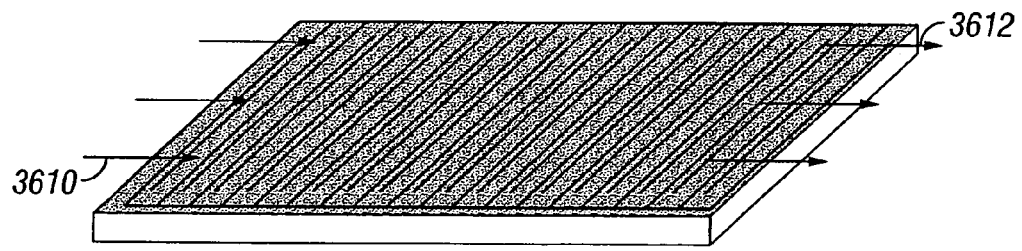

FIGS. 36A and 36B show isometric views of a filter embodiment. The electrode 3602 is shown patterned on top of a dielectric substrate 3604 which is perforated with holes for filtration. In use, the device can be contained within a chamber that facilitates the confinement of fluids above and below the filter and affords ports for connecting fluid paths for the sample inlet, waste, eluate inlet and sample plus eluate outlet. Arrows 3606 show sample flow during a filtering step. Arrows 3608 show fluid flow during a filtering step: sample waste. Arrows 3610 show the direction of eluate flow-in, and arrows 3612 show an eluate flow path during a sample release step.

Second Set of Embodiments

Figure 37:
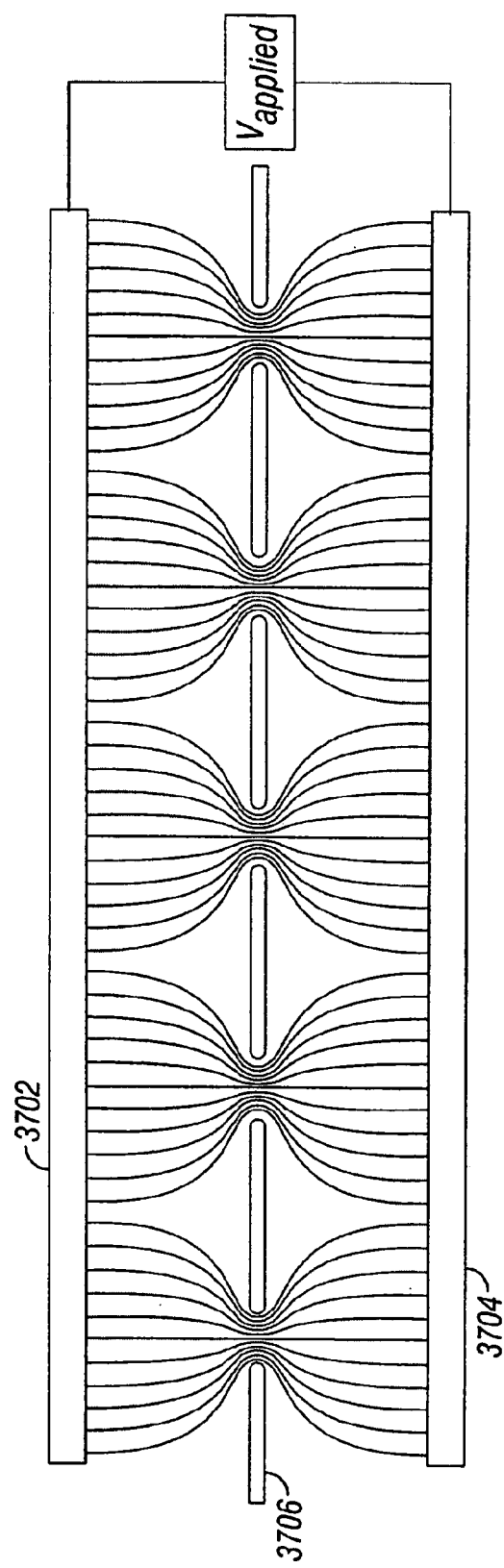
FIG. 37 is a schematic diagram of a filter, according to embodiments of the present disclosure.

FIG. 37 shows field lines close to a dielectric membrane that has an array of holes through which electric currents pass. Element 3702 is a top electrode, 3704 is a bottom electrode, and 3706 is a dielectric membrane having an array of holes.

Periodic holes and random holes of a defined count per unit area that puncture a dielectric barrier can be used to produce electric field distributions having periodic and pseudo-periodic field intensities, respectively. Except in close proximity to each hole, the inhomogeneity of the electrical field will fall off approximately exponentially with distance from the plane of the dielectric barrier. The spatial dependencies of the electric field can be used to produce dielectrophoretic forces to pull particles towards the plane of the dielectric or to push particles away, depending on the respective dielectric properties of the particles and the suspending medium.

Suitable dielectrics with holes include, but are not limited to, Gortex, polycarbonate track-etch filter (e.g. Whatman Nuclepore® Polycarbonate Track Etch Membranes, and similar products), and laser-drilled kapton or other polymers.

Figure 38:
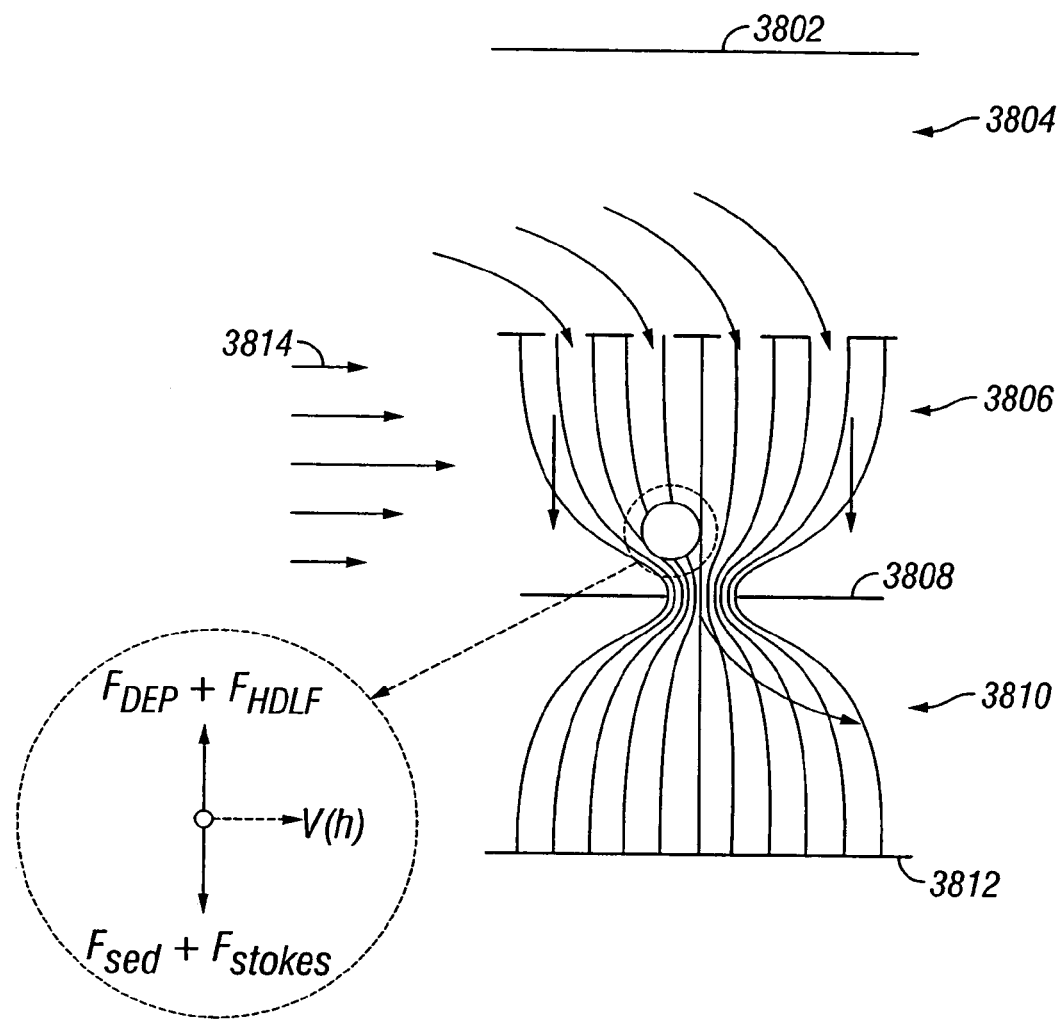
FIG. 38 is a schematic diagram illustrating principles of filtering, according to embodiments of the present disclosure.

FIG. 38 shows competing stokes and dielectrophoretic forces when an AC current passes through holes in a dielectric membrane and an associated force diagram. Element 3802 is a top electrode, 3804 is a cross-flow inlet channel, 3806 is a separation channel, 3808 is a dielectric membrane, 3810 is a cross-flow outlet channel, 3812 is a bottom electrode, and 3814 is an eluate flow profile. As in FIG. 34, FDEP represents a dielectrophoretic force, $F_{stokes}$ represents a stokes force, $F_{sed}$ represents a sedimentary force, and $F_{HDLF}$ represents a hydrodynamic lift force. The hydrodynamic lift force tends to push curved objects away from walls, as is known in the art. Usually, it is very small in applications such as those described here.

Figure 39A:
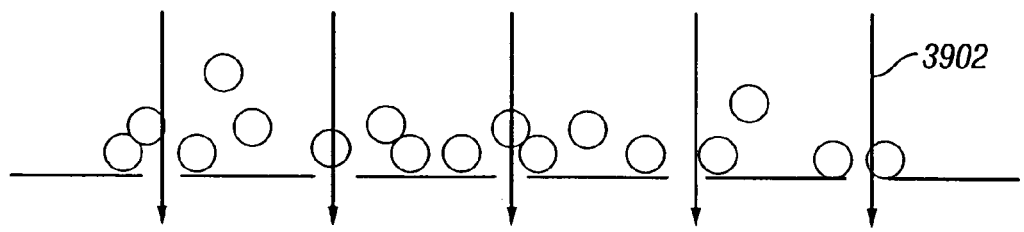
FIGS. 39A–B are schematic diagrams of filters, according to embodiments of the present disclosure.
Figure 39B:
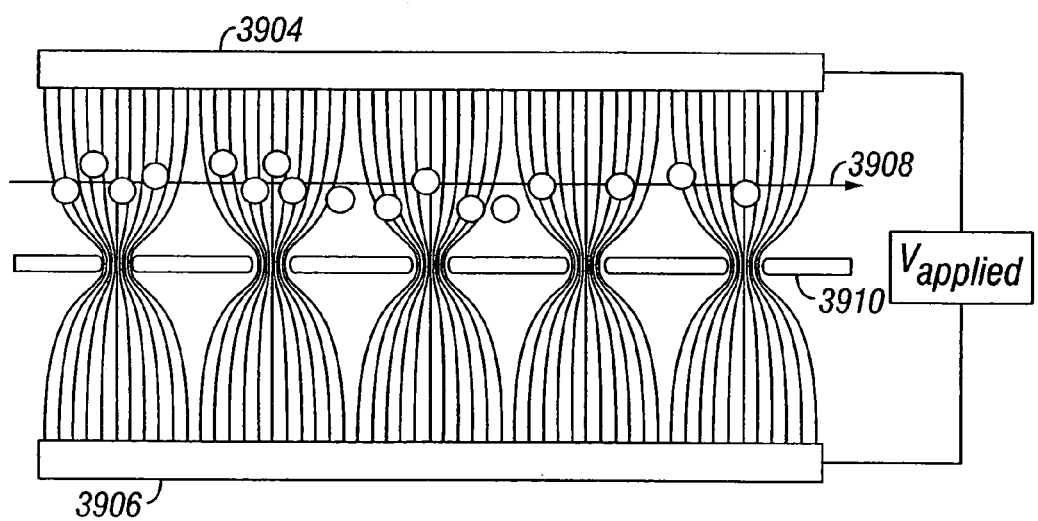

FIGS. 39A and 39B show using repulsive DEP forces from electrodes on or near a dielectric filter to provide sample release to a second device. FIG. 39A is a filter mode showing conventional filtering of particulates from a transmembrane flow. Arrows 3902 show fluid flow through the filter membrane. FIG. 39B is a sample release mode showing electric field lines causing a levitating DEP force that allows filtered particles to be carried away from the filter with lateral flow to an associated sample processing or analysis stage. Element 3904 is a top electrode, 3910 is a dielectric filter membrane, 3906 is a bottom electrode, and arrows 3908 show fluid flow to an associated sample processing or analysis stage.

Figure 40:
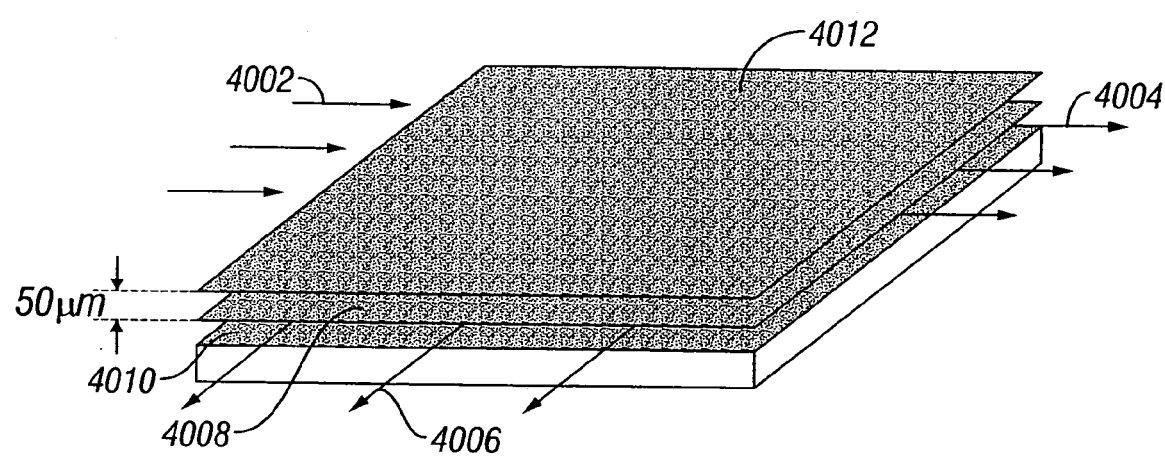
FIG. 40 is a schematic diagram of a filter, according to embodiments of the present disclosure.

FIG. 40 shows a filter in a configuration in which fluid flows between top and bottom electrodes. Arrows 4002 show the flow-in, 4004 shows fluid flow during sample recovery step, and 4006 shows fluid flow during filtering step. Element 4010 is a bottom electrode, and 4012 is a top electrode. In the illustrated embodiment, element 4008 is a polycarbonate track-etch filter, although those having ordinary skill in the art will recognize that other materials can be used. In this embodiment, the track-etch filter is spaced from the top electrode by 50 microns, although other distances can be used.

Figure 41:
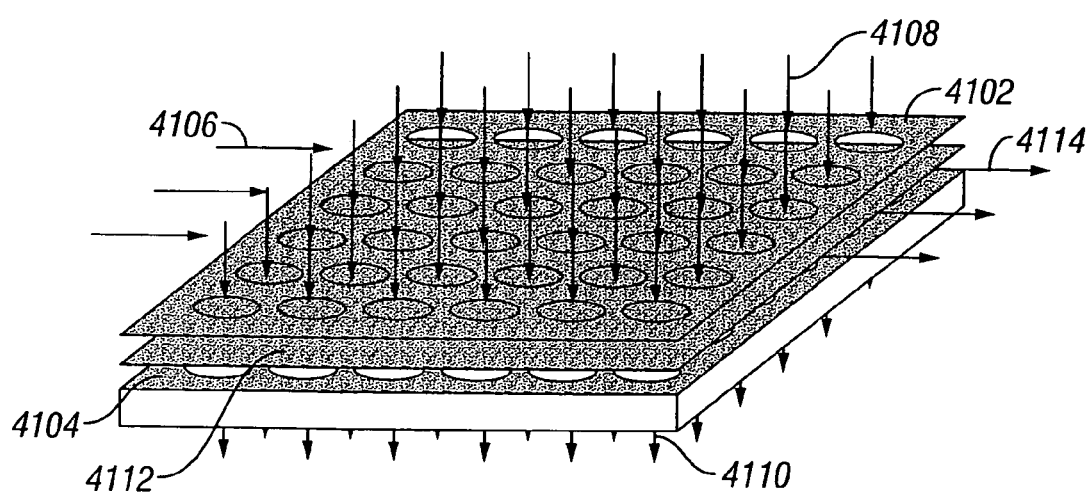
FIG. 41 is a schematic diagram of a filter, according to embodiments of the present disclosure.

FIG. 41 shows a filter in a configuration in which fluid flows through top and bottom electrodes. Arrows 4106 show flow-in, 4114 shows flow during sample recovery step, 4108 shows flow-in during filtering step, and 4410 shows flow-out during filtering step. Element 4104 is a bottom electrode, and 4102 is a top electrode. In the illustrated embodiment, element 4112 is a polycarbonate track-etch filter, although those having ordinary skill in the art will recognize that other materials can be used.

Third Set of Embodiments

Figure 42A:
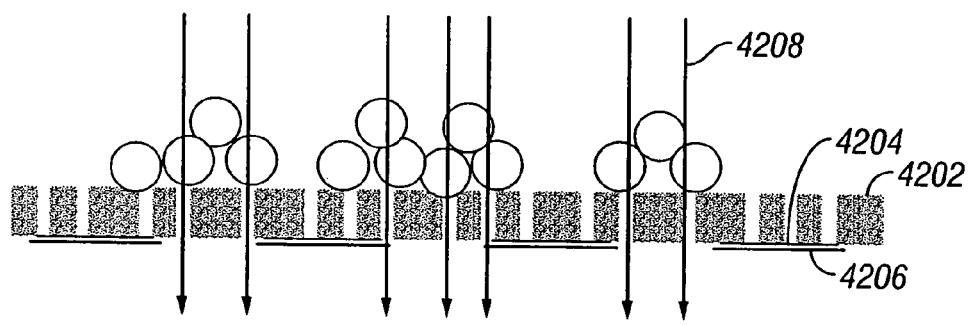
FIGS. 42A–B are schematic diagrams of filters, according to embodiments of the present disclosure.
Figure 42B:
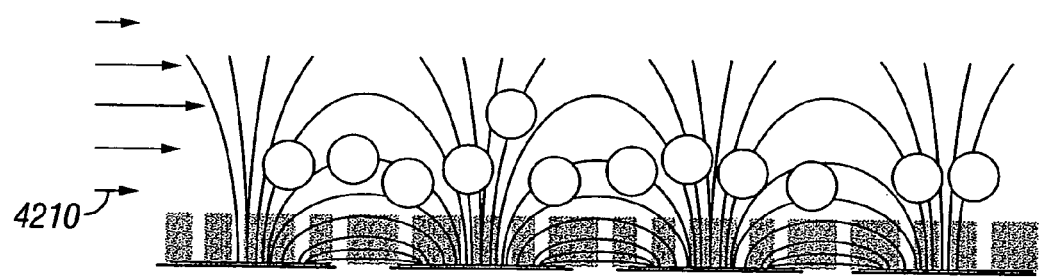
Figure 43A:
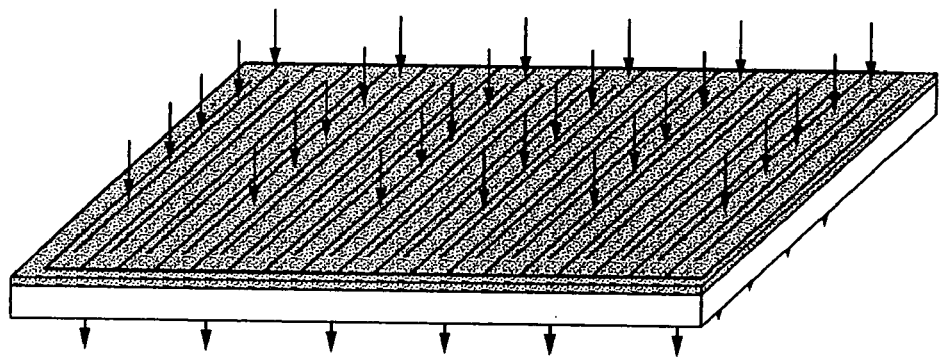
FIGS. 43A–B are schematic diagrams of filters, according to embodiments of the present disclosure.
Figure 43B:
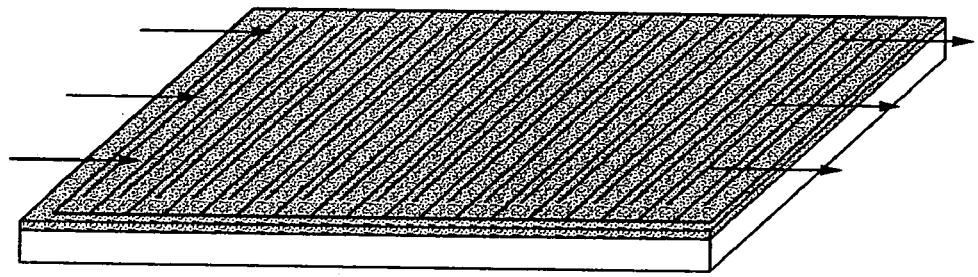

FIG. 42 shows using repulsive DEP forces from electrodes under a dielectric filter to provide sample release to an associated devices. This allows a fine filter to be supported on an electrode substrate with larger holes. FIG. 42A shows cross-flow sample collection and rinsing on the filter (see arrows 4208). Element 4202 is a dielectric or non-dielectric filter, 4204 is an electrode, and 4206 is a dielectric substrate with holes for fluid flow. FIG. 42B shows sample elution using DEP repulsion to clear the filter. Eluate flow is indicated by arrows 4210. FIGS. 43A and 43B show representative filters according to these embodiments. In FIG. 43A, sample flow during a filtering step is shown, and in FIG. 43B, an eluate flow path is shown for a sample release step.

Ports

Figure 44:
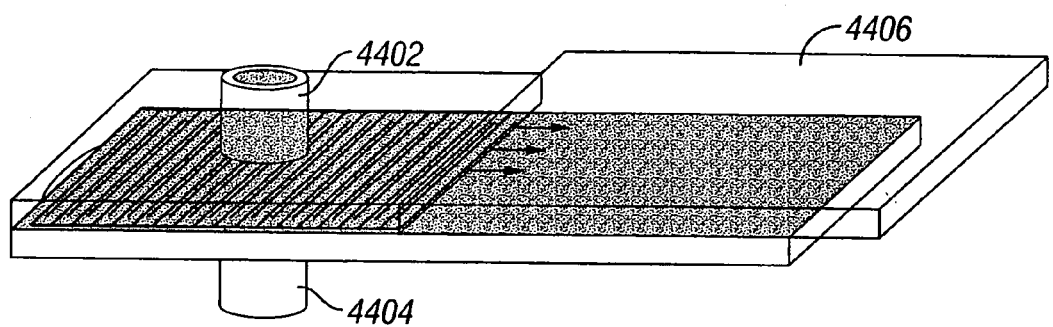
FIG. 44 is a schematic diagram illustrating ports, according to embodiments of the present disclosure.

FIG. 44 shows a generalized embodiment including ports 4402 and 4404. In one embodiment, section 4406 can be a DEP-FFF device or another device in accordance with embodiments of this disclosure.

Producing a Narrow Band of Particles

Figure 45A:
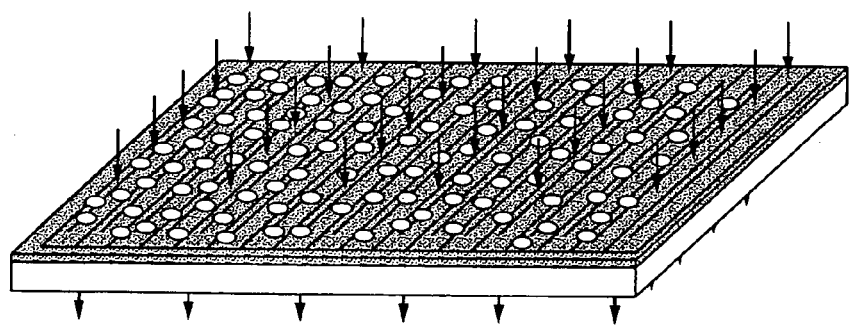
FIGS. 45A–C are schematic diagrams illustrating methodology for forming a narrow band of particles, according to embodiments of the present disclosure.
Figure 45B:
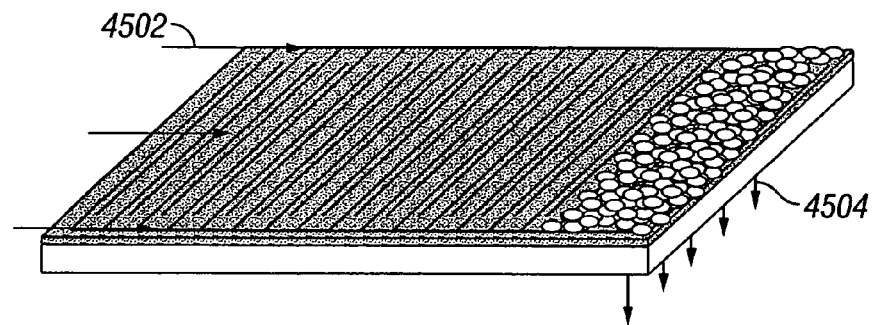
Figure 45C:
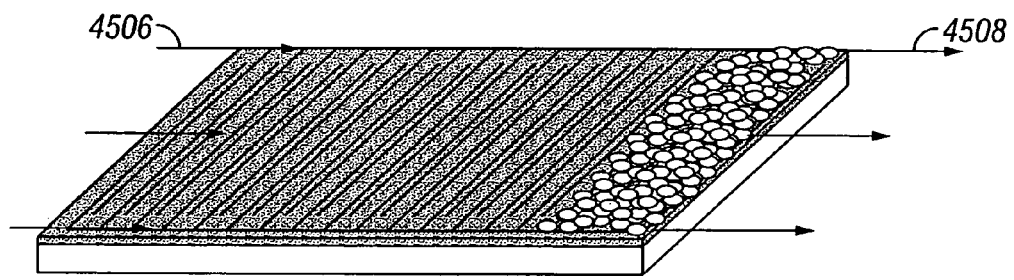

FIGS. 45A–45C show methods for producing a narrow band of particles for injection from a filter stage into an associated device (e.g., DEP-FFF or other stage that needs such a band). In general, FIG. 45A shows sample loading. FIG. 45B shows sample collection in narrow band ready for DEP-FFF or other application (e.g., electrosmear). Arrows 4502 show eluate flow-in, and arrows 4504 show eluate flow-out. FIG. 45C shows sample release into DEP-FFF or other application (e.g., electrosmear). Arrows 4506 show eluate flow-in, and arrows 4508 show eluate flow into DEP-FFF or other stage (e.g., electrosmear) that could benefit from a narrow band of particles.

The illustrated embodiments of FIGS. 45A–45C, there is shown a sample loading sequence designed to concentrate the sample ready for analysis by a second stage (not shown). In one embodiment, that stage could be an electrosmear stage as described in this application. In FIG. 45A, particulates are collected from a suspending medium by using the device as a DEP filter. In FIG. 45B, the specimen has all been filtered. To accumulate the filtered particulates in a narrow, concentrated band, new suspending medium is flowed along 4502 and 4504. This can also wash the sample and place it within in a more desirable suspension medium for analysis. For example, the conductivity of the suspending medium can be made more suitable for electrosmear analysis. Once the sample has been concentrated and resuspended in analysis medium, FIG. 45C shows the eluate buffer flow 4506 carrying the sample from the accumulation region of the filter into the electrosmear along 4508. As those having ordinary skill in the art will recognize having the benefit of this disclosure, the concentration into a narrow band is optional. Other features include the particle collection and subsequent washing steps and then, of course, the injection into the electrosmear. As illustrated in this disclosure, DEP can be used to stop the sample from sticking in the filter stage by keeping particles levitated.

Filters of this example allow many different sample types to be accommodated. For example, a sample may contain concentrated particles (e.g. blood) or be very dilute (e.g. bacteria in drinking water). After particles are filtered from the sample, they may be washed and/or treated with reagents while on the filter. For example, blood may be washed with a hypotonic buffer to lyse the red blood cells while leaving white cells intact.

Particles may also be stained or exposed to antibodies carrying reporter elements (e.g. fluorescent tags). Reagents may also be used to alter the dielectric properties of particles if desired or to fix them so that they remain stable during subsequent processing.

To avoid possible adherence issues, a filter may be covered with a layer of spacer beads or other particles, before a sample is filtered, that prevent particles trapped from the sample from coming into contact with the filter. The sample particles and spacer beads may be separated by methods such as DEP-FFF after release from the filter.

To collect target agents such as molecules, bacteria, viruses or other agents from a sample, a filter may be covered with a layer of one or more beads or other particle types carrying one or more antibodies or other affinity probes that will trap the target agents when the sample is filtered. The sample may be passed through the filter bed one or more times or re-circulated in order to increase the probability of trapping target agents that might otherwise pass through the filter. After trapping the target agents, the beads with their trapped target agent(s) may be released from the filter and processed by DEP-FFF or another discriminating method to resolve the one or more different target agents (e.g. the beads may be paramagnetic particles, dielectrically-engineered particles, or luminex-style color-indexed particles). In this way, assays for several target agents may be multiplexed, allowing multiple target agents to be detected in a single sample.

In some cases, target agents may not be a fluid suspension and may be present in a solid. Examples include those from air filters or samples of food, sediment, or soil, sewage sludge, slurry, slime or other solid materials. It may be necessary to add a suspending medium to such solids to allow the target agents to become suspended. The filter systems described here may be loaded with a solid sample and a suspending medium may be added subsequently to suspend the sample, allowing the target agents to be liberated from the solid background materials by a method such as, but not limited to, DEP-FFF.

EXAMPLE 6

Immobilization Using Physical Barriers

In addition to attachment methods utilizing chemical fixatives, immunological binding methods, or physical processes such as coulombic binding, particles in electrosmear applications may be immobilized in bands through physical traps such as wells between neighboring fingers of electrodes.

Figure 46:
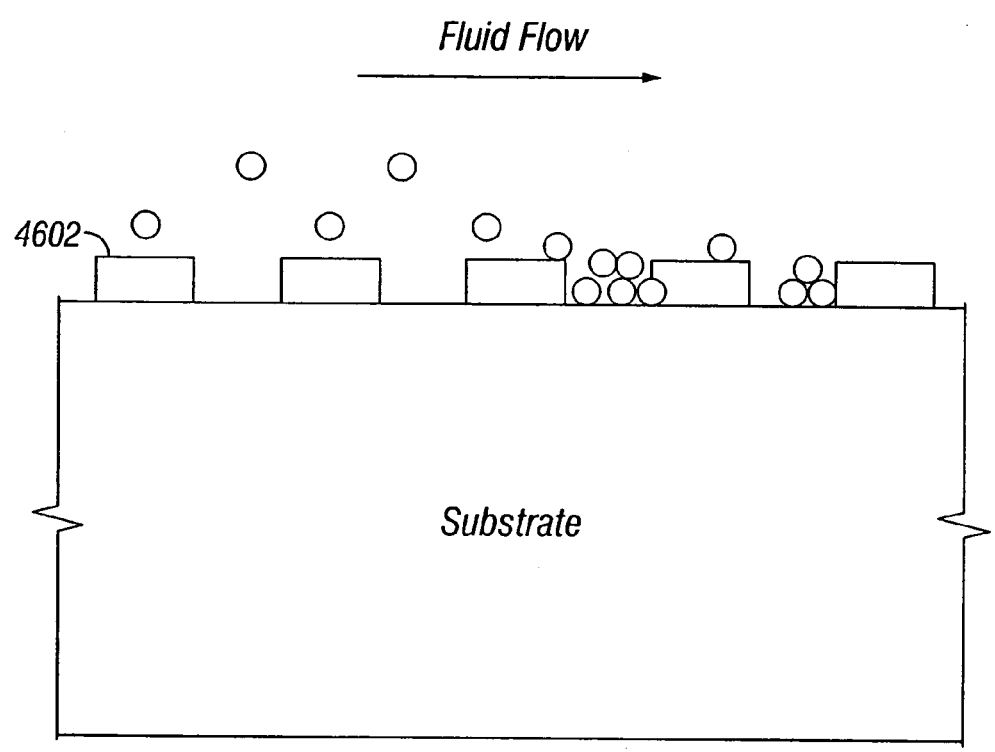
FIG. 46 is a schematic diagram illustrating adhering particles using physical barriers, according to embodiments of the present disclosure.

FIG. 46 shows a side view of an electrosmear (or other) discrimination device. Elements 4602 are electrodes. As can be seen, particles are constrained from motion by physical barriers once their DEP levitation height is insufficient to surmount those barriers.

In FIG. 46, one can see an electrode array in which the electrodes (seen in the figure from the side) are separated by wells that are deep enough to prevent fluid flow from sweeping particles along. This is a physical approach to immobilizing particles. More permanent attachment can be provided by, e.g., coating the particles immobilized in the wells with an adhesive or embedding material. One can think of this as a "cliff" approach to immobilization.

EXAMPLE 7

Related Applications

Various detection methods may be used with the electrosmear embodiments disclosed here. Particles may be viewed microscopically, or by other probe techniques such as atomic force microscopy, or scanning electron microscopy, and such analysis may occur before of after staining a sample with coloring, contrast or other enhancement agents that facilitate the resolution of information about the particles that may be of interest, or chemical or physical agents that aid in the discrimination of physical or chemical properties of the particles. Histochemical, antibody, and other methods from the life sciences may also be used.

Furthermore, in the case of viable bacteria, yeasts, spores, and cells, the characteristics of the particulates may be assessed by promoting the growth of the trapped biological particulates on the slide. To accomplish such growth promotion, the electrosmear slide may be coated with a suitable growth or attachment medium prior to capturing the biological particulates, or may be placed into a culture medium or coated with a suitable growth-promoting agar or agarose medium after the collection of biological particulates. In this way, the presence of viable colony forming units may be detected and the physical nature of the viable organisms that give rise to the growth of the colonies may be determined.

Figure 47A:
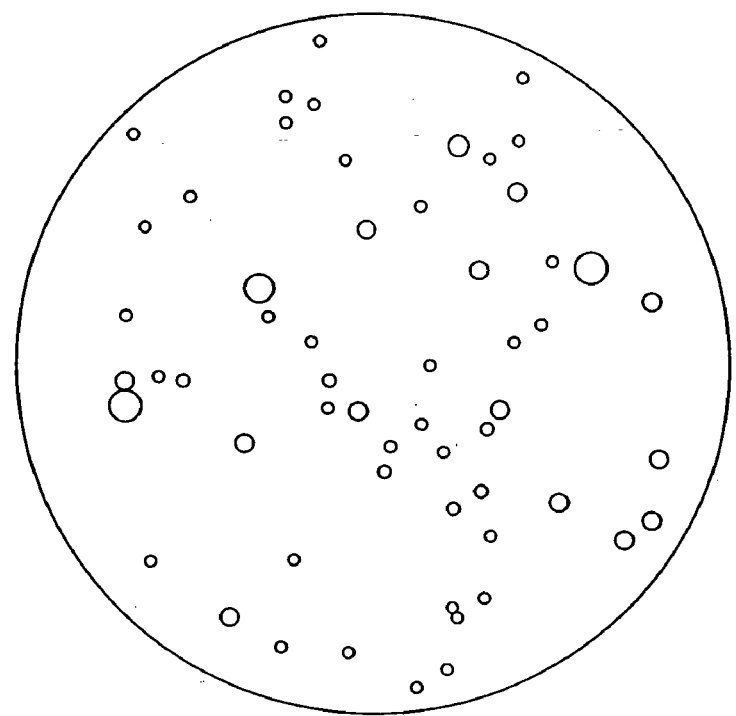
FIGS. 47A–B illustrate growth patters for a low concentration bacterium (A) and results from an equivalent electrosmear plate (B), according to embodiments of the present disclosure.
Figure 47B:
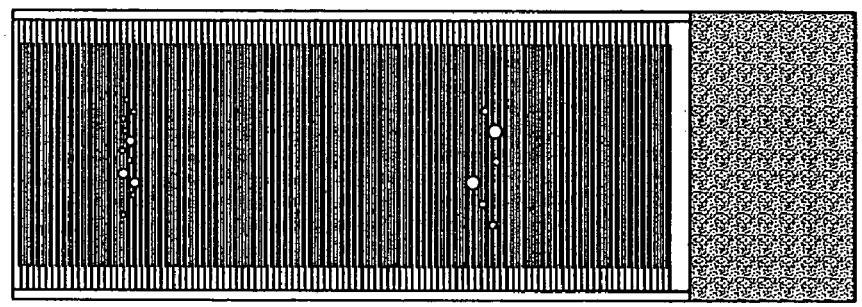

Because different types of bacteria have different dielectric and density characteristics, they are trapped in characteristically different bands on an electrosmear. Gram negative and gram positive bacteria have extremely different characteristics, for example. The spatial profile of growth patterns on an electrosmear exposed to in a growth-promoting treatment can therefore be used as a method to detect and to characterize pathogens and to determine whether more than one pathogen is present. FIG. 47A shows a typical growth pattern for a low concentration bacterium placed on an agar growth plate. It is clear from the growth on the agar that colony-forming units are present. However, no information is provided about how many different types of colony-forming agents are present or their characteristics. FIG. 47B shows results for an equivalent electrosmear plate. Here, it is readily apparent that three different bioagents are present. Furthermore, the characteristic trapping band positions may be related to specific bacteria or to classes of bacteria, allowing more rapid identification of the species. This improved method has important implications in at least the life sciences, medicine, vetinary medicine, agriculture and aquaculture, soil science, waste water management, public water distribution safety analysis, the detection of novel pathogens, and in the detection and characterization of biowarfare and bioterrorism agents. In these applications, the profile of bacteria is very important and determination of the characteristics of specific agents can have life-saving consequences.

Additional tests may also be performed following electrosmear capture of a specimen. For example, the response of cells to exposure to cytokines, growth hormones, drugs, toxins, chemotherapeutic agents, physical challenges such as exposure to electromagnetic or particle radiation, may be assessed and/or quantified. In this way, the sensitivity of cells to these agents may be determined and exploited for useful purposes such as chemotherapeutic treatment of tumors, eradication of pathogens with antibiotics, and the remediation of disease states through appropriate drugs and agents. Furthermore, the method may be used to verify the proper operation of bioreactors, yeast and wine-making processes, waste treatment through bacterially-active beds, and so on.

Use of the electrosmear allows not only the separation of the bioparticles into characteristic bands, but, in combination with a filter such as the DEP-release filter, permits great sensitivity to be attained. Specifically, the filter allows highly dilute bioagents to be captured from large volume samples. Furthermore, because biological particulates including cells, bacteria, yeasts, spores, plants, viruses, phages, and capsids have dielectrophoretic characteristics that are distinct from non-living debris, the electrosmear can be used to remove that debris, permitting analysis of biological particulates of interest.

If desired, bio particles that have been trapped on an electrosmear may be transferred to another substrate in a fashion that substantially retains the spatial relationships between captured particles. In this way, the histochemical, molecular, immunogenic, morphological, and/or growth characteristics of the captured particles may be examined. Following such examination, the spatial relationships of the particles may be used as an indexing mechanism to derive the dielectric and density properties that determine the spatial collection characteristics of the particles on the original electrosmear slide.

In the illustrated embodiment of FIG. 47B, the electrosmear slide would have to be "cultured" by immersing it in a culture broth or coating it with agar that contained appropriate nutrients. As will be understood by those having ordinary skill in the art with the benefit of this disclosure, the techniques of FIGS. 47A and 47B can apply to any application in which it was desired to grow an organism for further applications or tests.

EXAMPLE 8

Flow DEP-FFF

This example relates to flow DEP-FFF (field-flow-fractionation). In general, it relates to an extension of previous methods of DEP-FFF to include the use of fluid cross-flow (flow-FFF) as a force for driving particles towards a wall of a separation chamber. Flow DEP-FFF can be used in electrosmear applications as described here or in a very wide array of other applications (e.g., any application amenable to more conventional DEP-FFF techniques).

Theoretical underpinnings of flow DEP-FFF can be understood with reference to figures such as FIGS. 33A, 33B, 34, 37, and 38 and their associated descriptions, which will not be repeated here.

Figure 48:
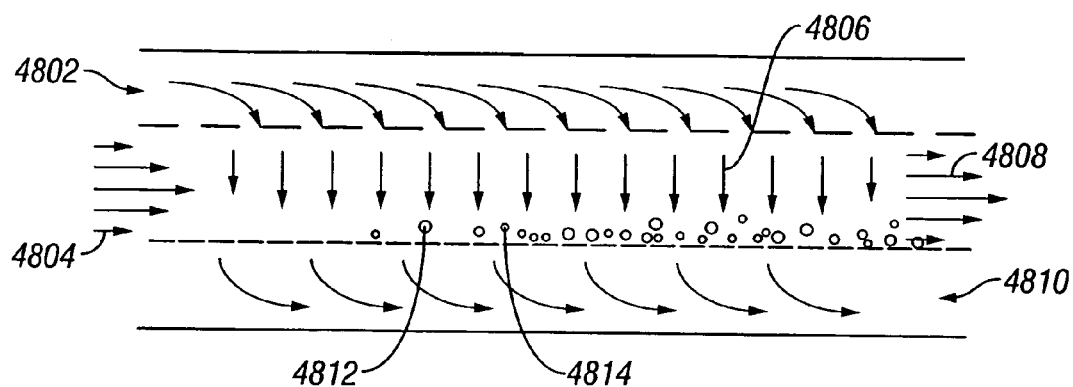
FIG. 48 illustrates a flow DEP-FFF apparatus and its associated methodology, according to embodiments of the present disclosure.

FIG. 48 illustrates a flow DEP-FFF apparatus and its associated methodology. Element 4802 is a cross-flow inlet channel, 4804 and 4808 show an eluate flow profile, 4806 shows fluid cross flow, 4810 is a cross-flow outlet channel, and 4812 and 4814 show different particle types being carried through the central channel at different speeds.

In flow-FFF, fluid cross-flow is used to generate a hydrodynamic (Stokes) force that carries particles towards one wall of the device. Eluate flows along the length of the central channel with a parabolic or other suitable velocity profile. In steric-flow-FFF, the cross-flow presses particles against the side of the central channel, and the velocity with which the particles are transported through the central channel is inhibited in accordance with the manner in which the particles and wall interact. Different particle types experience different steric forces and are therefore carried at different speeds. In the example here, electrodes may be positioned on, near to, or on either side, of the filter to provide the DEP forces to oppose or augment the stokes forces from the fluid cross-flow as shown.

Figure 49:
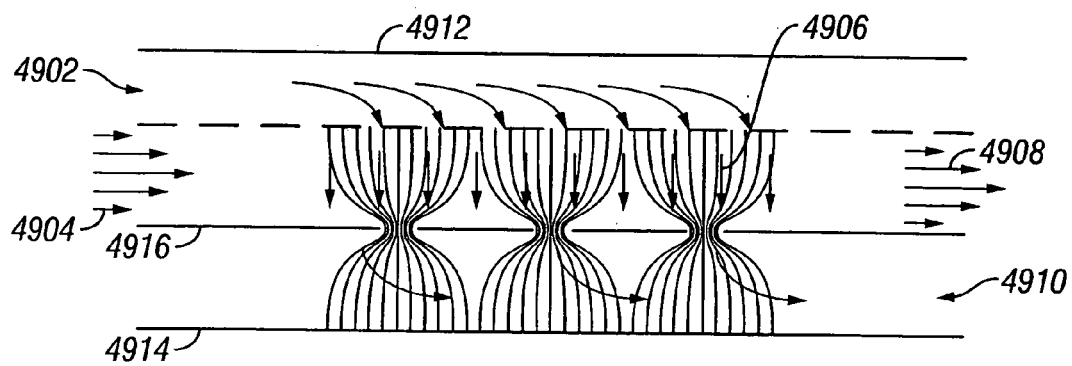
FIG. 49 illustrates another flow DEP-FFF apparatus and its associated methodology, according to embodiments of the present disclosure.

FIG. 49 illustrates another flow DEP-FFF apparatus and its associated methodology (including field lines). In this figure, a dielectric membrane is used to generate inhomogeneous fields-holes in the dielectric membrane pinch the field generated by electrodes on either side of the dielectric membrane. Element 4902 is a cross-flow inlet channel, 4904 and 4908 show an eluate flow profile, 4906 shows fluid cross flow, and 4910 is a cross-flow outlet channel. Element 4912 is a top electrode, and 4914 is a bottom electrode. A dielectric membrane is shown as element 4916.

The description below focuses on methods and apparatus of particle separation and fractionation based on flow-DEP-FFF, which can be applied to the electrosmear and other applications described here, among other applications. The inventors have previously disclosed inventions in which a dielectrophoretic force is used in conjunction with sedimentation or magnetic forces to control the position of particles in a hydrodynamic flow profile and thereby drive the separation of dissimilar particles by the mechanisms of field-flow-fractionation. Those disclosures have successfully opened new approaches to particle fractionation based on differences in particle dielectric properties and/or susceptibility to magnetic fields (perhaps based on labeling with, for example, magnetically-labeled antibodies).

While those methods are widely applicable, and in particular have been very successfully applied to discriminating between and fractionating different cell types, when applied to particles below approximately 2 microns they typically require long settling times to equilibrate the forces acting on the particles before the initiation of flow separation can begin if high resolution is to be attained. While not preventing those methods from being applied to the analysis or preparation of bacteria and smaller bio-particles, especially if magnetic or other labeling methods are applied to enhance the settling, those methods may not be as convenient for such smaller particles, although they will still work. One purpose of this example is to address this problem and to introduce a mechanism of DEP-FFF in which fast settling times are provided for small particles.

Improvements are accomplished through at least two innovations. First, the predominant force used to drive the particles to one wall of the separation channel is Stokes drag which is created from introducing a fluid flow component that runs, in a preferred embodiment, substantially perpendicularly to the eluate flow that carries particles through the separation chamber. In other embodiments at least a component of flow may be substantially perpendicular. Second, whereas the electric field and field gradient upon which the dielectrophoretic force depends is created by an electrode array on one wall of DEP-FFF and DEP-MAG-FFF chambers, a dielectric membrane, rather than an electrode, can be used to create the electric field and electric field inhomogeneity in this example.

Compared to conventional flow-FFF methodology, the flow-DEP-FFF method allows steric interactions of particles with the walls to be avoided.

The new method allows particles to settle ready for separation in one minute or less, compared to 10 minutes or more for DEP-FFF and MAG-DEP-FFF. Furthermore, the separation rate does not depend on the particle size or density.

The use of a dielectric membrane with holes to create the electric field and field inhomogeneity reduces or eliminates the potentially negative impacts of low-frequency electroosmotic, electrode polarization, AC electrokinetic, and electrochemical effects that occur at electrode-solution interfaces.

The cross-flow method also allows for the shape of the hydrodynamic flow profile to be modulated, as is known in flow-FFF.

A non-limiting representative flow-DEP-FFF apparatus includes: a channel having an inlet for a sample and at least one outlet for fractionated sample, a means of introducing fluid (e.g., a channel, pump, syringe, etc.) so as produce a fluid flow profile capable of transporting sample through the chamber, an array of electrodes disposed within a chamber, a means of exciting the electrodes (e.g. a controller or generator) so as to produce a DEP force on particles within the sample, a means of allowing fluid to pass through at least one wall of the chamber (e.g. an opening) such that the fluid flow resulting from such fluid passage causes particles in the chamber to be carried towards a wall, wherein the fluid flow forces resulting from the passage of fluid through the chamber wall are opposed by dielectrophoretic forces resulting from the electrode array such that the position of the particles in the sample within the flow profile are controlled so as to yield separation.

Useful electrodes include an interdigitated electrode or other array that produces an inhomogeneous electric field. However, the inhomogeneous field can also be provided by an array of small holes through a dielectric membrane. The electric field lines on either side of each small hole will be inhomogeneous, allowing a DEP force to be produced. The same holes can provide a pathway for the fluid that carries particles towards the walls. In a preferred embodiment, the holes should be of the same order of size as the particles. Holes smaller than the particles is better because then the particles cannot be carried through the holes. In the case of holes being smaller than the particles, the wall with the holes can act as a passive filter membrane as well as an active DEP surface.

In another embodiment, a spiral array could be used, and flow through the membrane could control the ease with which particles could be transported to or away from the center of the spiral by twDEP.

The rate of the fluid flow through the sidewalls, and the electrical field strength and frequency, can be adjusted or programmed with time, as is known in the art, to facilitate better separations.

Representative and non-limiting uses of the techniques of this example include but are not limited to: collection, fractionation, characterization, isolation, identification, of inorganic and organic particles, sediments, cells, bacteria, viruses, phages, cellular organelles, mitochondria, nuclei, vesicles, starch particles, ores, macromolecular complexes, beads, dielectrically-engineered microparticles, etc.

Other uses include bacterial detection and identification in the environment, bacterial cell profiling in effluents, waste water, ponds, soils, ecosystems, bacterial analysis in bioreactors, and soil sediment, dust, smoke, and other microparticle profiling and analysis.

Other uses include blood cell differential preparation or analysis, collection and processing of residual cancer cells other and rare cells in suspensions—e.g., tumor cells in nipple aspirate, cancer cells in suspensions of lymph node cells, nucleated fetal cells from amniotic fluid, maternal blood, and other fluids, mycoplasma, bacteria, fungal, prion, or viral particles from blood, urine, feces, lavage, phlegm, spinal fluid, ascitic fluid, amniotic fluid, nipple aspirate, saliva, semen, sweat, mucous, water, food, bioreactor medium, milk, oil, swimming pools, drainage ditches, canals, lakes, reservoirs, ice machines, oil pipelines, drinks, sap, rain, snow, ice, seawater, condensate, puss, bilgewater, etc.

One advantage over conventional FFF is the ability to work with small (i.e. micron and smaller particles) that have low sedimentation rates or large Brownian motion. The methods of this example can also be used to settle larger cells and particles more quickly than sedimentation. Finally, the methods of this example can be used to filter a small number of particles from a volume suspension allowing larger sample volumes to be processed than is convenient with conventional DEP-FFF.

In different embodiments, the techniques of this example can be used in conjunction with, and/or as a front end to, DEP-FFF, gDEP-FFF, and MAG-DEP-FFF devices. In particular, the device could function as a pre-collector for DEP-FFF that allows particles, bacteria, or cells to be collected from a sample and then flow-DEP-FFF fractionated and/or injected into a DEP-FFF device or other sample processor or analyzer. In that mode of operation, the FFF flow profile could be turned off, or the cross-flow rate made much larger, so that particles are filtered from a sample stream. Afterwards, the cross-flow can be reduced or stopped and the FFF flow initiated. Note that in this case the DEP force plays no role in preventing particles in the sample from going through the filter. Instead, DEP is used as a means to provide a force for controlling the particle height for flow-DEP-FFF discrimination and separation along the direction leading towards the sample outlet.

Magnetic forces can also be used in a device that combines cross-flow and MAG forces to oppose DEP forces.

Membrane Material

In preferred embodiments, the filter membrane must be dielectric (non-conducting electrically) in nature: glass, ceramic, plastic, polymer, mineral (e.g. mica), Kaptan (polyimide), Teflon, etc. In preferred embodiments, it must have holes, pores, or other pathways through it that allow ionic conductivity. Typical examples are Nucleopore membranes made of polycarbonate with well-defined holes etched through, Gortex (TEFLON, PTFE) sheeting with a suitable size distribution of holes, laser-punched or etched Kaptan, etc.

In preferred embodiments, holes can be in the range of 10 mm to 100 micrometers, depending on the particle size, and more typically 0.1 to 10 microns. However, other suitable sizes will be apparent to those of ordinary skill in the art, and this application is not limited to particular sizes.

Electrical Fields

In preferred embodiments, applied fields can be in the range 0.1 to 100 volts, AC, at frequencies from 0 (DC) to 100 GHz and more typically 0.2 to 10 volts at frequencies from 1 kHz to 100 MHz. However, other suitable ranges will be apparent to those of ordinary skill in the art, and this application is not limited to particular ranges.

With the benefit of the present disclosure, those having skill in the art will comprehend that techniques claimed herein and described above may be modified and applied to a number of additional, different applications, achieving the same or a similar result. For example, although embodiments of this disclosure focus on forming smears of cells, one having ordinary skill in the art will recognize that the same techniques can be applied to any other type of particle within a sample. The claims cover all modifications that fall within the scope and spirit of this disclosure.

For example, although certain embodiments described here may be directed primarily towards cytopathology, the present methodology can also be used with, e.g., multi-celled organisms, e.g. with parasites, nematodes, etc. Methodology can also be used with other samples not involving cells where dielectric properties of particles are exploited. For example, a mixture of dielectrically engineered beads having different dielectric signatures can be displayed and analyzed this way. Bacteria, viruses, spores, amoebae, nematodes, yeasts, fungi, and small protozoans can be separated from biological fluids including blood, sputum, nipple apirate, lavage, urine, sebum, or diarrhea or from soil, effluent, or water and analyzed.

Soil and sediment samples can also be analyzed for dielectric and density differences that can reveal their composition, the presence of ores, and organic components, including particles indicative of petrochemicals, for example. Samples for such applications can be attached or immobilized by a wider variety of approaches including a coating of adhesive or polymer, or embedding after collection. Staining for such samples can also include chemical reactions to reveal elemental or chemical composition.

Accordingly, the applications for methodology in this disclosure is very vast. For example, in addition to cervical cancer and the other applications, techniques of this disclosure can be applied to, e.g., detection of cancer cells in marrow samples, in sentinel lymphatic nodes adjacent to tumors during surgery, and in fine needle aspiration biopsies. In addition to the non-biological examples listed, the techniques can also be applied to, e.g., bioagent detection.

REFERENCES

Each of the following references is incorporated herein by reference in its entirety:
U.S. Pat. No. 6,437,551
U.S. Pat. No. 6,352,838
U.S. Pat. No. 6,294,063
U.S. Pat. No. 6,287,832
U.S. Pat. No. 6,264,815
U.S. Pat. No. 5,993,632
U.S. Pat. No. 5,993,630
U.S. Pat. No. 5,888,370
U.S. Pat. No. 5,858,192
U.S. Pat. No. 5,626,734
U.S. Pat. No. 5,302,898
U.S. Pat. No. 5,191,899
U.S. Pat. No. 6,436,662
U.S. Pat. No. 6,264,815
Masuda et al., IEEE Transactions on Industry Applications 25(4):732–737(1989)
Lee et al., Engineering in Medicine and Biology Society: Proc. 16th Annual International Conf. IEEE 2:1019–1020 (1994) ISBN:0-7803-2050-6)

The invention claimed is:

1. A method comprising:
subjecting particles of a sample to a dielectrophoretic force by simultaneously applying a swept frequency signal to a first set of electrodes and a fixed frequency signal to a second set of electrodes;
segregating the particles into two or more zones of a surface; and
attaching the particles to the surface; where the swept frequency signal falls from a maximum intensity to a minimum intensity along a length of a surface in a first direction, and the fixed frequency signal falls from a maximum intensity to a minimum intensity along the length of the surface in a second direction opposing the first direction.

2. The method of claim 1, where the intensities vary linearly along the length of the surface.

3. The method of claim 1, where the intensities vary non-linearly along the length of the surface.

4. The method of claim 1, where the intensities are varied by varying a width of electrode buses with distance along a length of the surface.

5. The method of claim 1, where the minimum intensity of the swept frequency or fixed frequency signal is non-zero.

6. The method of claim 1, further comprising filtering the sample by subjecting particles of the sample to a flow, a cross flow, and a dielectrophoretic force that opposes a force associated with the cross flow.

7. The method of claim 6, where the flow and cross flow are substantially perpendicular to one another.

8. The method of claim 6, where the flow and cross flow are not perpendicular.

9. The method of claim 6, where the dielectrophoretic force arises from the excitation of electrodes near a dielectric substrate having openings.

10. The method of claim 6, where the dielectrophoretic force arises from current passing through an opening in a dielectric barrier.

11. The method of claim 1, where attaching the particles into two or more zones comprises confining particles in a particular zone using a physical barrier.

12. The method of claim 1, where segregating the particles comprises flow DEP-FFF.

13. The method of claim 1, further comprising promoting growth of particles on the surface.

14. The method of claim 1, further comprising automatically adjusting the swept frequency signal or fixed frequency signal as a function of conductivity of a particle suspending medium.

15. A method comprising:
subjecting particles of a sample to a dielectrophoretic force to segregate the particles into two or more zones of a surface by simultaneously applying a swept frequency signal applied to a first set of electrodes and a fixed frequency signal to a second set of electrodes;
attaching the particles to the surface, thereby defining a segregated smear; and
fixing or staining the segregated smear; where the swept frequency signal falls from a maximum intensity to a minimum intensity along a length of a surface in a first direction, and the fixed frequency signal falls from a maximum intensity to a minimum intensity along the length of the surface in a second direction opposing the first direction.

16. The method of claim 15, comprising fixing and staining the segregated smear.

17. The method of claim 15, the attaching comprising subjecting the particles to a dielectrophoretic force.

18. The method of claim 15, the attaching comprising using an adhesive coupled to the surface.

19. The method of claim 15, the attaching comprising allowing the particle to settle on the surface.

20. The method of claim 15, the particles comprising cells.

21. The method of claim 15, the smear comprising a pap smear.

22. The method of claim 15, where subjecting particles to a dielectrophoretic force comprises subjecting the particles to a dielectrophoretic force arising from the simultaneous application of programmed voltage signals of different frequencies.

23. The method of claim 15, where subjecting particles to a dielectrophoretic force comprises subjecting the particles to a dielectrophoretic force arising from the application of frequencies exhibiting one or more DEP-FFF and trapping phases.

24. The method of claim 15, where subjecting particles to a dielectrophoretic force comprises subjecting the particles to dielectrophoretic forces generated by electrodes coupled to the surface.

25. The method of claim 24, the electrodes comprising spiral electrodes.

26. The method of claim 15, the two or more zones comprising concentric circular zones.

27. The method of claim 15, the two or more zones comprising distinct bands of particles.

28. The method of claim 15, where the intensities vary linearly along the length of the surface.

29. The method of claim 15, where the intensities vary non-linearly along the length of the surface.

30. The method of claim 15, where the intensities are varied by varying a width of electrode buses with distance along a length of the surface.

31. The method of claim 15, where the minimum intensities of the swept frequency and fixed frequency signals are non-zero.

32. The method of claim 15, further comprising automatically adjusting the swept frequency signal or fixed frequency signal as a function of conductivity of a particle suspending medium.

33. The method of claim 15, further comprising filtering the sample by subjecting particles of the sample to a flow, a cross flow, and a dielectrophoretic force that opposes a force associated with the cross flow.

34. The method of claim 33, where the flow and cross flow are substantially perpendicular to one another.

35. The method of claim 33, where the flow and cross flow are not perpendicular.

36. The method of claim 33, where the dielectrophoretic force arises from the excitation of electrodes near a dielectric substrate having openings.

37. The method of claim 33, where the dielectrophoretic force arises from current passing through an opening in a dielectric barrier.

38. The method of claim 33, where attaching the particles into two or more zones comprises use of a physical barrier to confine particles in a particular zone.

39. The method of claim 15, where particles are segregated using flow DEP-FFF.

40. The method of claim 15, further comprising promoting growth of particles on the surface.

41. An apparatus comprising:

a surface;

electrodes near the surface;

a first signal generator configured to apply a fixed frequency signal to a first electrode, the fixed frequency signal falling from a maximum intensity to a minimum intensity along a length of the surface in a first direction;

a second signal generator configured to apply a swept frequency signal to a second electrode, the swept frequency signal falling from a maximum intensity to a minimum intensity along the length of the surface in a second direction opposing the first direction, where the fixed frequency signal and the swept frequency signal are applied simultaneously; and where applying the swept frequency signal in combination with the fixed frequency signal generates a dielectrophoretic force configured to segregate particles into two or more zones of the surface.

42. The apparatus of claim 41, where the first and second signal generators are integral.

43. The apparatus of claim 41, further comprising a filter coupled to the surface, the filter configured to subject particles of a sample to a flow, a cross flow, and a dielectrophoretic force that opposes a force associated with the cross flow.

44. The apparatus of claim 43, the filter comprising electrodes near a dielectric substrate having openings.

45. The apparatus of claim 41, further comprising a physical barrier near the surface configured to attach particles into two or more zones of the surface.

* * * * *